United States Patent
Gavathiotis et al.

(10) Patent No.: US 11,813,268 B2
(45) Date of Patent: Nov. 14, 2023

(54) MITOFUSIN ACTIVATORS AND USES THEREOF

(71) Applicant: Albert Einstein College of Medicine, Bronx, NY (US)

(72) Inventors: Evripidis Gavathiotis, Roslyn, NY (US); Richard N. Kitsis, New York, NY (US); Nikolaos Biris, Lancaster, NY (US); Emmanouil Zacharioudakis, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 148 days.

(21) Appl. No.: 16/643,986

(22) PCT Filed: Oct. 16, 2018

(86) PCT No.: PCT/US2018/056002
§ 371 (c)(1),
(2) Date: Mar. 3, 2020

(87) PCT Pub. No.: WO2019/079243
PCT Pub. Date: Apr. 25, 2019

(65) Prior Publication Data
US 2020/0261469 A1    Aug. 20, 2020

Related U.S. Application Data

(60) Provisional application No. 62/573,217, filed on Oct. 17, 2017.

(51) Int. Cl.
| | |
|---|---|
| *A61K 31/4196* | (2006.01) |
| *A61K 31/551* | (2006.01) |
| *A61K 31/165* | (2006.01) |
| *A61K 31/167* | (2006.01) |
| *A61K 31/277* | (2006.01) |
| *A61K 31/341* | (2006.01) |
| *A61K 31/351* | (2006.01) |
| *A61K 31/402* | (2006.01) |
| *A61K 31/415* | (2006.01) |
| *A61K 31/42* | (2006.01) |
| *A61K 31/4245* | (2006.01) |
| *A61K 31/429* | (2006.01) |
| *A61K 31/437* | (2006.01) |
| *A61K 31/4985* | (2006.01) |
| *A61K 31/5025* | (2006.01) |
| *A61K 31/506* | (2006.01) |
| *A61K 31/519* | (2006.01) |

(52) U.S. Cl.
CPC .......... *A61K 31/551* (2013.01); *A61K 31/165* (2013.01); *A61K 31/167* (2013.01); *A61K 31/277* (2013.01); *A61K 31/341* (2013.01); *A61K 31/351* (2013.01); *A61K 31/402* (2013.01); *A61K 31/415* (2013.01); *A61K 31/4196* (2013.01); *A61K 31/42* (2013.01); *A61K 31/429* (2013.01); *A61K 31/4245* (2013.01); *A61K 31/437* (2013.01); *A61K 31/4985* (2013.01); *A61K 31/506* (2013.01); *A61K 31/5025* (2013.01); *A61K 31/519* (2013.01)

(58) Field of Classification Search
CPC ................. A61K 31/4164; A61K 31/4196
See application file for complete search history.

(56) References Cited

U.S. PATENT DOCUMENTS

| | | |
|---|---|---|
| 4,123,560 A | 10/1978 | Hice |
| 5,506,258 A | 4/1996 | Christophe et al. |
| 6,245,817 B1 | 6/2001 | Connell et al. |
| 2009/0105240 A1* | 4/2009 | Mustelin ............. A61K 31/433 514/231.5 |

FOREIGN PATENT DOCUMENTS

WO    WO-2018200323 A1 * 11/2018    ............... C12N 9/16

* cited by examiner

*Primary Examiner* — James D. Anderson
(74) *Attorney, Agent, or Firm* — Fox Rothschild LLP

(57) ABSTRACT

Activators of mitofusins and their uses in treatment of diseases and disorders are disclosed.

16 Claims, 15 Drawing Sheets

Specification includes a Sequence Listing.

| | R₁: | R₂: | R₃: | IC₅₀ (µM) |
|---|---|---|---|---|
| MASM7 | cyclopenta[b]thiophene-3-carboxamide | –CH₃ | cyclopropyl | 31 |
| MASM19 | –C(O)NH₂ | –CH₃ | cyclopropyl | > 150 |
| MASM20 | cyclopenta[b]thiophene-3-carboxamide | –CH₃ | phenyl | 95 |
| MASM21 | cyclopenta[b]thiophene-3-carboxamide | –H | cyclopropyl | 47 |
| MASM22 | cyclopenta[b]thiophene-3-carboxamide | –CH₃ | 2-furyl | 31 |
| MASM23 | cyclopenta[b]thiophene-3-carboxamide | –CH₃ | 5-methyl-2-furyl | 46 |
| MASM24 | methyl-tetrahydrobenzo[b]thiophene-3-carboxamide | –H | cyclopropyl | 32 |

FIG. 2

MITOFUSIN ACTIVATORS AND USES THEREOF

CROSS-REFERENCE TO RELATED APPLICATIONS

This application claims the benefit of U.S. Provisional Patent Application No. 62/573,217, filed on Oct. 17, 2017, the contents of which are herein incorporated by reference into the subject application.

STATEMENT REGARDING FEDERAL FUNDING

This invention was made with government support under grant number HL128071 awarded by the National Institutes of Health. The government has certain rights in the invention.

BACKGROUND OF THE INVENTION

Throughout this application various publications are referred to by number in parentheses. Full citations for these references may be found at the end of the specification. The disclosures of these publications, and all patents, patent application publications and books referred to herein, are hereby incorporated by reference in their entirely into the subject application to more fully describe the art to which the subject invention pertains.

Mitochondria are highly dynamic organelles that fuse and divide constantly; the physiological processes that regulate mitochondrial dynamism are fusion and fission, respectively (1). There is a large variability in mitochondrial morphology observed among different types of cells and within the same cell, as mitochondria can morph into small spheres, short rods to long tubules. Fusion allows mitochondria to exchange contents (e.g. lipid membranes, proteins). Such an exchange has implicated fusion in mitochondrial repair, as it permits the restoration of damaged components from healthy to defective mitochondria (2).

The fusion machinery includes mitofusin (Mfn) 1 and 2 on the outer mitochondrial membrane (OMM) and optic atrophy (Opa) 1 on the inner membrane (2, 3). Mfn1 and Mfn2 share high sequence homology (3). Both homologs possess a N-terminal GTPase domain, a coiled-coiled heptad repeat (HR1) domain, a short transmembrane domain responsible for anchoring Mfns on the OMM, and a second coiled-coiled heptad repeat (HR2) domain located in the C-terminus (2-4). The initial step in fusion is tethering of the OMMs of adjacent mitochondria. HR2 domains of Mfns from two adjacent mitochondria interact in an anti-parallel trans manner to form homotypic (Mfn1-Mfn1 or Mfn2-Mfn2) or heterotypic (Mfn1-Mfn2) complexes, subsequently mediating mitochondrial tethering (4). Franco et al. recently proposed a model in which Mfn2 undergoes conformational changes to promote mitochondrial tethering (5). Based on this model, Mfn2 can adopt anti- or pro-tethering conformations (5). In the anti-tethering conformation, HR2 interacts intra-molecularly with HR1 in an anti-parallel manner. On the other hand, in the pro-tethering conformation HR1-HR2 interactions are disrupted, and the HR2 domain extends into the cytosol to mediate mitochondrial tethering through anti-parallel HR2-HR2 interactions as proposed by Koshiba et al. (4,5). Recently, Cao et al. proposed an alternative model for Mfn1-mediated mitochondrial tethering, in which Mfns oligomerize through GTPase domain dimerization rather than HR2-HR2 intermolecular interactions (6).

Derangements/imbalances in mitochondrial dynamics can lead to neurological and cardiovascular disorders and cancer (1-3). For example, impaired mitochondrial fusion in the untreatable neurological disease Charcot Marie Tooth disease Type 2A (CMT2A), is attributed to a plethora of loss of function mutations in Mfn2 (7). Thus, the development of chemical probes that manipulate fusion/fission may provide a deeper understanding of mitochondrial dynamics and potential therapeutics. Wang et al. reported a chemical probe that induces mitochondrial fusion, but the mechanism of action of this probe is still elusive (8). Yue et al. identified that chemical inhibition of the deubiquitinase USP30 induced fusion (9). Such probe operates via an indirect mechanism and is likely to have an impact on other cellular processes that involve USP30.

The present invention addressed the need for identifying activators of mitofusins for therapeutic treatments.

SUMMARY OF THE INVENTION

The invention provides activators of mitofusins both as single therapeutic agents and in combination with other agents for treatment of diseases and disorders, such as neurological diseases and disorders, cardiovascular disorders, metabolic disorders, cancers, renal, hepatic and bowel ischemia, liver and kidney failure, and autoimmune diseases.

BRIEF DESCRIPTION OF THE DRAWINGS

FIG. 2. Structure-activity relationship of MASM7 scaffold. Potency of MASMs compounds with variable R1, R2, R3 groups were evaluated using WT FRET-based biosensor. HEK 293T cells were treated with MASMs for 2 h.

MFN2 DKO MEFs (left), relative increase of Mito AR in the indicated cells upon MASM7 treatment (right). (H) Mutations on the HR2 domain of the Mfn2 inhibits MASM7-induced fusion. Quantification of Mito AR in MFN1/MFN2 DKO MEFs reconstituted with WT, L727A and D725A/L727A MFN2.

Figure 4A:
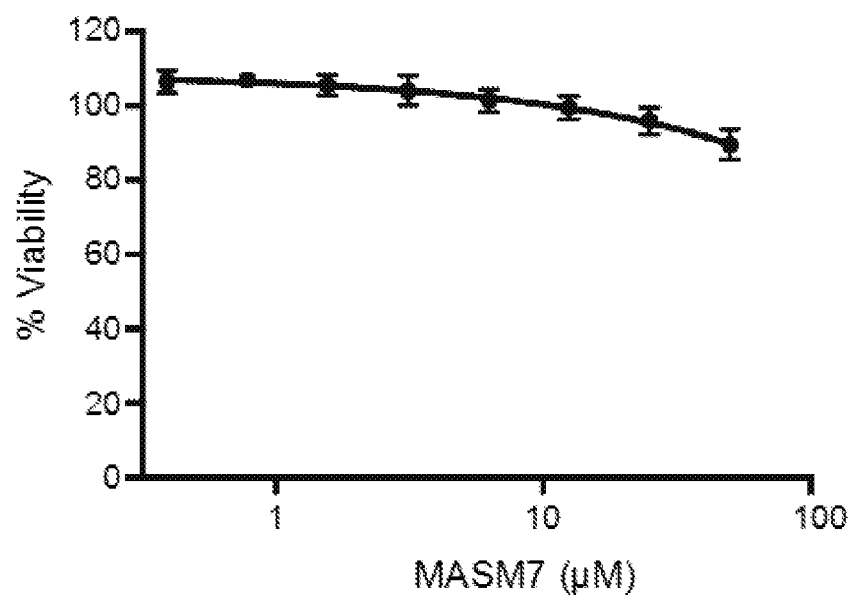
Figure 4C:
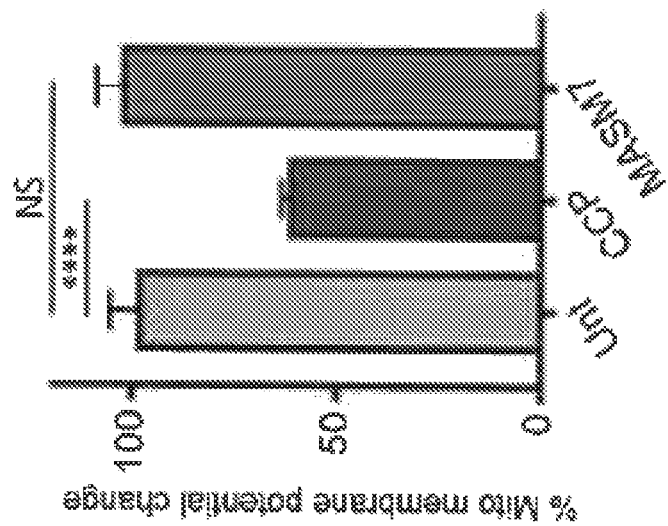
Figure 4B:
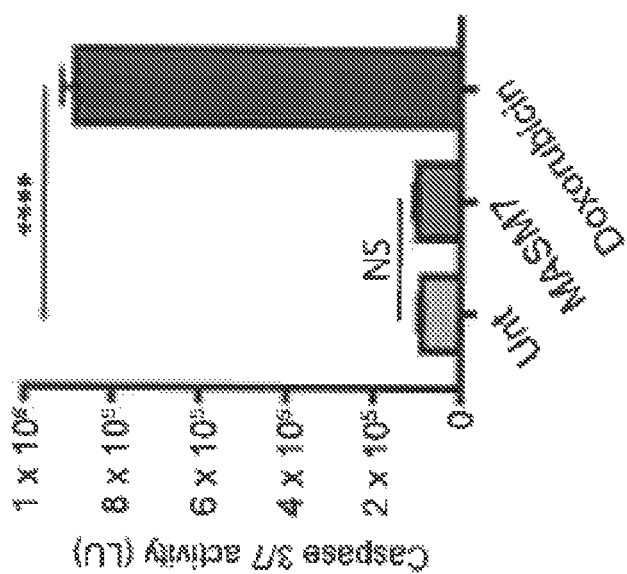
Figure 5A:
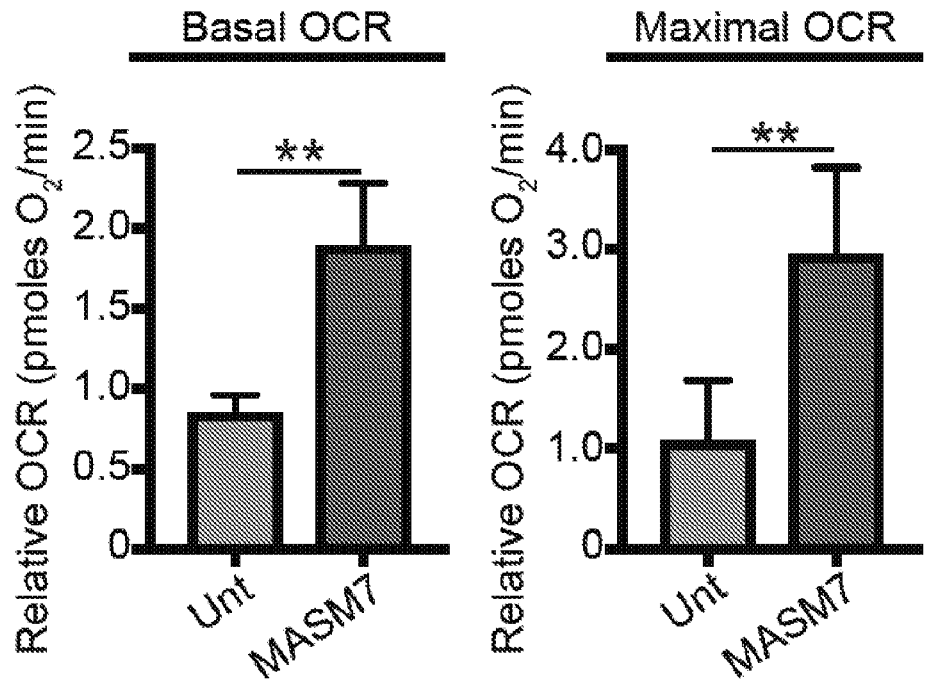
Figure 5B:
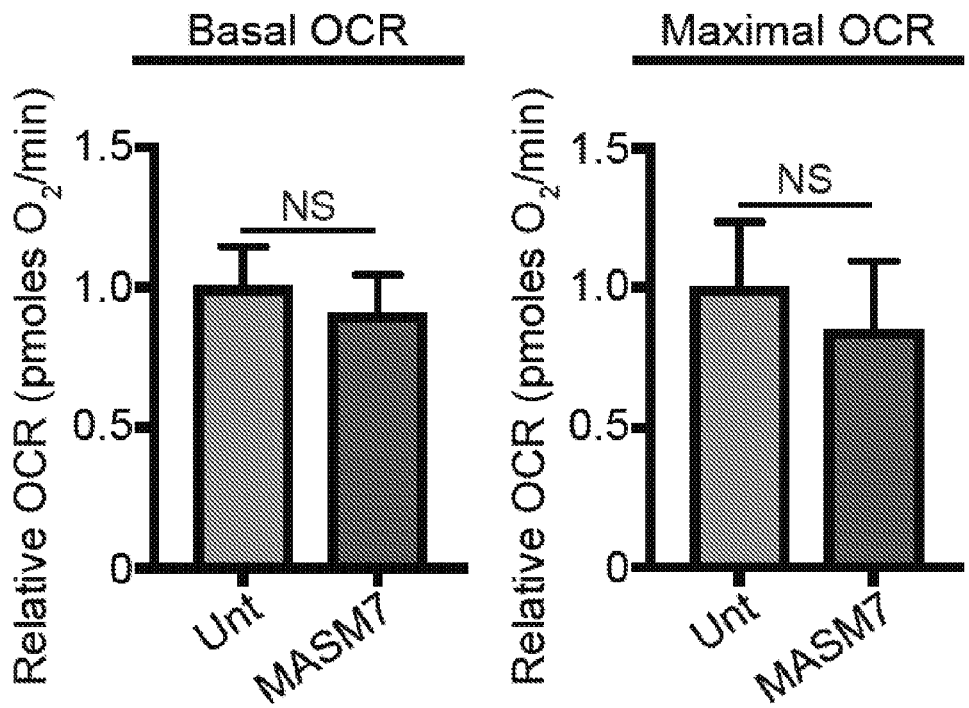
Figure 5C:
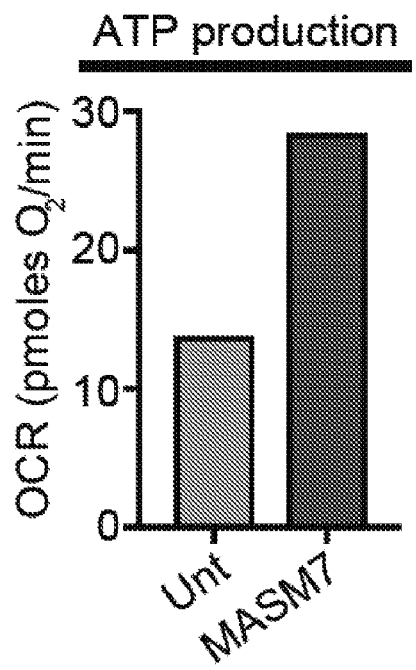
Figure 5D:
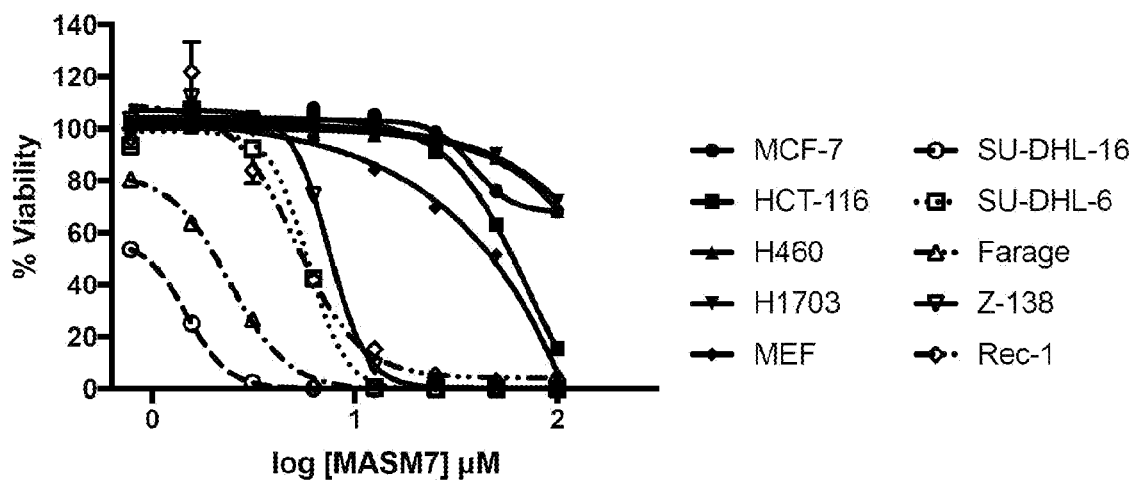
Figure 5E:
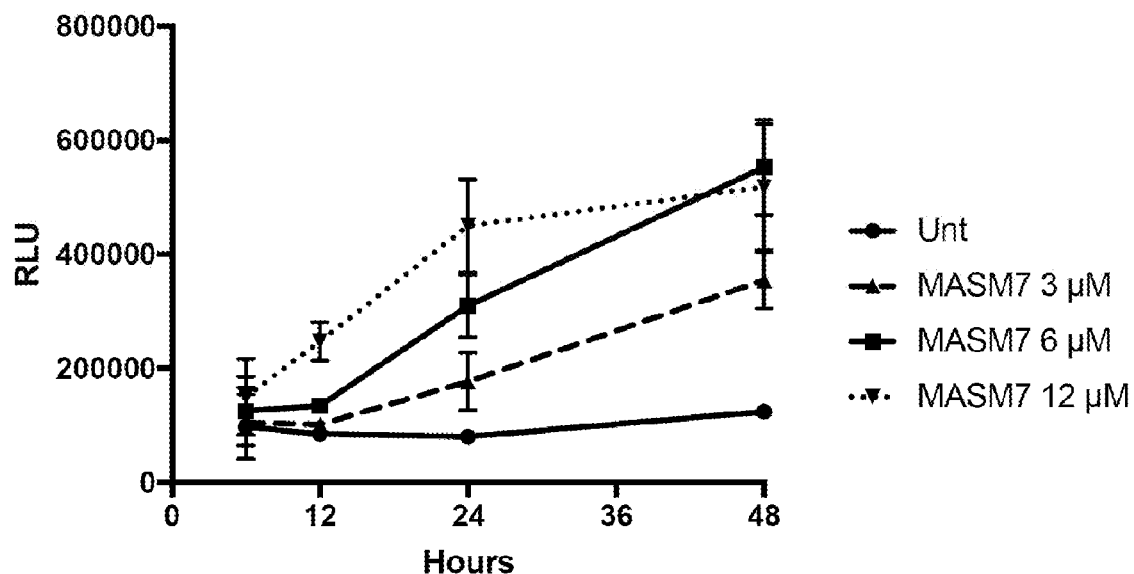
Figure 5F:
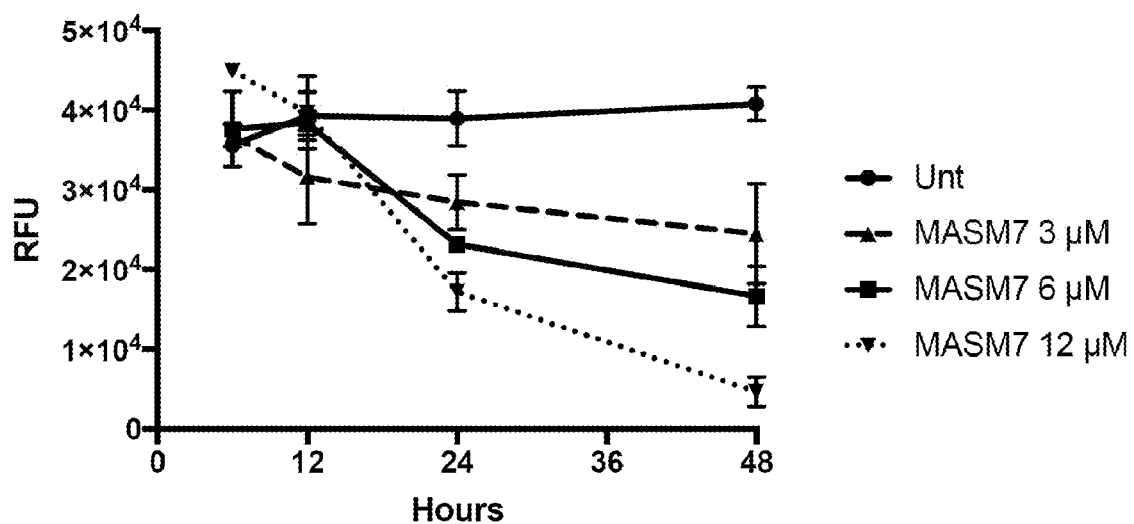
Figure 5G:
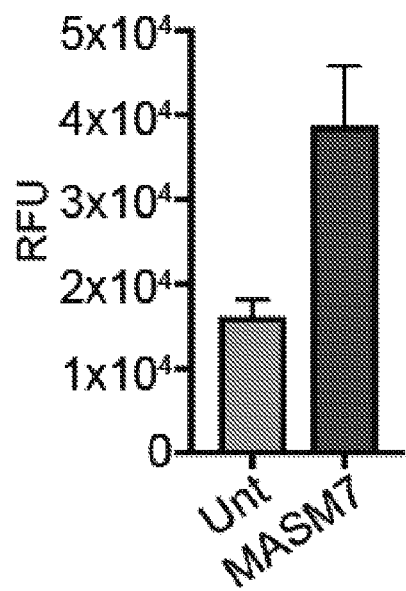
Figure 5H:
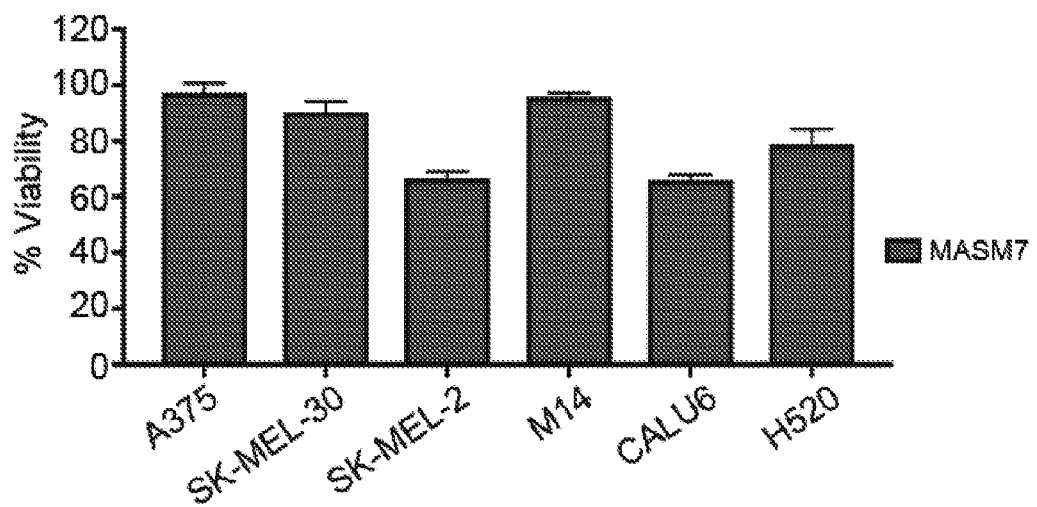

FIG. 4A-4C. MASM7 had no effect on cell growth, reduction of mitochondrial membrane potential or activation of caspase 3/7 in MEFs. (A) Viability assay of MEFs. Cells were treated with MASM7 with the indicated concentrations for 24 h. (B) Caspase 3/7 assay in MEFs. Doxorubicin was used as a positive control. Cells were treated with MASM7 (5 µM, 24 h) or doxorubicin (1 µM, 24 h). (C) TMRE mitochondrial membrane potential assay in MEFs. Cells were treated with MASM7 (5 µM, 24 h) or CCP (20 µM, 40 min). Error bars represent mean±SEM, n=3.

FIG. 5A-5H. (A) MASM7 increases basal and maximal oxygen consumption rate (OCR) in WT MEFs. (B) MASM7 does not increase basal and maximal OCR in MFN1/MFN2 DKO MEFs. (C) MASM7 increases ATP production in WT MEFs. (D) MASM7 reduces viability selectively in lymphoma cells. (E) MASM7 promotes caspase 3 activation in a dose and time dependent manner in Farage cells. (F) MASM7 reduces mitochondrial membrane potential in a dose and time dependent manner in Farage cells. TMRE staining was used as readout. (G) MASM7 increases ROS levels in Farage cells. CellROX was used to evaluate ROS levels. (H) MASM7 display low to moderate toxicity in the indicated cancer cells. Cells were treated with 15 µM of MASM7 for 72 h.

DETAILED DESCRIPTION OF THE INVENTION

The invention provides a method of treating a disease or disorder in a subject, wherein the disease or disorder is selected from the group consisting of a neurological disease or disorder, a cardiovascular disorder, a metabolic disorder, a cancer, renal, hepatic and/or bowel ischemia; liver and/or kidney disease or failure, fatty liver, muscle wasting, acroosteolysis, oxidative stress, anoxia, mitochondrial or DNA damage, and an autoimmune disease, the method comprising administering to the subject one or more compounds of formula (I), (II) or (III) in an amount effective to treat a neurological disease or disorder, a cardiovascular disorder, a metabolic disorder, a cancer, renal, hepatic and/or bowel ischemia; liver and/or kidney disease or failure, fatty liver, muscle wasting, acroosteolysis, oxidative stress, anoxia, mitochondrial or DNA damage, or an autoimmune disease, wherein formula (I) is

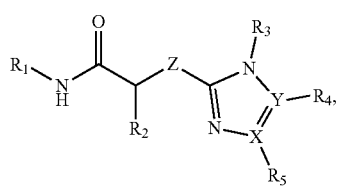

formula (II) is

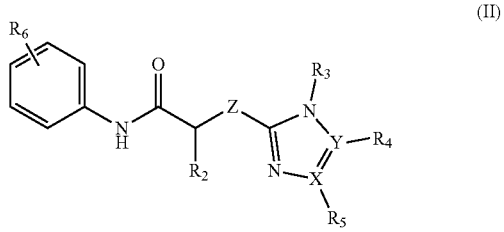

and formula (III) is

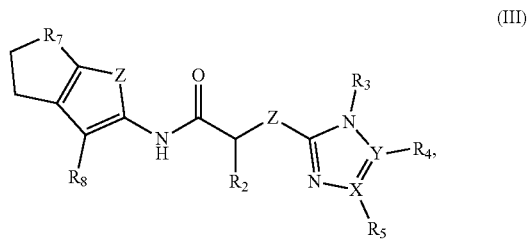

wherein
R1 is aryl, benzyl, heteroaryl, aralkyl, heteroaralkyl, cycloalkyl, heterocycloalkyl, or an optionally substituted aryl, aralkyl, heteroaryl, or heteroaralkyl, wherein the optional substituent is one or more of F, Cl, Br, I, OH, CN, $CH_3$, $NO_2$, SH, COOH, $CF_3$, —CHO, —COOH, amino, $C_1$-$C_6$alkyl, $C_1$-$C_6$haloalkyl, or $C_1$-$C_6$haloalkoxy;
R2 is H, F, Cl, Br, I, OH, $CF_3$, $C_1$-$C_4$ alkyl, $C_1$-$C_4$haloalkyl or $C_1$-$C_4$haloalkoxy;
R3, R4 and R5 are independently H, alkenyl, alkynyl, cycloalkyl, $CH_2CH_3N(CH_3)_2$, heterocycloalkyl, benzyl, aryl, heteroaryl, aralkyl, heteroaralkyl, or optionally substituted aryl, aralkyl, heteroaryl, or heteroaralkyl, wherein the optional substituent is one or more of F, Cl, Br, I, OH, $CH_3$, CN, $NO_2$, SH, COOH or $CF_3$;
R6 is H, CN, $CONH_2$, COOH, COOR9, F, Cl, Br, I, OH, $CH_3$, $NO_2$, $CF_3$, $C_1$-$C_6$ alkyl, $C_1$-$C_6$haloalkyl or $C_1$-$C_6$haloalkoxy;
R7 is $CH_2$, $CH_2CH_2$, $CH_2CH_2CH_2$ or $CH_2CH_2CH_3$;
R8 is CN, $CONH_2$, COOH or COOR9;
R9 is $C_1$-$C_4$ alkyl or $C_1$-$C_4$haloalkyl;
X and Y are independently N or CH;
Z is S, O, NH, $CH_2$, C=O, $SO_2$, NR or CHR10;
R10 is $C_1$-$C_4$ alkyl, $C_1$-$C_4$haloalkyl or $C_1$-$C_4$ haloalkoxy;
or a pharmaceutically acceptable salt, ester or prodrug thereof.

The invention also provides a method of treating a disease or disorder in a subject, wherein the disease or disorder is selected from the group consisting of a neurological disease or disorder, a cardiovascular disorder, a metabolic disorder, a cancer, renal, hepatic and/or bowel ischemia; liver and/or kidney disease or failure, fatty liver, muscle wasting, acroosteolysis, oxidative stress, anoxia, mitochondrial or DNA damage, and an autoimmune disease, the method comprising administering to the subject one or more of the following compounds in an amount effective to treat a neurological disease or disorder, a cardiovascular disorder, a metabolic disorder, a cancer, renal, hepatic and/or bowel ischemia;

liver and/or kidney disease or failure, fatty liver, muscle wasting, acroosteolysis, oxidative stress, anoxia, mitochondrial or DNA damage, or an autoimmune disease:
MASM1
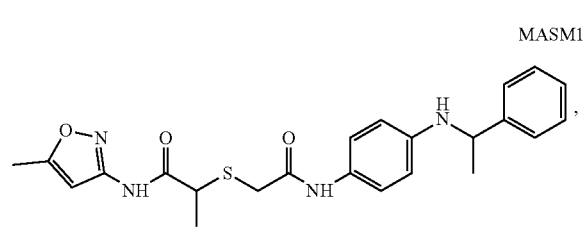
MASM2
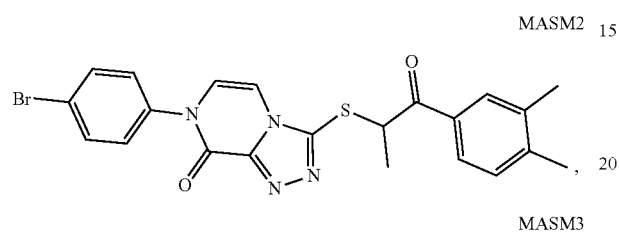
MASM3
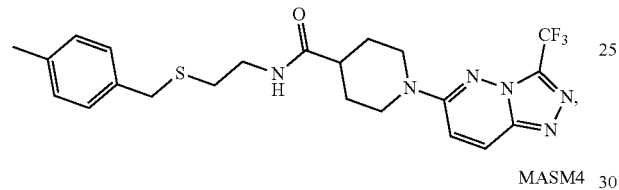
MASM4
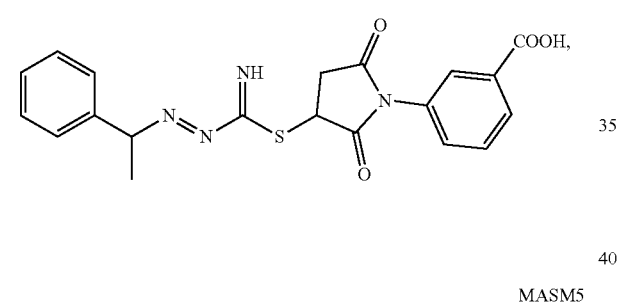
MASM5
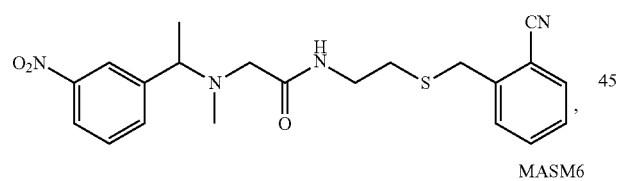
MASM6
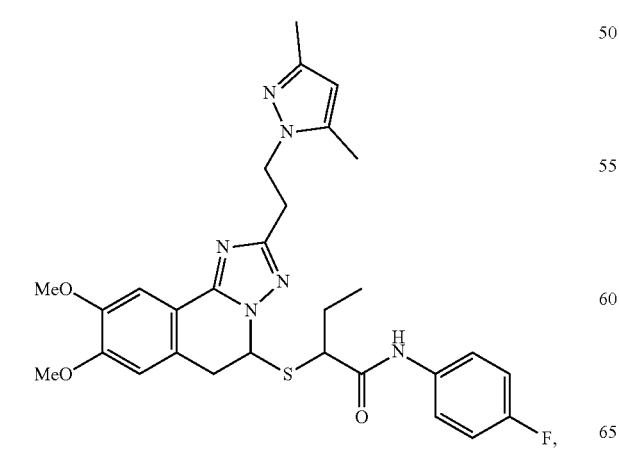
-continued
MASM7
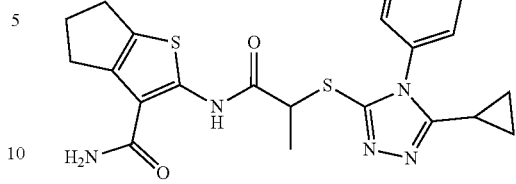
MASM8
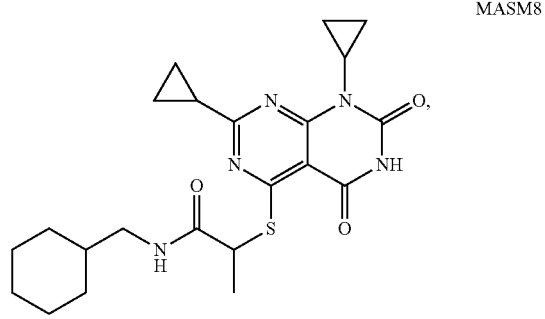
MASM9
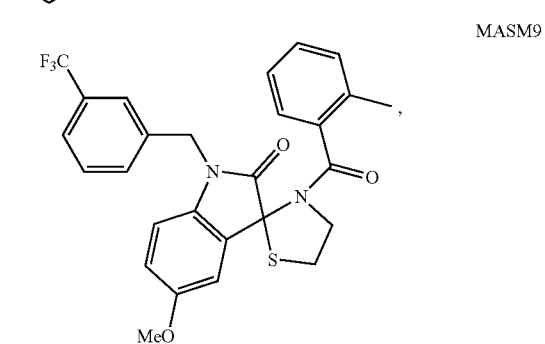
MASM10
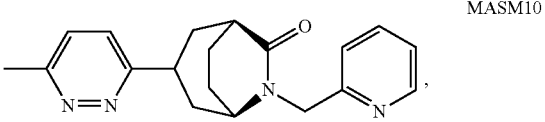
MASM11
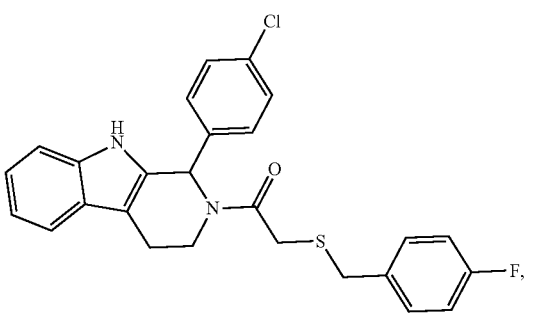
MASM12
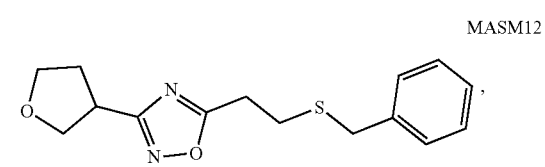

MASM13
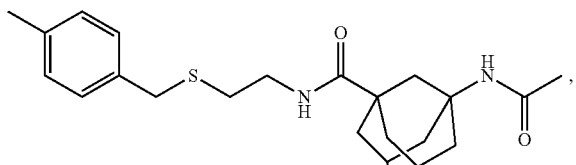
MASM14
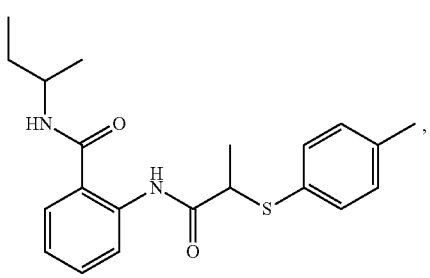
MASM15
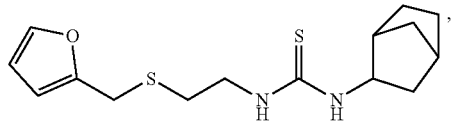
MASM16
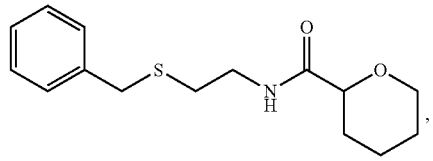
MASM17
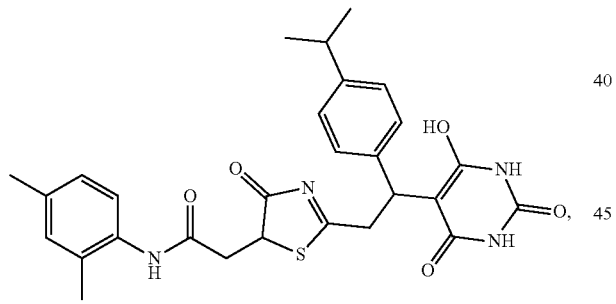
MASM18
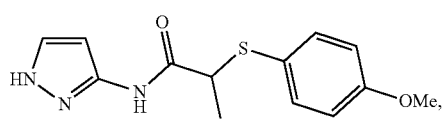
MASM19
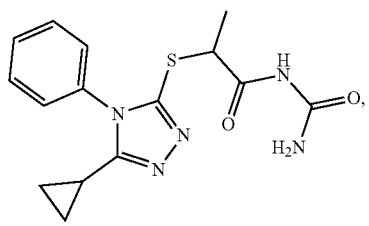
MASM20
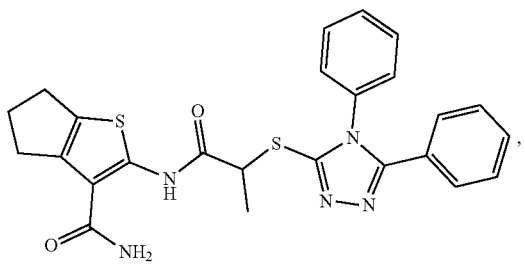
MASM21
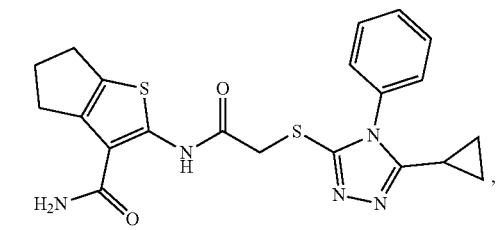
MASM22
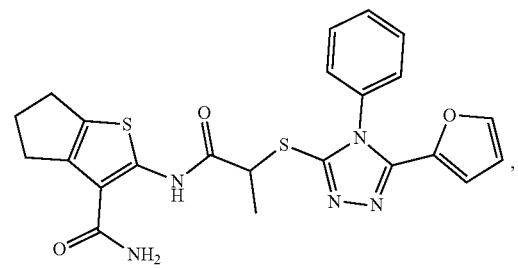
MASM23
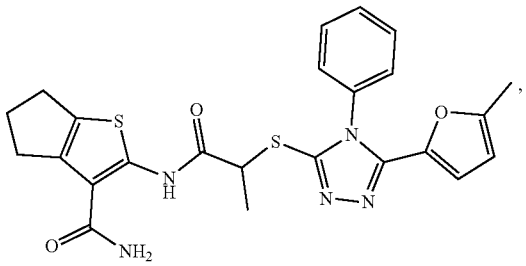
MASM24
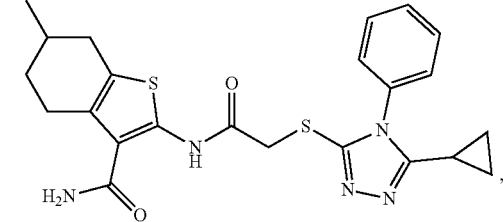

MASM25
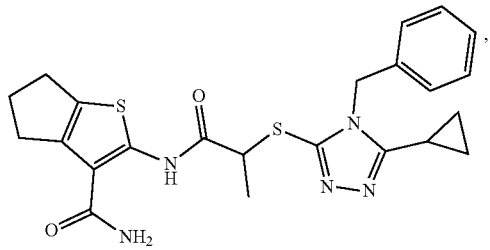
MASM26
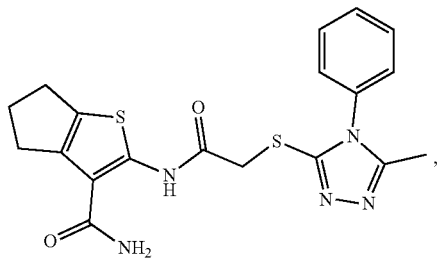
MASM27
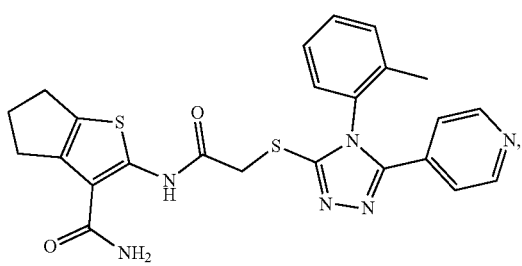
MASM28
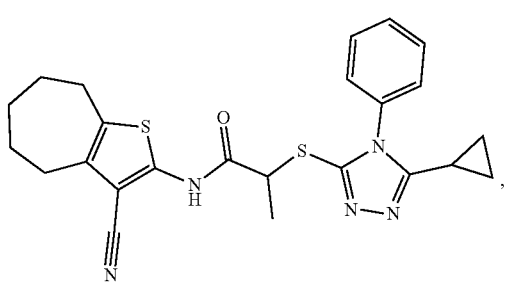
MASM29
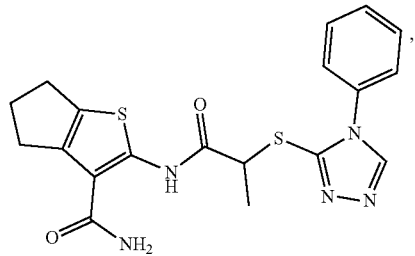
MASM30
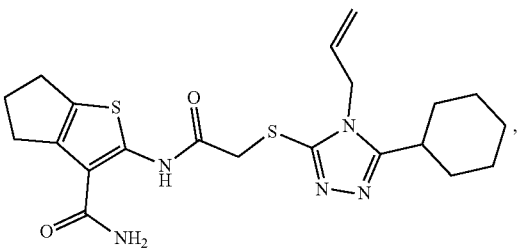
MASM31
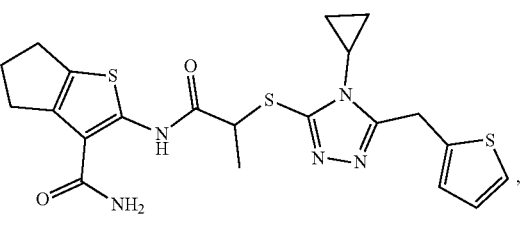
MASM32
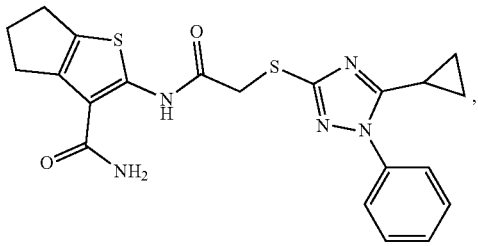
MASM33
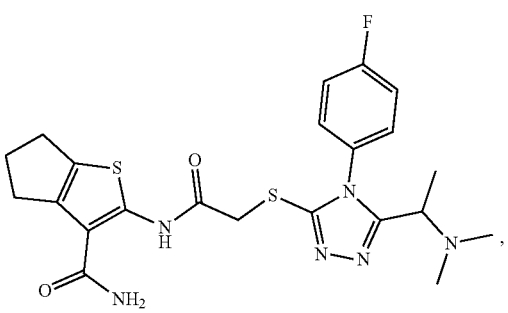
MASM34
MASM35
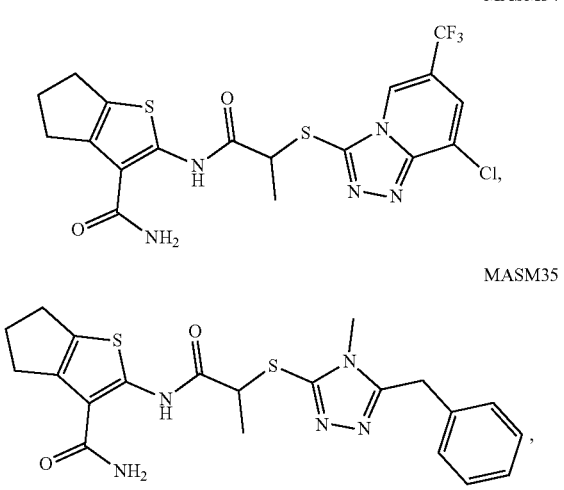

MASM36
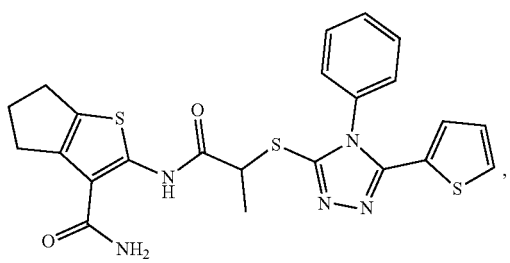
MASM37
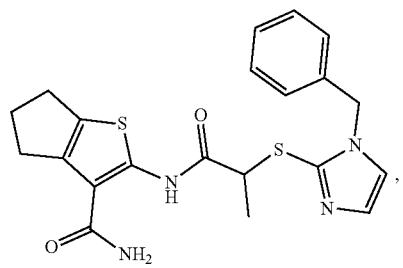
MASM38
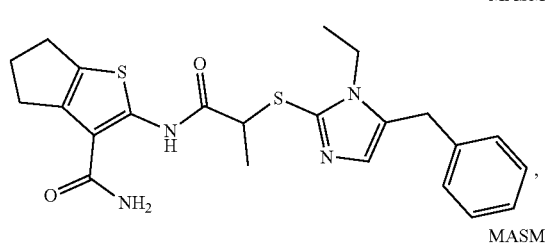
MASM39
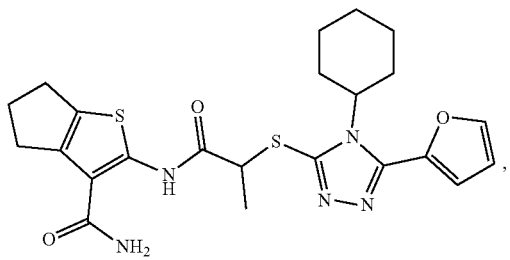
MASM40
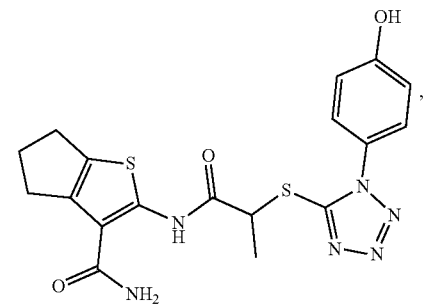
MASM41
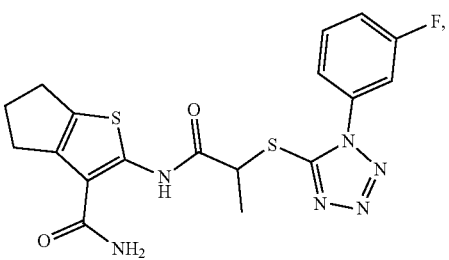
MASM42
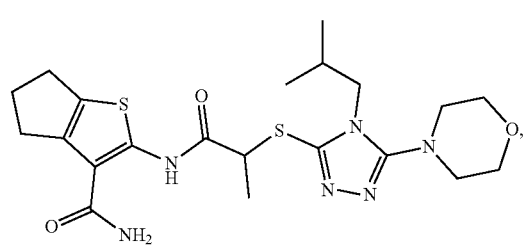
MASM43
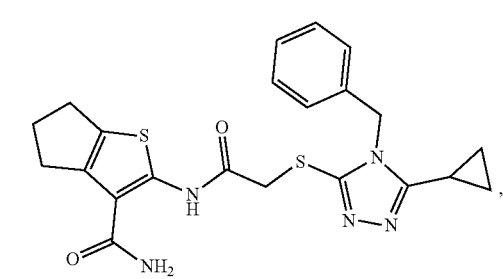
MASM44
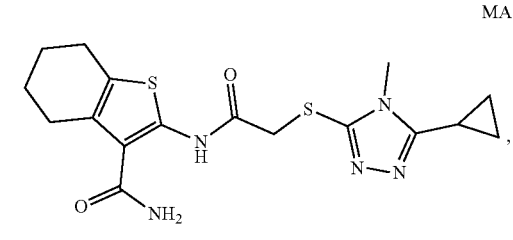
MASM45
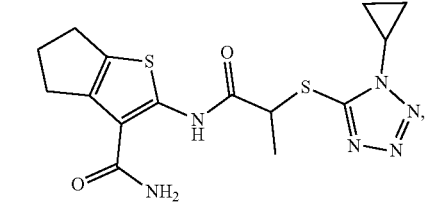
B09
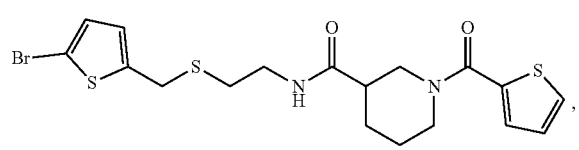
D08
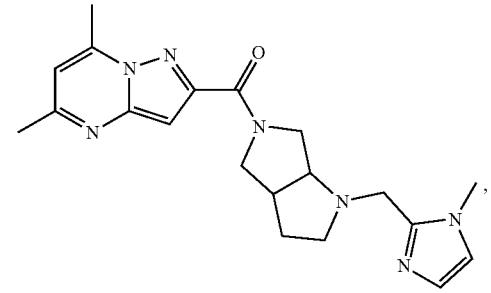

D02
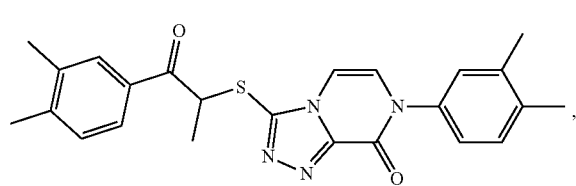
C02
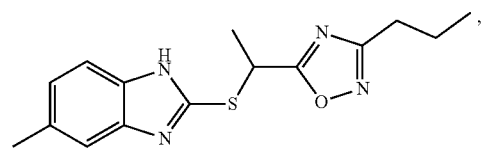
C10
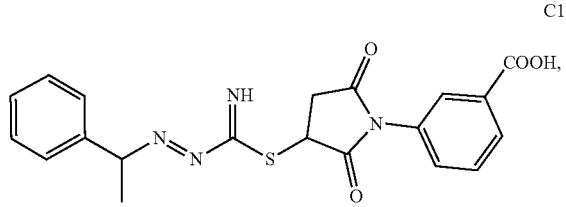
D01
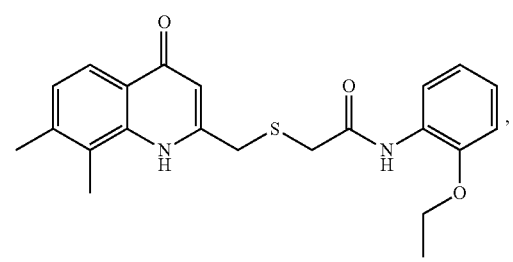
C01
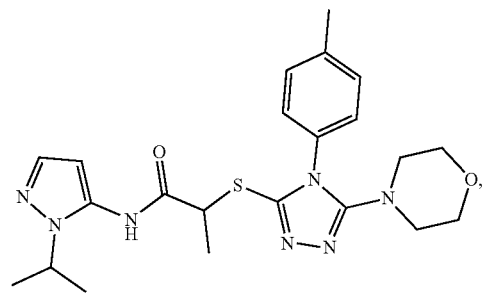
B03
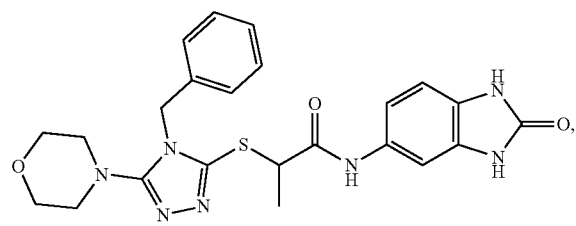
A03
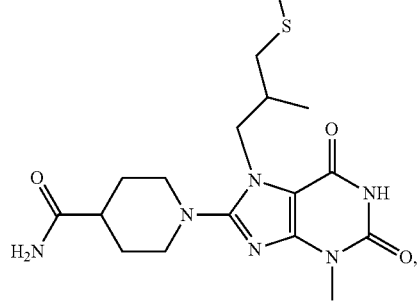
B09
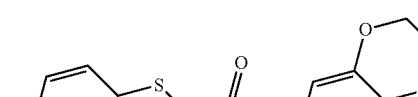
A05
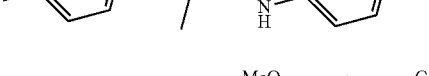
E01
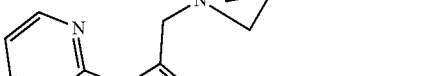
D11
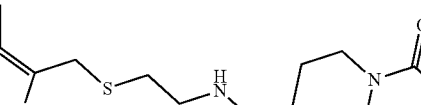
A01
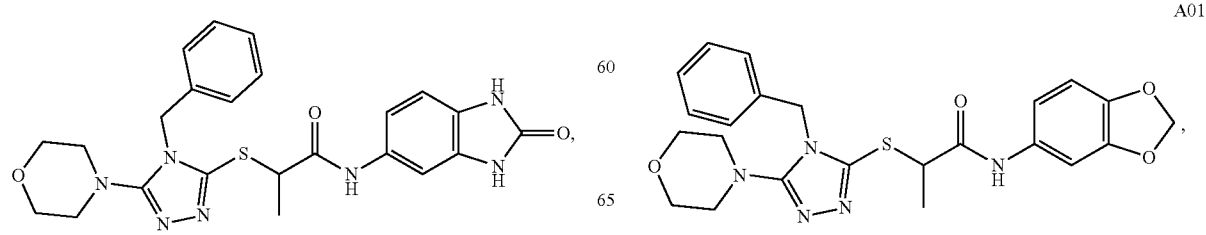

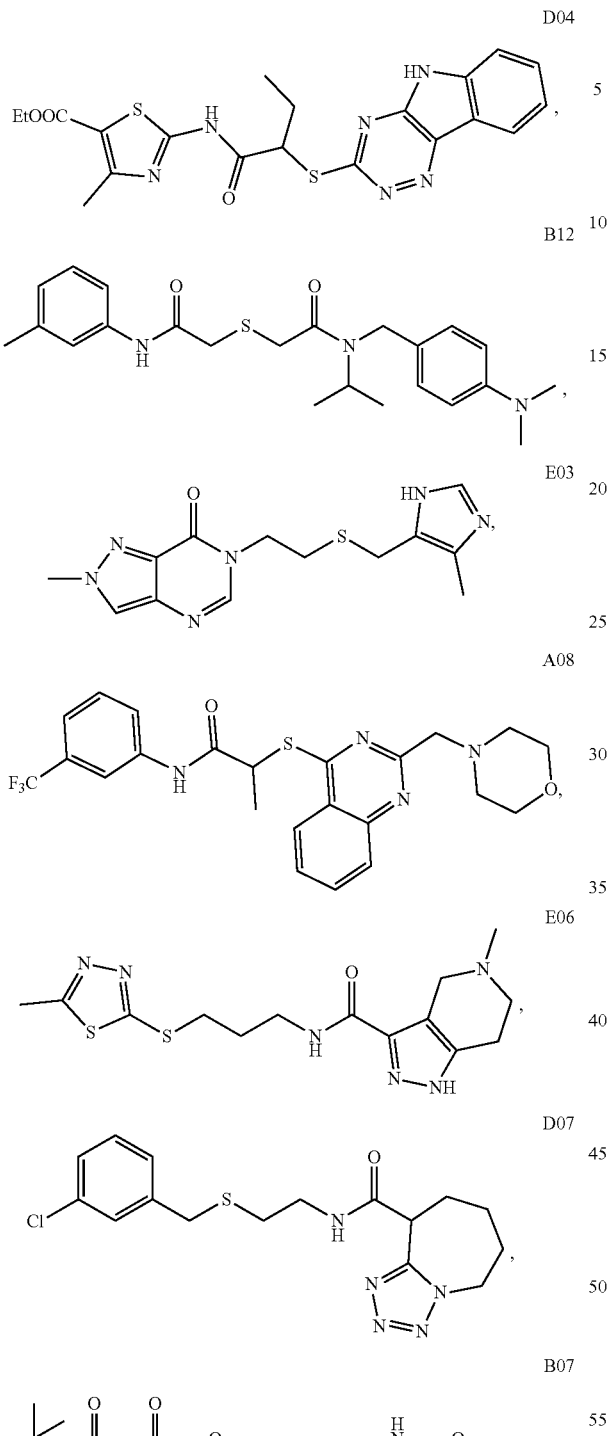
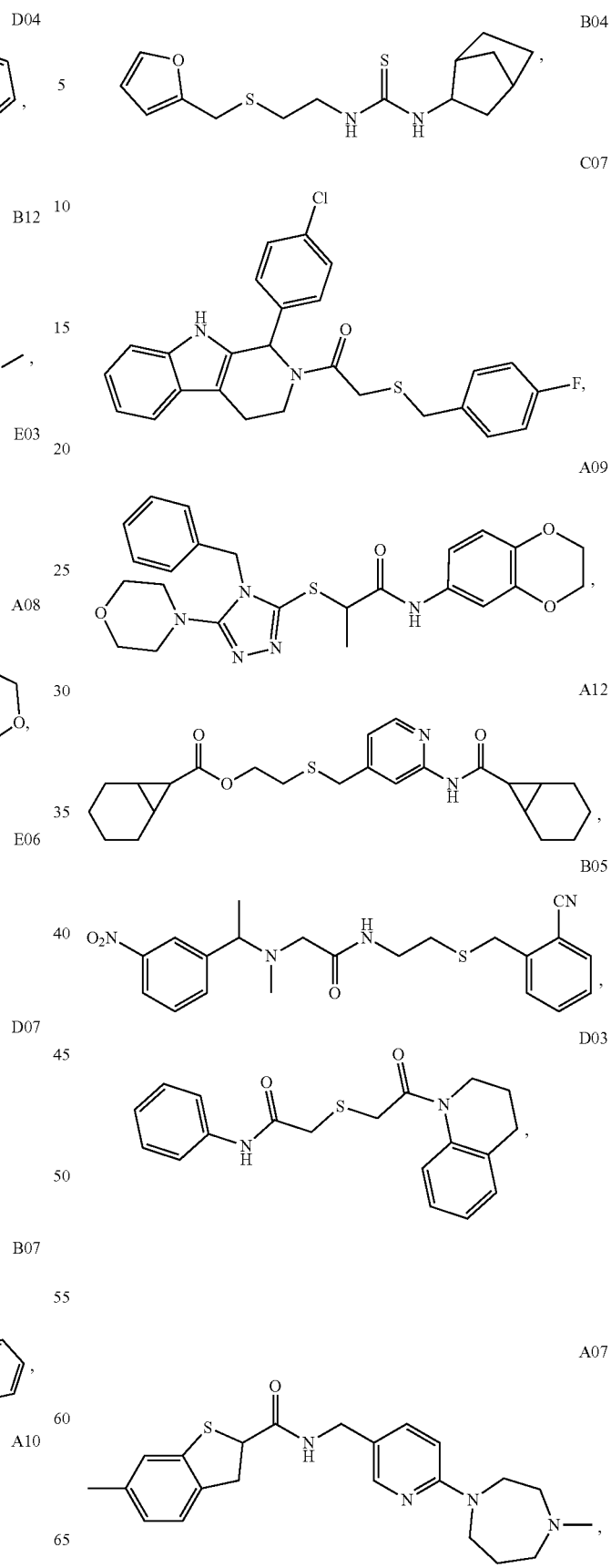

-continued

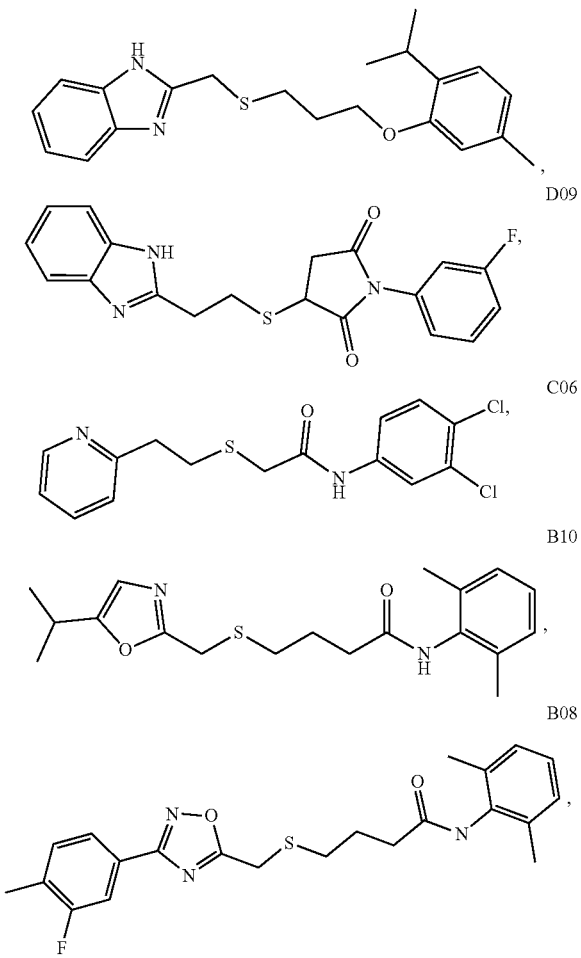

or a pharmaceutically acceptable salt, ester or prodrug thereof.

Preferably, the compound activates mitofusins, i.e., Mfn1 and/or Mfn2.

The neurological disease or disorder can be, for example, Charcot Marie Tooth disease Type 2A or Type 3, Alzheimer's Disease, dementia, frontotemporal dementia, Parkinson's Disease, Huntington's Disease, cognitive impairment, prion diseases, amyotrophic lateral sclerosis, ataxia, a peripheral nervous system disorder, axonal neuropathy, a demyelinating disease, a neurodegenerative disorder, or atrophy of an optic nerve or disc.

The cardiovascular disorder can be, for example, a myocardial infarction, heart failure, cardiomyopathy, coronary heart disease, a cerebrovascular accident, hypertensive vascular disease, arteriosclerosis, reperfusion injury, or stroke.

The metabolic disorder can be, for example, diabetes type I or II, insulin resistance, hyperglycemia, obesity or a metabolic disorder.

The muscle wasting can be, for example, a myopathy or amyotrophy.

The cancer can be, for example, a leukemia or a solid tumor. The cancer can be, for example, acute lymphoblastic leukemia (ALL), acute myeloid leukemia (AML), chronic lymphocytic leukemia (CLL) or chronic myeloid leukemia (CML). The cancer can be, for example, breast cancer, prostate cancer, lymphoma, skin cancer, pancreatic cancer, colon cancer, melanoma, malignant melanoma, ovarian cancer, brain or spinal cord cancer, primary brain carcinoma, medulloblastoma, neuroblastoma, glioma, head-neck cancer, glioma, glioblastoma, liver cancer, bladder cancer, stomach cancer, kidney cancer, placental cancer, cancer of the gastrointestinal tract, non-small cell lung cancer (NSCLC), head or neck carcinoma, breast carcinoma, endocrine cancer, eye cancer, genitourinary cancer, cancer of the vulva, ovary, uterus or cervix, hematopoietic cancer, myeloma, leukemia, lymphoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft tissue cancer, soft-tissue sarcoma, osteogenic sarcoma, sarcoma, primary macroglobulinemia, central nervous system cancer, retinoblastoma, or metastatic cancer.

The invention also provides a pharmaceutical composition comprising a pharmaceutically acceptable carrier and one or more compounds of formula (I), (II) or (III), wherein formula (I) is

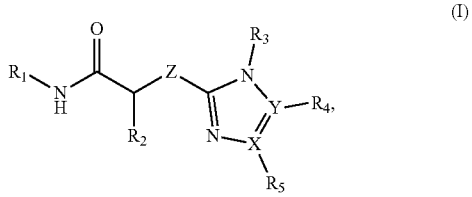

formula (II) is

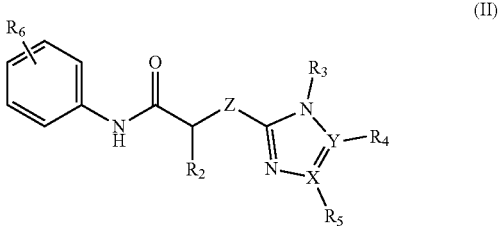

and formula (III) is

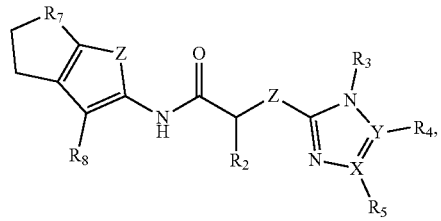

wherein
R1 is aryl, benzyl, heteroaryl, aralkyl, heteroaralkyl, cycloalkyl, heterocycloalkyl, or an optionally substituted aryl, aralkyl, heteroaryl, or heteroaralkyl, wherein the optional substituent is one or more of F, Cl, Br, I, OH, CN, $CH_3$, $NO_2$, SH, COOH, $CF_3$—CHO, —COOH, amino, $C_1$-$C_6$alkyl, $C_1$-$C_6$haloalkyl, or $C_1$-$C_6$haloalkoxy;

R2 is H, F, Cl, Br, I, OH, $CF_3$, $C_1$-$C_4$ alkyl, $C_1$-$C_4$haloalkyl or $C_1$-$C_4$haloalkoxy;

R3, R4 and R5 are independently H, alkenyl, alkynyl, cycloalkyl, $CH_2CH_3N(CH_3)_2$, heterocycloalkyl, benzyl, aryl, heteroaryl, aralkyl, heteroaralkyl, or optionally substituted aryl, aralkyl, heteroaryl, or heteroaralkyl, wherein the optional substituent is one or more of F, Cl, Br, I, OH, $CH_3$, CN, $NO_2$, SH, COOH or $CF_3$;

R6 is H, CN, $CONH_2$, COOH, COOR9, F, Cl, Br, I, OH, $CH_3$, $NO_2$, $CF_3$, $C_1$-$C_6$ alkyl, $C_1$-$C_6$haloalkyl or $C_1$-$C_6$haloalkoxy;

R7 is $CH_2$, $CH_2CH_2$, $CH_2CH_2CH_2$ or $CH_2CH_2CH_3$;

R8 is CN, $CONH_2$, COOH or COOR9;

R9 is $C_1$-$C_4$ alkyl or $C_1$-$C_4$haloalkyl;

X and Y are independently N or CH;

Z is S, O, NH, $CH_2$, C=O, $SO_2$, NR or CHR10;

R10 is $C_1$-$C_4$ alkyl, $C_1$-$C_4$haloalkyl or $C_1$-$C_4$ haloalkoxy;

or a pharmaceutically acceptable salt, ester or prodrug thereof.

The invention further provides a pharmaceutical composition comprising a pharmaceutically acceptable carrier and one or more compounds selected from the group consisting of:

MASM1

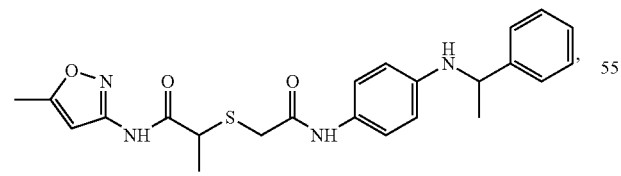

MASM2

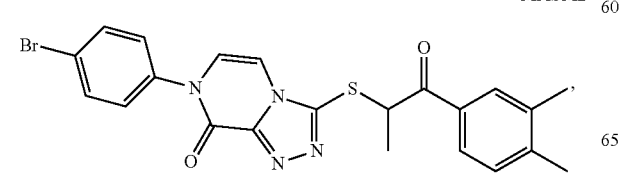

MASM3

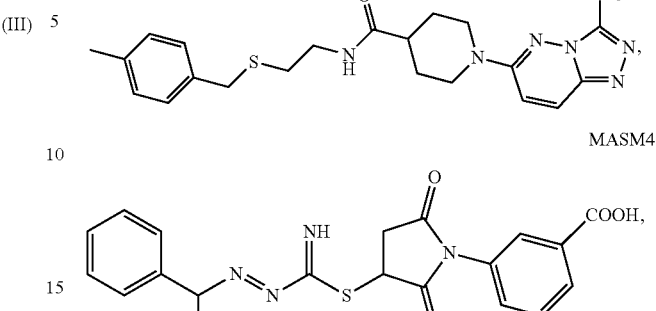

MASM4

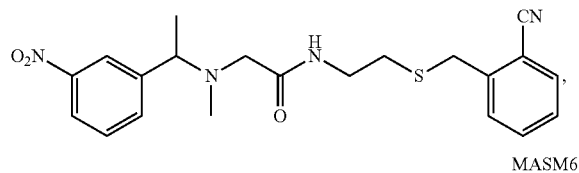

MASM5

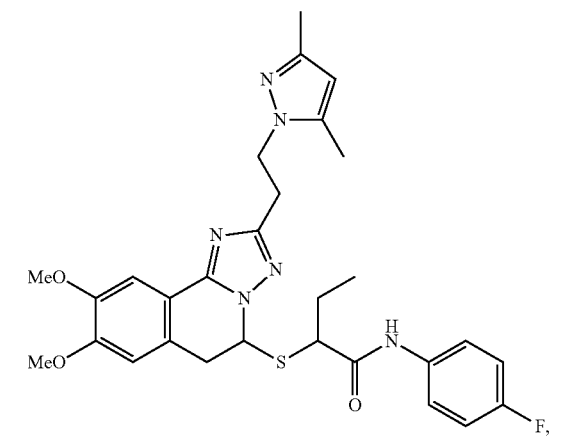

MASM6

MASM7

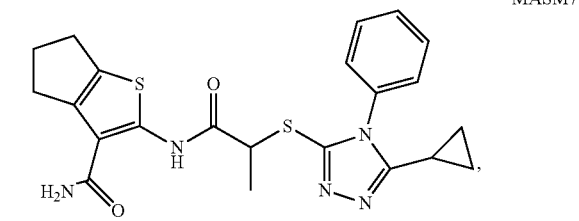

MASM8

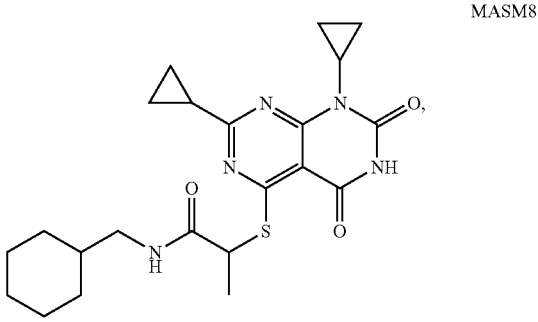

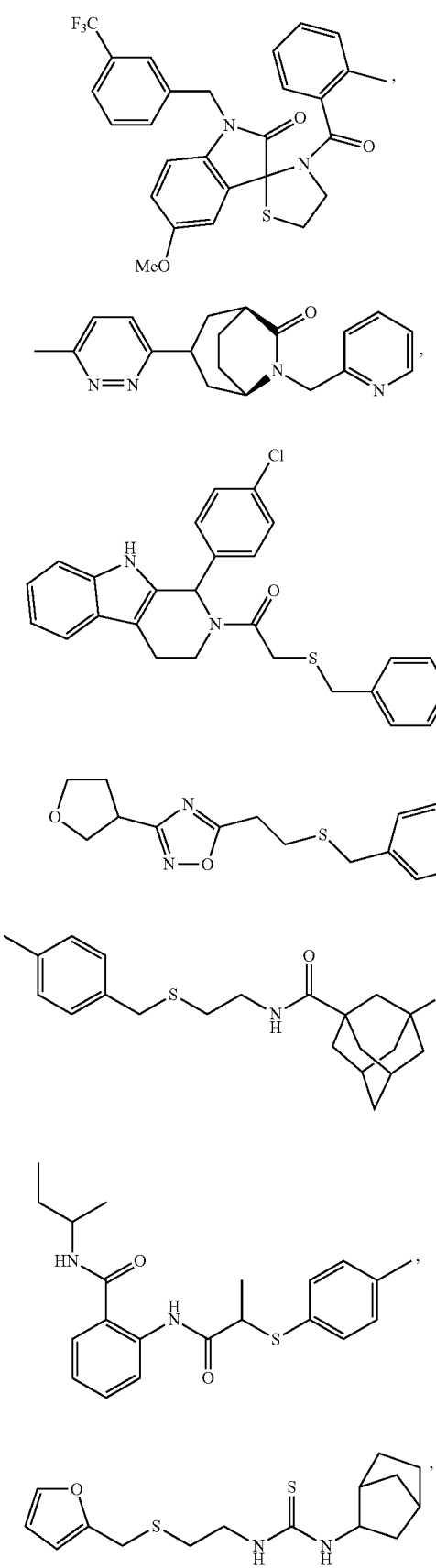

MASM23
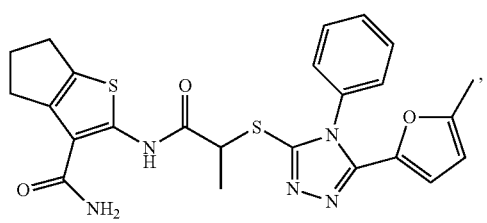
MASM24
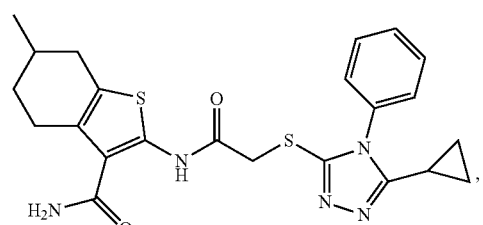
MASM25
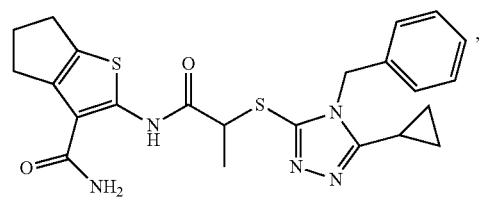
MASM26
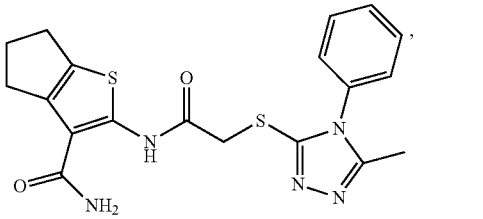
MASM27
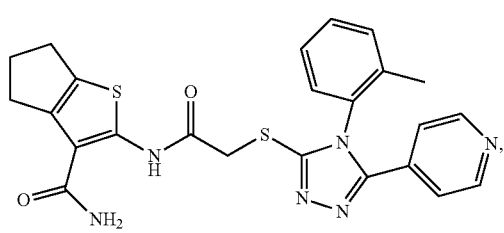
MASM28
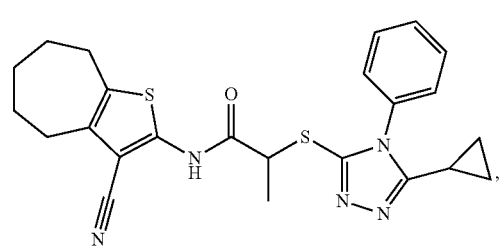
MASM29
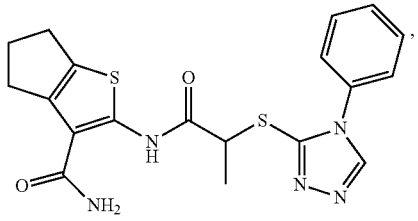
MASM30
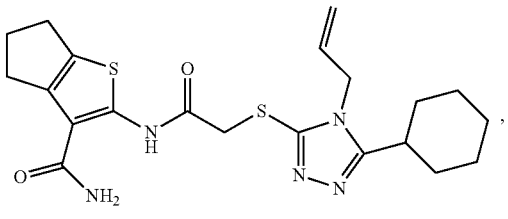
MASM31
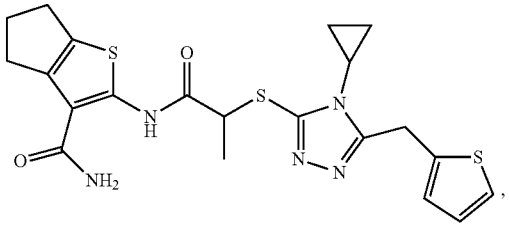
MASM32
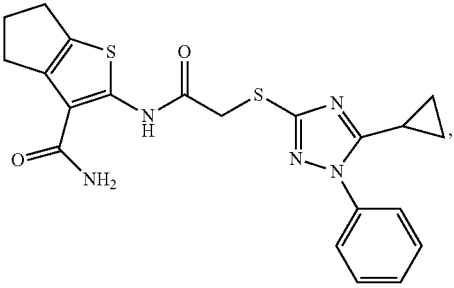
MASM33
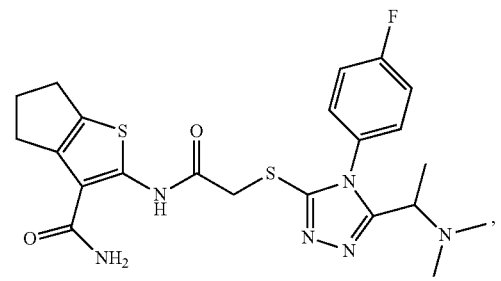
MASM34
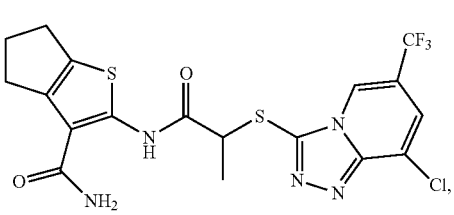

MASM35
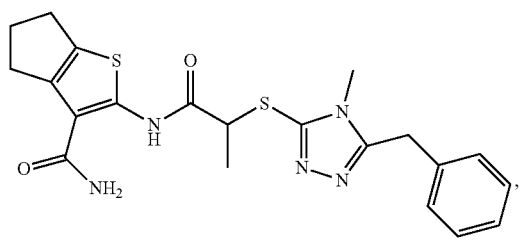
MASM36
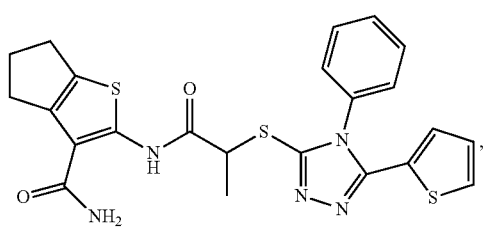
MASM37
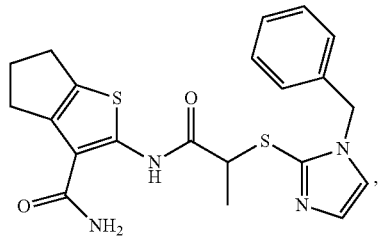
MASM38
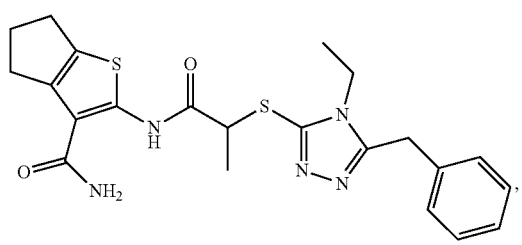
MASM39
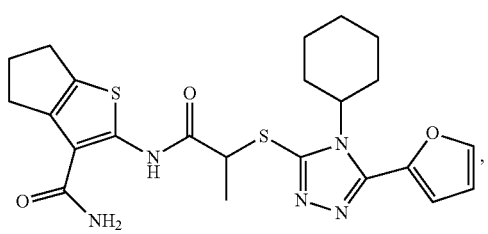
MASM40
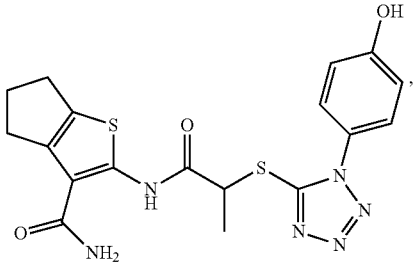
MASM41
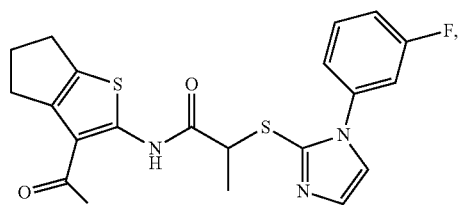
MASM42
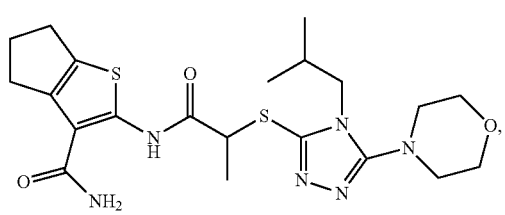
MASM43
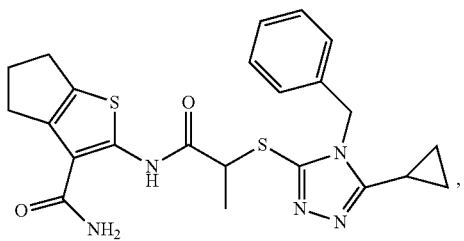
MASM44
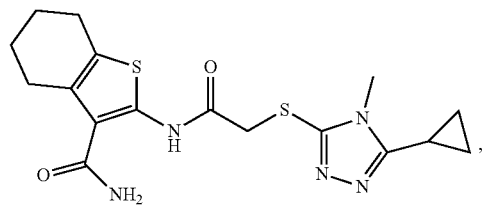
MASM45
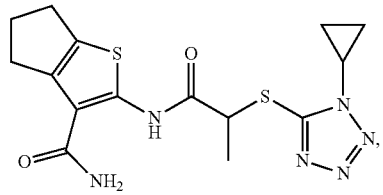
B09
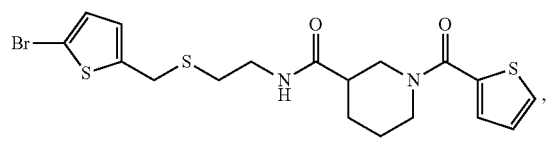

D08
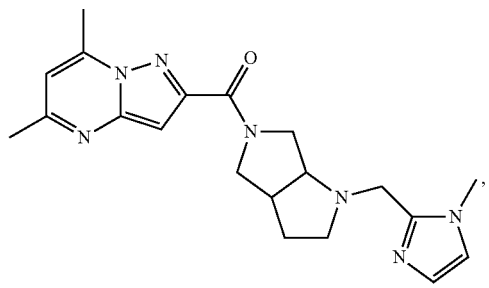
D02
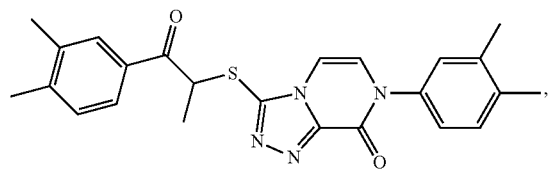
C02
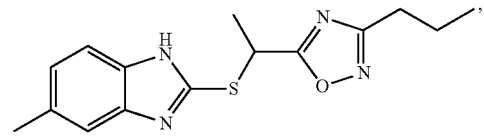
C10
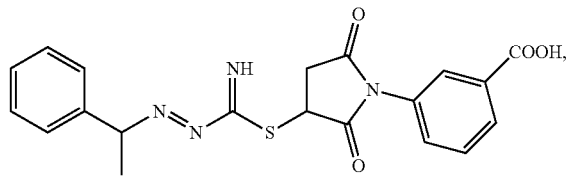
D01
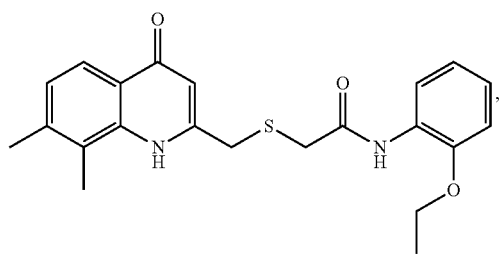
C01
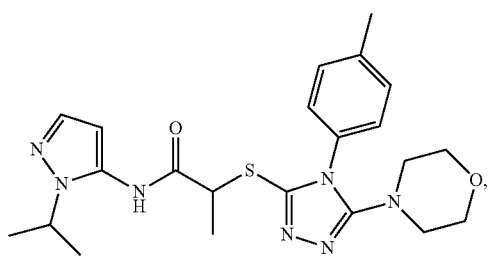
B03
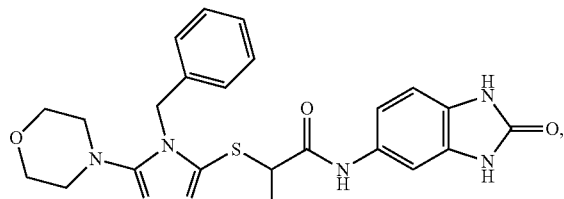
A03
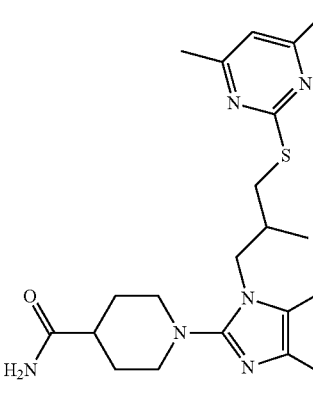
B09
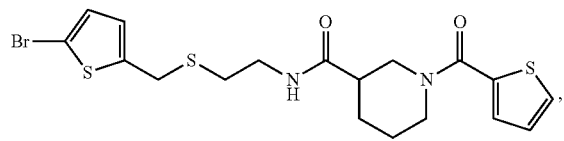
A05
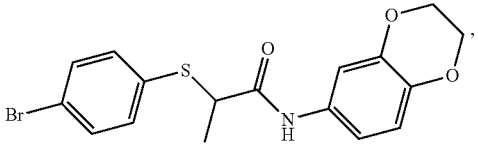
E01
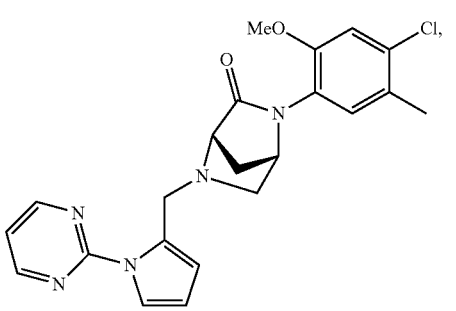
D11
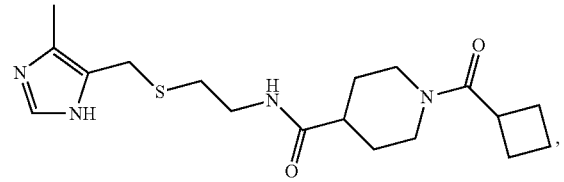

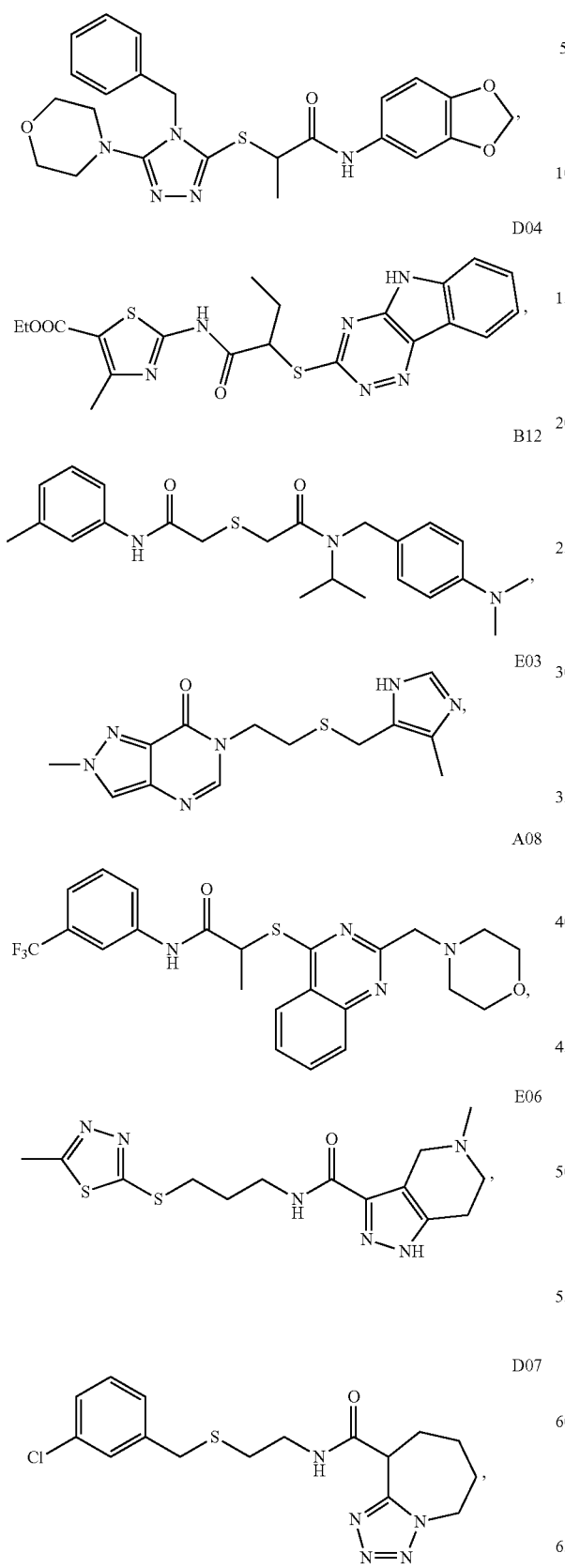
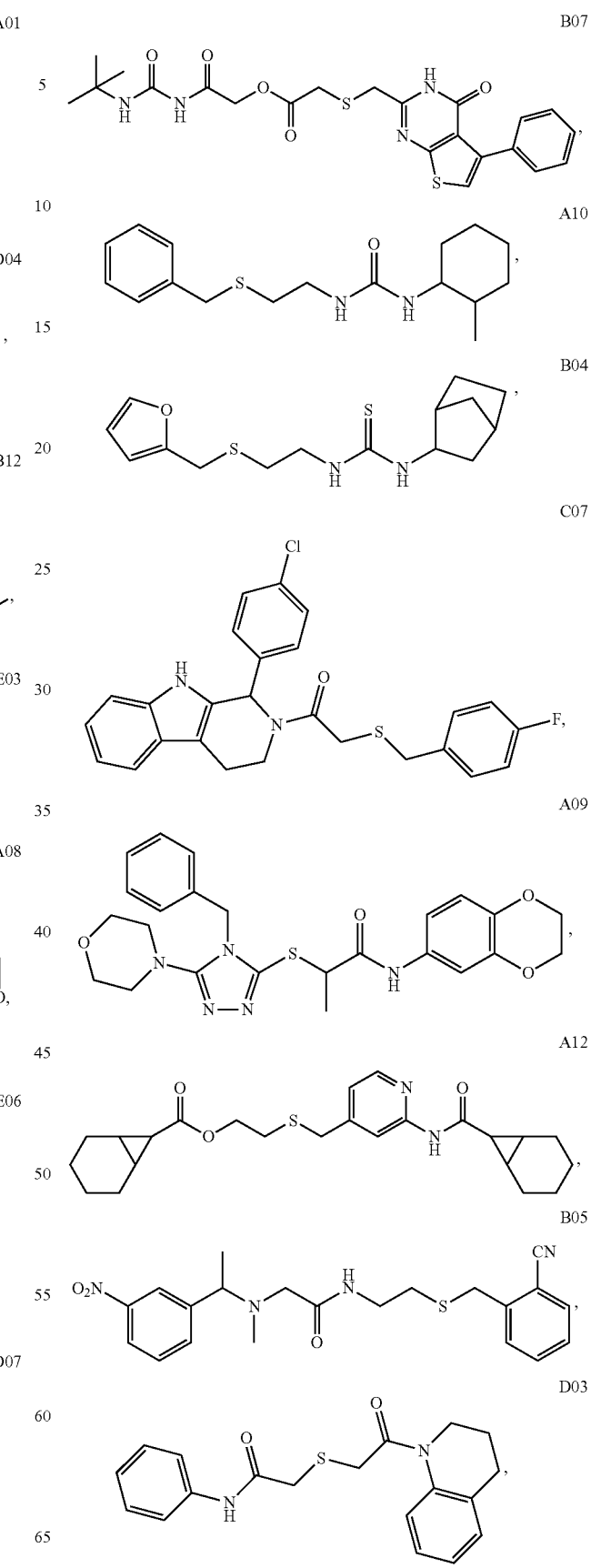

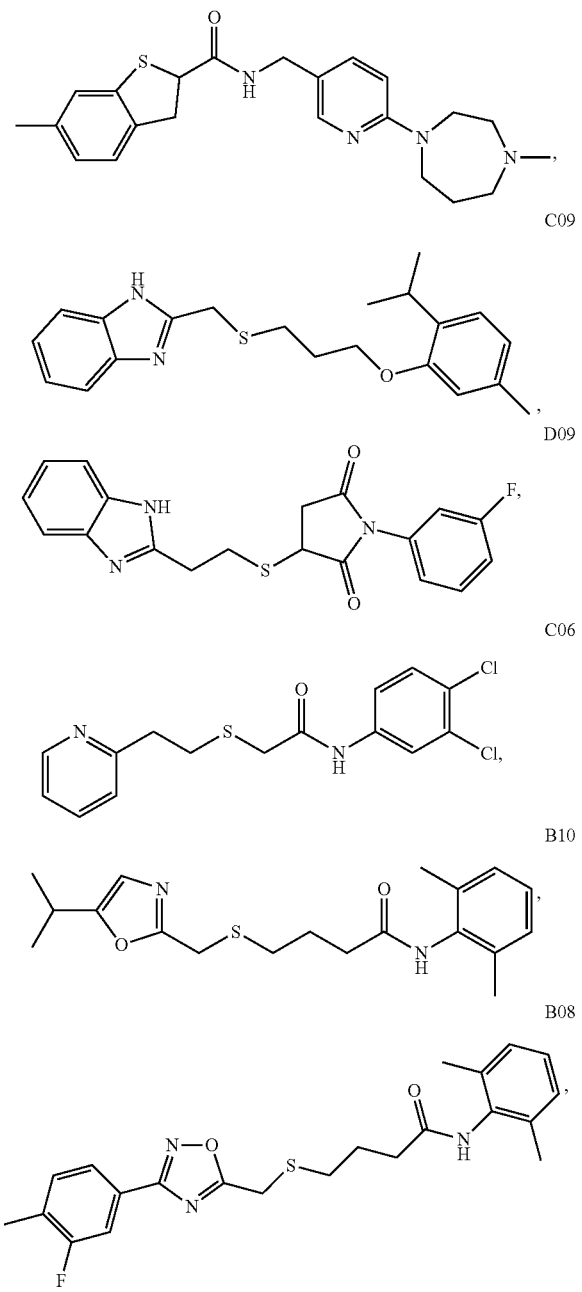

or a pharmaceutically acceptable salt, ester or prodrug thereof.

Preferably, the compound is present in the composition in an amount effective to activate mitofusins, i.e., Mfn1 and/or Mfn2.

Pharmaceutically acceptable salts that can be used with compounds of the present invention are non-toxic salts derived, for example, from inorganic or organic acids including, but not limited to, salts derived from hydrochloric, sulfuric, phosphoric, acetic, lactic, fumaric, succinic, tartaric, gluconic, citric, methanesulphonic and p-toluenesulphonic acids.

Esters of the compounds can include, for example, an alkyl ester (e.g., $C_1$-$C_3$ alkyl, or $C_3$-$C_6$ alkyl, or $C_3$-$C_6$ branched alkyl, e.g., t-butyl, isopropyl, isobutyl), ester groups derived from aliphatic carboxylic acids, formates, acetates, propionates, butyrates, acrylates and ethylsuccinates.

Prodrugs of the compounds can include, for example, mono-, di-, or triphosphate prodrugs, peptidyl derivatives, succinates, phosphate esters, acetates, and carbonyl groups, carbamate prodrugs, and carbonate prodrugs. Various forms of prodrugs are known in the art. See, for Bundgaard, (ed.), Design of Prodrugs, Elsevier (1985), Krogsgaard-Larsen, et al., (ed). Design and Application of Prodrugs, Textbook of Drug Design and Development (1991); and Higuchi and Stella (eds.) Prodrugs as Novel Drug Delivery Systems, American Chemical Society (1975), the contents of which are herein incorporated by reference.

The term "pharmaceutically acceptable carrier" is used in accordance with its art-understood meaning, to refer to a material that is included in a pharmaceutical composition but does not abrogate the biological activity of pharmaceutically active agent(s) that are also included within the composition. Typically, carriers have very low toxicity to the animal to which such compositions are to be administered. In some embodiments, carriers are inert. Pharmaceutically acceptable carriers and diluents that can be used herewith encompasses any of the standard pharmaceutical carriers or diluents, such as, for example, a sterile isotonic saline, phosphate buffered saline solution, water, and emulsions, such as an oil/water or water/oil emulsions.

Also provided is a medicament for treating a disease or disorder comprising any of the compounds disclosed herein or any of the pharmaceutical compositions disclosed herein, wherein the compound is in an amount effective to activate Mfn2.

Also provided is a method of treating a disease or disorder in a subject comprising administering to the subject any of the compounds disclosed herein in an amount effective to activate Mfn2 in a subject.

As used herein, to "treat" or "treating" a disease or disorder means to reduce or eliminate a sign or symptom of the disease or disorder in a subject. For example, for cancer, reducing the further spread of cancer in the subject. In terms of tumors, "treat" a tumor means to eradicate the tumor, to reduce the size of the tumor, to stabilize the tumor so that it does not increase in size, or to reduce the further growth of the tumor.

The compounds disclosed herein can in some embodiments be administered to the subject in combination with one or more additional therapeutic agents and/or in combination with, for example, radiation therapies, ultrasound, and/or surgical interventions. Additional therapeutic agents include, for example, agents that induce apoptosis; polynucleotides (e.g., anti-sense, ribozymes, siRNA); polypeptides (e.g., enzymes and antibodies); biological mimetics; agents that bind to and inhibit anti-apoptotic proteins (e.g., agents that inhibit anti-apoptotic BCL-2 proteins); alkaloids; alkylating agents; antitumor antibiotics; antimetabolites; hormones; platinum compounds; monoclonal or polyclonal antibodies (e.g., antibodies conjugated with anticancer drugs, toxins, defensins, etc.), toxins, radionuclides; biological response modifiers (e.g., interferons (e.g., IFN-.alpha., etc.) and interleukins (e.g., IL-2, etc.), etc.); adoptive immunotherapy agents; hematopoietic growth factors; agents that induce tumor cell differentiation (e.g., all-trans-retinoic acid, etc.); gene therapy reagents (e.g., antisense therapy reagents and nucleotides); tumor vaccines; angiogenesis inhibitors; proteosome inhibitors: NF kappa beta modulators; anti-CDK compounds; and HDAC inhibitors. Agents that induce apoptosis include, for example, radiation (e.g., X-rays, gamma rays, UV); kinase inhibitors (e.g., Epidermal Growth Factor Receptor (EGFR) kinase inhibitor, Vascular Growth Factor Receptor (VGFR) kinase inhibitor, Fibroblast Growth Factor Receptor (FGFR) kinase inhibitor, Platelet-derived Growth Factor Receptor (PDGFR) kinase inhibitor, and Bcr-Abl kinase inhibitors such as GLEEVEC); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; and staurosporine.

In an embodiment, the compounds described herein are administered in the form of a composition comprising the compound and a carrier. The compounds and compositions of the present invention can be administered to subjects using routes of administration known in the art. The administration can be systemic or localized to a specific site. Routes of administration include, but are not limited to, intravenous, intramuscular, intrathecal or subcutaneous injection, parenteral, transdermal, topical, spray inhalation, sublingual, buccal, oral or rectal administration, injection into a specific site, and as a topical ophthalmic solution.

All combinations of the various elements described herein, including all subsets, are within the scope of the invention unless otherwise indicated herein or otherwise clearly contradicted by context. Where a numerical range is provided herein for any parameter, it is understood that all numerical subsets of that numerical range, and all the individual integer values contained therein, are provided as part of the invention.

The subject can be any mammal, such a mouse, a rat, a cat, a dog, a horse, a sheep, a cow, a steer, a bull, livestock, a primate, a monkey, and is preferably a human.

This invention will be better understood from the Experimental Details, which follow. However, one skilled in the art will readily appreciate that the specific methods and results discussed are merely illustrative of the invention as described more fully in the claims that follow thereafter.

Experimental Details

Introduction

Conformational plasticity of mitofusin 2 enables mitochondrial tethering to regulate mitochondrial fusion. The development of an in silico pharmacophore-based screen allowed rational manipulation of the conformational plasticity of mitofusin 2. The results identify the first-in-class activator of mitofusin 2, termed herein as mitofusin activating small molecule (MASM). This small molecule promotes mitochondrial fusion and demonstrates a new paradigm for chemical modulation of apoptosis and mitochondrial respiration, and treatment of related disorders.

Materials and Methods

Structural Model of Mfn2.

The structural model of Mfn2 was calculated based on the I-TASSER (Iterative Threading ASSEmbly Refinement) hierarchical approach to protein structure as previously described (5,17). Top solutions derived from I-TASSER approach were based on the bacterial dynamin-like protein structure in the PDB (ID: 2J69). Energy minimization and analysis of the top-ranked structure was performed with MAESTRO tools (Maestro, v10.5, Schrödinger, LLC). PyMOL (The PyMOL Molecular Graphics System. Version 1.8; Schrödinger, LLC) was used for preparing the figures.

Ligand Preparation Library.

eMolecules (emolecules.com) library of purchasable compounds was converted to 3D structures using LIGPREP (LigPrep, version 3.8, Schrödinger, LLC) and EPIK (Epik, version 3.6, Schrödinger, LLC) generating an in silico library of approximately 13.8 million compounds containing compounds with different ionization state at pH 7.0±2.0, stereochemistry and tautomeric form, excluding potential Pan Assay Interference Compounds (PAINS) using PAINS definitions included in Canvas (18). Conformation analysis of ligands were calculated using the OPLS3 force field.

3D Pharmacophore Model Generation and Screen.

Phase (Phase, version 4.6, Schrödinger, LLC) module was used to generate a pharmacophore hypothesis and a 3D pharmacophore screen (10). The coordinates of the HR1 helix residues Val372, Met376 and His380 from the structural model of Mfn2 were used to assign pharmacophore points in 3D coordinates. Pharmacophore hypothesis included 5 features as defined in Phase for 3 hydrophobic groups to mimic the sidechain residues of Val273 and Met376 and an aromatic ring with a hydrogen-bond donor to mimic the sidechain of His380. The pharmacophore screen used the in silico library of compounds prepared from the eMolecules library in pre-existing conformations with the requirement to satisfy at least 4 out of the 5 pharmacophore features of the hypothesis. The top 1000 compounds-ranked based on the Phase Score were selected for further visual analysis and clustered for diversity using dendritic fingerprints in Canvas (19). Physicochemical and AMDET properties including Lipinski rules, permeability, log P, metabolic liabilities and hERG inhibition were evaluated using QikProp (QikProp, version 3.4, Schrödinger, LLC, New York, N.Y., 2011). The highest 8 ranked compounds and the 10 most diverse compounds yielded selected molecules for experimental validation. MASM7 was checked for potential Pan Assay Interference Compounds (PAINS) (18) and has not been reported as a hit in previous screens in Pubchem database.

Compounds.

Pro-fusion 367-384 Gly peptide, QIAEVRGIMDSLH-MAARGGYGRKKRRQRRR (SEQ ID NO:1) was synthesized, purified at >95% purity by Life Technologies. MASM7 compound was obtained from Enamine (cat. #EN300-396282). Screened MASMs were purchased from Enamine, ChemBridge and ChemDiv. All compounds were >95% pure, dissolved in DMSO to prepare a 10 mM stock solution.

Cell Lines.

Cell lines were purchased from ATCC. MEFs (WT, Mfn1 KO, Mfn2 KO and Mfn1/Mfn2 DKO) were also provided by David Chan's laboratory. HEK 293T cells were provided by Louis Hodgson's laboratory. All cells maintained in DMEM (Life Technologies) supplemented with 10% FBS, 100 U ml$^{-1}$ penicillin/streptomycin and 2 mM L-glutamine.

Cell Viability Assay.

Cells (5×10$^3$ cells/well) were seeded in a 96-well white plate and treated with serial dilutions of MASM7 or vehicle (0.1% DMSO). Cell viability was assayed after 24 h by addition of CellTiter-Glo reagent according to the manufacturer's protocol (Promega). Luminescence was measured using a F200 PRO microplate reader (TECAN). Viability assays were performed in at least triplicate and the data normalized to vehicle-treated control wells. Dilutions of MASM7 were performed using a TECAN D300e Digital Dispenser from 10 mM stocks.

Caspase-3/7 Activation Assay.

Cells (5×10$^3$ cells/well) were seeded in a 96-well white plate and treated with MASM7 (5 μM), doxorubicin (1 μM) or vehicle (0.05% DMSO). Caspase 3/7 activation was measured after 24 h by addition of the Caspase-Glo 3/7 chemiluminescence reagent according to the manufacturer's protocol (Promega). Luminescence was detected by a F200 PRO microplate reader (TECAN).

Mitochondrial Depolarization Assay (mtzA).

MEFs (2×10$^4$ cells/well) were seeded in a 96-well black plate and treated with MASM7 (5 μM), or vehicle (0.05% DMSO) for 24 h. Carbonyl cyanide 3-chlorophenylhydrazone (CCP) was used as a positive control (20 μM, 40 min). Following treatments, cells were stained with 400 nM TMRE (Sigma Cat. 87917) for 20 min at 37° C. Subsequently, cells were washed with once with PBS. Fluorescence intensity was detected by a M100 microplate reader (TECAN, Ex: 540 nm/Em: 579 nm).

Molecular Cloning.

To generate FRET-based Mfn2 biosensor construct, pcDNA3.1-Flag-Mfn2 (5'Flag epitope cassette onto human Mfn2) was used as backbone, and mCerulean (cyan fluorescent protein; CFP) was fused onto 5' of Mfn2 and mVenus (yellow fluorescent protein; YFP) onto 3' of ORF of Mfn2 (20-22). Amplification of mCerulean flanked with two restrict enzyme sites BamHI and EcoRI at 5' and 3', respectively, was carried out by HiFi PCR, and subcloned into pcDNA3.1-Flag-Mfn2 with BamHI and EcoRI digestion to replace Flag tag at 5' of Mfn2. The primer pair is as follows, forward: 5'-AGCCCGGGATCCACCATGGTGTC-CAAAG-3' (SEQ ID NO:2); reverse: 5'-CCTGGGAATG-GATGAACTGTATAAAAAGAATTCCCTGCTCTTC-3' (SEQ ID NO:3). To generate fusion of mVenus at 3' of Mfn2, mVenus fragment bearing a stop codon TAG was amplified with the following primer pair, forward: 5'-CCTGCAGCCCAGCAGATGGGCAATGGT-GAGCAAGGGCGA-3' (SEQ ID NO:4); reverse: 5'-AAACGGGCCCTCTAGACTCGAGCTACTTGTA-CAGCTCGTC-3' (SEQ ID NO:5). Then, the mVenus fragment was fused into pcDNA3.1-Cerulean1-Mfn2 to generate pcDNA3.1-Cerulean1-Mfn2-mVenus with mega-mutagenesis PCR using mVenus fragment as mega primer. PCR conditions: 1x 95° C. 10 min; 15x(95° C. 30 sec, 55 min 30 sec, 68° C. 18 min); 1x72° C. 10 min. The construct was confirmed by sequencing. Mutagenesis PCR was performed to generate FRET-based Mfn2 biosensor mutant D725/L727 mutations, by using the following primer pairs: FRED-Mfn2-D725/L727, forward: 5'-GAAAATT-GAGGTTCTTGCCTCAGCTCAGAGCAAAGCAAAG-3' (SEQ ID NO:6), reverse: 5'-CTTTGCTTTGCTCTGAGCT-GAGGCAAGAACCTCAATTTTC-3' (SEQ ID NO:7).

Fret Assay.

HEK 293T cells (5×10$^5$ cells/well) were seeded in a pre-coated with poly L-lysine 6-well clear bottom plate. Cells were transfected with the total amount of 2.5 μg of DNA per well for the indicated Mfn2 FRET constructs using Lipofectamine® 3000 Reagent (Invitrogen) according to the manufacturer's protocol. The following day, transfected cells were transferred to a pre-coated with poly L-lysine 96-well black plate (2×10$^4$ cells/well). The following day, cell media was replaced with FluoroBrite™ DMEM (Invitrogen) supplemented with 10% FBS, 100 U ml$^{-1}$ penicillin/streptomycin, 2 mM L-glutamine and 1 mM GTPγS 15 min prior treatments with MASMs. GTPγS (Sigma Aldrich) was used to inhibit GTPase activity of Mfn2. Subsequently, cells were treated for 2 h with MASMs or vehicle (0.1% DMSO). Dilutions of MASMs were performed using a TECAN D300e Digital Dispenser from 10 mM stock solutions. Fluorescence intensity was detected by a M100 microplate reader (TECAN), filters that were used for the FRET studies: donor (mCerulean) Ex: 436 nm/Em: 480 nm, acceptor (mVenus) Ex: 436 nm/Em: 535 nm. Acceptor/Donor ratio referred to the text and figures correspond to the ratio of fluorescence intensities (relative fluorescence units: RFU) detected by the acceptor filter/donor filter. Non-transfected cells were used to subtract background fluorescence from each of the aforementioned filters that were used in the study.

NMR Samples and Experiments.

Mfn2 residues 678-757 corresponding to the HR2 domain were cloned into a pET-28 vector and transformed into BL21(DE3) CodonPlus (DE3)-RIPL *E. coli* cells. Cells were grown at 37° C. in 1 L of LB media to an OD$_{600}$ of 0.8, cells were then harvested and resuspended in 1 L of M9 media supplemented with 1.5 gr/L of $^{15}$N ammonium chloride grown for 45 min at 37° C. and induced at 18° C. for 16 hours with 1 mM IPTG. Mfn2 HR2 domain was purified from bacterial pellets by high-pressure homogenization in lysis buffer (20 mM Tris·HCl pH 7, 250 mM KCl, 25 mM imidazole, and Roche complete EDTA free protease inhibitor cocktail) and ultracentrifuged at 45,000 g for 45 min. The supernatant was applied to pre-equilibrated 1 mL HisPur Ni-NTA Resin washed in lysis buffer and eluted using elution buffer (20 mM Tris·HCl pH 6, 250 mM KCl, 400 mM imidazole). $^{15}$N-MFN2-HR2 was further purified by size exclusion chromatography (Superdex 75 Increase 10/300 GL column) in gel filtration buffer (20 mM potassium phosphate pH 6, 150 mM KCl). Fractions containing the $^{15}$N-Mfn2-HR2 were confirmed by SDS-PAGE, pooled and concentrated to 50 μM in NMR buffer (20 mM potassium phosphate pH 6, 150 mM KCl, 10% D20) using a 10 KDa cut-off Centricon spin concentrator for NMR analysis. $^1$H-$^{15}$N-HSQC spectra of 50 μM Mfn2-HR2 in the presence and absence of MASM7 were recorded on a BRUKER AVANCE IIIHD 600 MHz system equipped with a 5 mm H/F-TCI CryoProbe at 25° C. Spectra were processed using qMDD (mddnmr v2.0) and NMRPIPE and analyzed using Analysis (CCPNMR) (23,24).

Live cell imaging. MEFs were seeded on chamber slides (MatTek Corporation: 35 mm dishes, No. 1.5, 14 mm glass diameter) at ~70% confluence. Cells were treated with MASM7 or 367-384 Gly (1 μM, 2 h). Cells were stained with MitoTracker Green (200 nM, Invitrogen) for 20 min at 37° C. After treatments, media was replaced with FluoroBrite™ DMEM (Invitrogen) supplemented with 10% FBS, 100 U ml$^{-1}$ penicillin/streptomycin, 2 mM L-glutamine and MASM7 or 367-384 Gly (1 μM) prior image acquisition. Images were taken with Leica SP5 inverted confocal microscope. Data were analyzed with Image J software. >200 mitochondria were measured per condition in mitochondrial aspect ratio.

Immunofluorescence.

Transfected HEK 293T or MEFs were washed with once PBS and fixed with 2% PFA for 13 min. Subsequently, cells were blocked, then incubated for 1 h at room temperature with the primary antibody for ATP5B (Abcam; ab128743) or active caspase 3 (R&D Systems; AF835). After incubation with the primary antibody, cells were washed with PBS and incubated for 1 h at room temperature with the secondary antibody (ThermoFisher Scientific; A11010). Images were taken with Leica SP5 inverted confocal microscope or Zeiss fluorescent microscope. Data were analyzed with Image J software.

Mitochondrial respiration. Mitochondrial oxygen consumption rates (OCR) were assessed using a XF24 Analyzer (Seahorse Biosciences, Billerica Mass., USA). In brief, $3 \times 10^4$ MEFs were cultured in a XF24 cell culture microplate containing DMEM supplemented with 10% bovine calf serum. Cells were treated with MASM7 or 367-384 Gly (1 µM, 2 h) prior to OCR analysis. Mitochondrial respiration was assessed by the sequential addition of oligomycin (1 µM), carbonyl cyanide-4-(trifluoromethoxy)phenylhydrazone (FCCP, 2 µM) and rotenone (1 µM)-antimycin (1 µM) as previously reported (25). OCR was normalized to cell number or total protein content per well for each condition tested. ATP production was calculated based on the following equation: (latest measurement before oligomycin injection–minimum measurement after oligomycin injection). Data are expressed as Mean±SEM, OCR from untreated control for each condition; using n=3-5 individual experiments with n=3-5 replicates for each group tested.

Results and Discussion

Figure 3A:
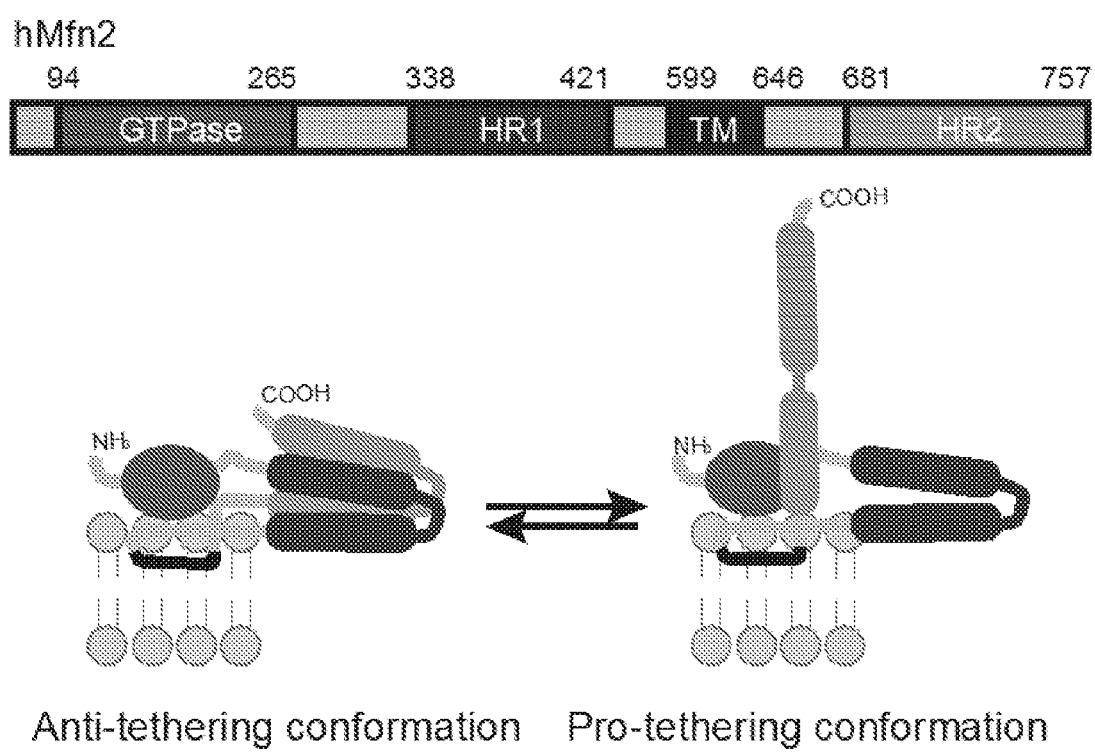
FIG. 3A-3H. Discovery of the mitofusin activating small molecule 7 (MASM7) that induces mitochondrial fusion by promoting the pro-tethering conformations of Mfn2 through binding to HR2 domain. (A) Mfn2 undergoes conformational changes to promote mitochondrial tethering. Anti- and pro-tethering conformations of Mfn2. (B) Ribbon presentation of the Mfn2 structural model and HR1-HR2 interactions. (C) Pharmacophore hypothesis based on the interactions of the sidechains of the HR1-amino acids. (D) Screening of the predicted MASMs from the in silico screening for their capacity to induce mitochondrial fusion. Evaluation of mitochondrial morphology using mitochondrial aspect ratio (Mito AR; length/width) as a readout. (E) Representative micrographs of MEFs treated as indicated. Mitotracker green stains mitochondria. Scale bar 20 µm. Zoomed images are 5×. (F) MASM7 concentration-responsively increased Mito AR in WT MEFs. (G) MASM7 is a non-isoform specific Mfn agonist. Quantification Mito AR in untreated WT, MFN1 KO, MFN2 KO MEFs and MFN1/
Figure 3B:
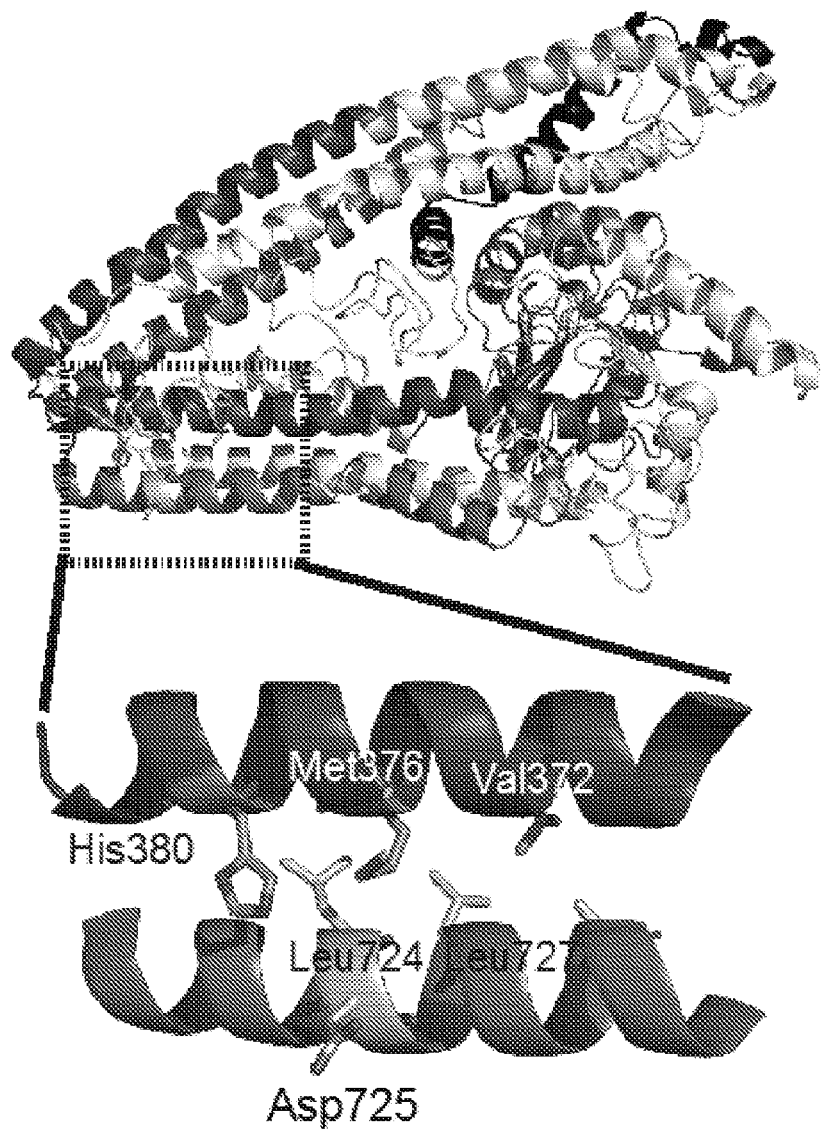
Figure 3C:
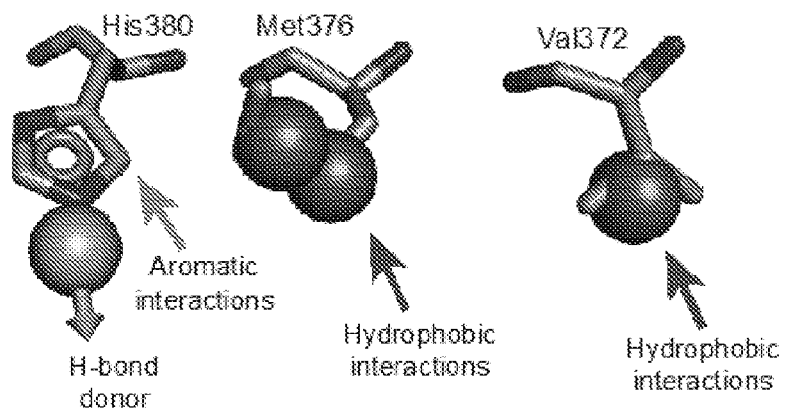
Figure 3D:
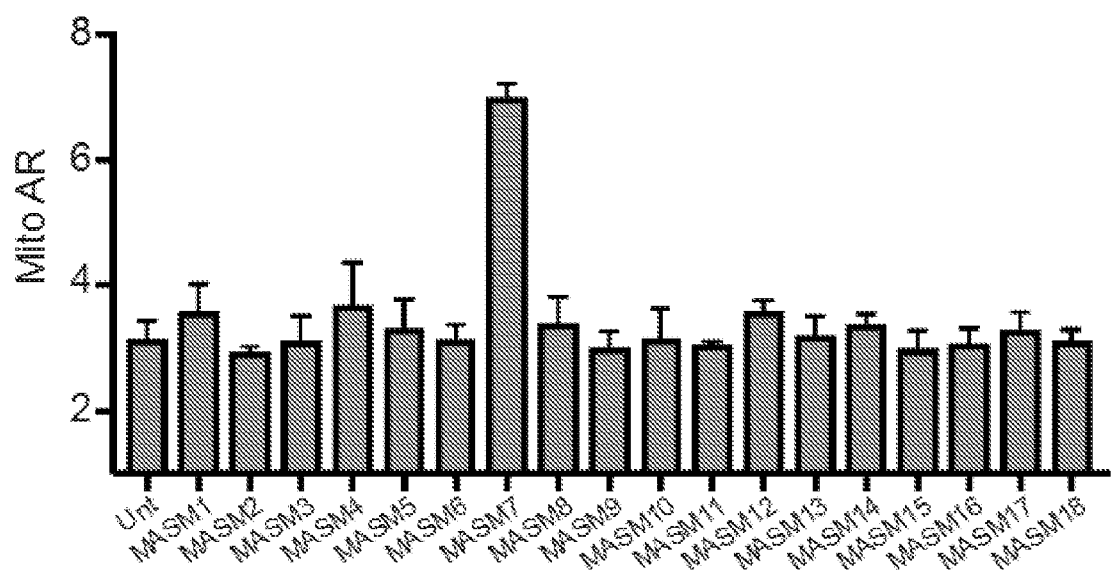
Figure 3E:
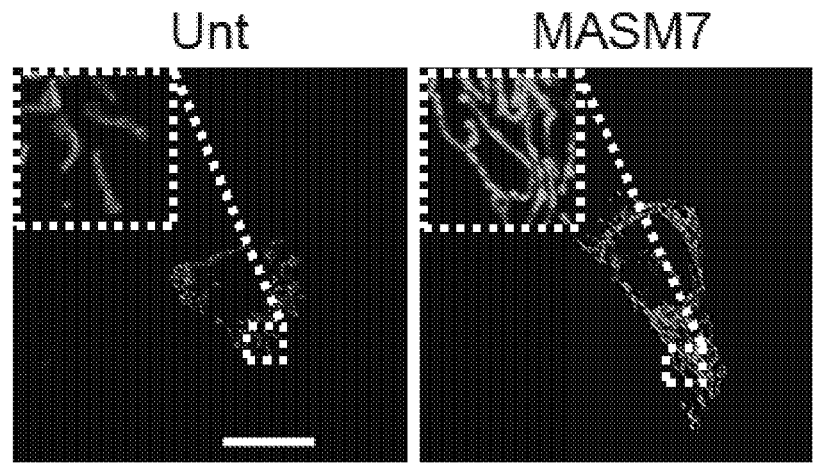

To induce fusion by activating Mfn2, a small molecule was developed that would directly promote the pro-tethering over the anti-tethering conformation of Mfn2 (FIG. 3A). Visual inspection of the intra-molecular HR1-HR2 interactions in the anti-tethering conformation of the predicted human Mfn2 structure and particularly in a region that involves HR1 residues 367-384, provided structural insights for small molecule mimicry (FIG. 3B). Specifically, several hydrophobic interactions were observed between the following HR1-amino acids: Val372, Met376 and HR2-amino acids: Leu724, Leu727 and Ala731 and a possible hydrogen bond between the HR1-amino acid: His380 and HR2-amino acid: Asp725 (FIG. 3B). All these residues are highly conserved among different species of Mfn2 and Mfn1. It was envisioned that a small molecule capable of recapitulating the interactions of the aforementioned HR1-amino acids would compete with intra-molecular HR1-HR2 interactions and gravitate the pro-tethering conformation of Mfn2. Therefore, a pharmacophore hypothesis was generated that comprises the following features: three hydrophobic interactions, an aromatic interaction and a hydrogen bond donor based on the interactions of the HR1 residues: Val372, Met376 and His380 (FIG. 3C). An in silico library of $13.8 \times 10^6$ commercially available small molecules was screened to fit the pharmacophore hypothesis using PHASE (10). The top 1000 hits were clustered for diversity and analyzed based on their interactions with residues of the HR2 domain and molecular properties. Moreover, a number of filters (e.g. elimination of hits with poor ADMET properties using Qikprop) were applied to provide hits with favorable drug-like properties (11). Finally, a subset of 18 compounds (Table 1) was selected for experimental validation based on their fit to the pharmacophore hypothesis and molecular diversity of their scaffolds.

Figure 1A:
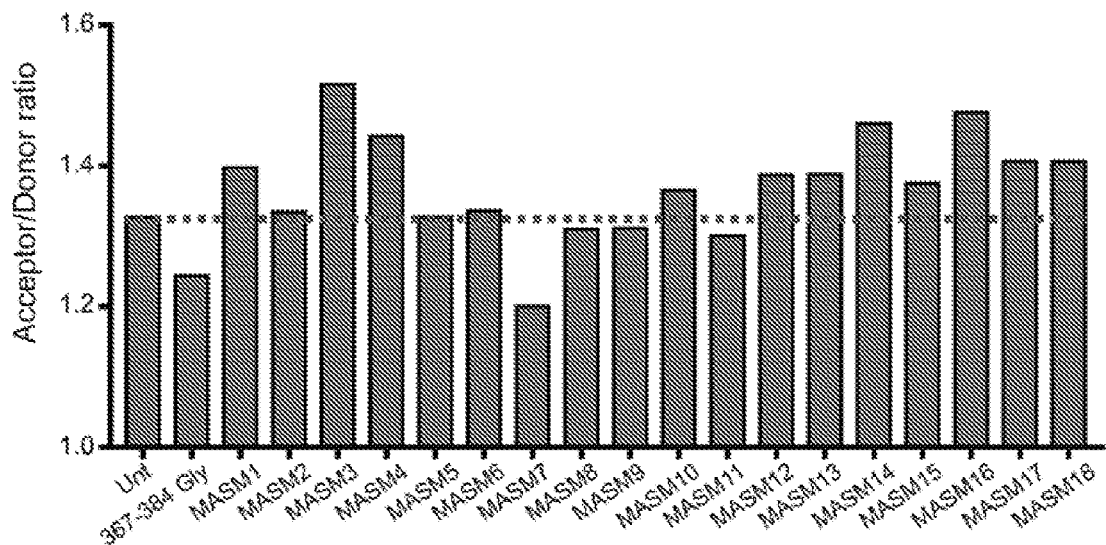
FIG. 1A-1E. Discovery of MASM7 using a FRET-based Mfn2 biosensor. (A) Screening of putative MASMs using FRET-based Mfn2 biosensor in HEK 293T cells. Cells were treated with MASMs or 367-384 Gly (10 µM, 2 h). A 367-384 Gly peptide was used as a positive control (5). (B) Structure of MASM7. (C) MASM7 satisfies pharmacophore hypothesis features. (D) Acceptor/Donor ratios of wild type (WT) and mutant Mfn2 biosensors. (E) Mutant Mfn2 biosensor decreased potency of MASM7. Error bars represent mean±SEM, n=4 of two independent experiments. Upper trace—mutant; lower trace—WT.
Figure 1B:
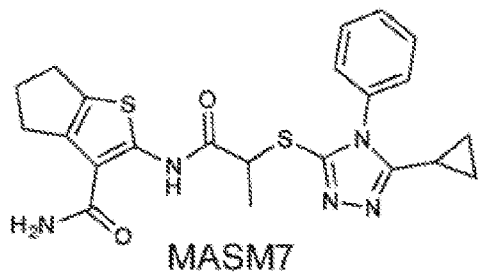

To evaluate the capacity of the selected hits to propel the pro-tethering conformation of Mfn2, a screening assay was developed based on a Forster resonance energy transfer (FRET) biosensor of Mfn2. Briefly, human Mfn2 was fused with mCerulean at the N-terminus and mVenus at the C-terminus and transiently transfected in HEK 293T cells. Loss of intra-molecular HR1-HR2 interactions, occurring in the pro-tethering conformation of Mfn2, increase the distance between mCerulean and mVenus and lead to a decrease in the resonance energy that is transferred. FRET-based Mfn2 biosensor co-localized with ATP synthase subunit beta (ATP5B), in agreement with the idea that this biosensor resides on the OMM. Next, the ability of the 18 putative MASMs to promote the pro-tethering conformation of Mfn2 was examined using a decrease in FRET as a readout (FIG. 1A, Table 1). Strikingly, MASM7 decreased significantly FRET at 10 µM and emerged as the most effective compound in promoting the pro-tethering conformation of Mfn2. MASM7 was resynthesized and its purity was documented by $^1$H and $^{13}$C NMR. Table 2 presents the % of FRET reduction for additional compounds.

Figure 1C:

MASM7 possesses functional groups that fulfill the 5 criteria of pharmacophore hypothesis. Specifically, the thiophene ring mimics the side chain of His380 and the hydrophobic methyl and the cyclopropane groups mimic the side chains of Met376 and Val372, respectively (FIG. 1C). The importance of each functional group was evaluated using the FRET-based Mfn2 biosensor (FIG. 2). Loss of the thiophene ring diminished significantly the ability of this scaffold to reduce FRET. Moreover, the replacement of the methyl group of MASM7 with hydrogen decreased the potency of the compound. Replacement of the cyclopropane group of MASM7 with bulky substituents (e.g. benzene, methylpyrrole) was not tolerated, while the replacement with the pyrrole group was well tolerated. These data suggested that the aforementioned functional groups of MASM7 play a key role in its interactions with Mfn2.

To validate that MASM7 directly interacts with the HR2 domain in vitro, $^{15}$N-labeled Mfn2-HR2 domain (residues 678-757) was produced and heteronuclear quantum spin correlation (HSQC) spectra were recorded with or without MASM7. Titration of MASM7 revealed peak broadening to a number of HR2 residues demonstrating direct binding to the HR2 domain, consistently with the structure-based design.

Figure 1D:
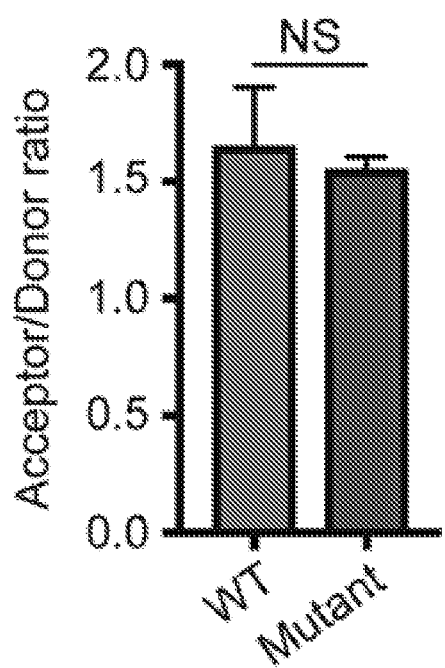
Figure 1E:
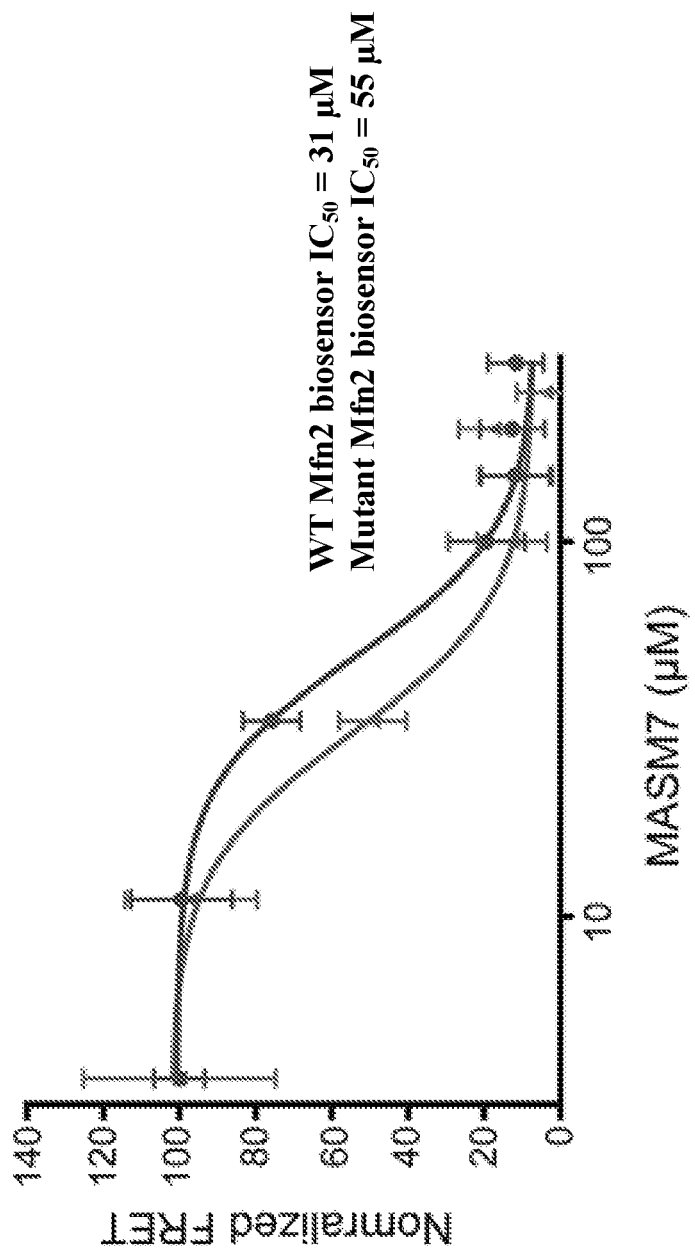

To further validate that MASM7 interacts with the HR2 in cells, a double point FRET-based Mfn2 biosensor mutant (D725A/L727A) was generated, which harbors the mutations that would reduce MASM7-HR2 interactions. Wild type (WT) and mutant FRET-based Mfn2 biosensors presented similar acceptor/donor ratios, suggesting that these double point mutations did not induce structural transformation on Mfn2 (FIG. 1D). MASM7 treatment reduced FRET in a concentration-dependent manner from both WT and mutant FRET-based Mfn2 biosensors (FIG. 1E). Importantly, mutant Mfn2 biosensor required higher concentrations of MASM7 ($IC_{50}$=55 µM) for the reduction of FRET compared to the WT biosensor ($IC_{50}$=31 µM). Therefore, the results indicated that MASM7 functionally interacts with D725 and L727 on the HR2 domain of Mfn2.

Figure 3F:
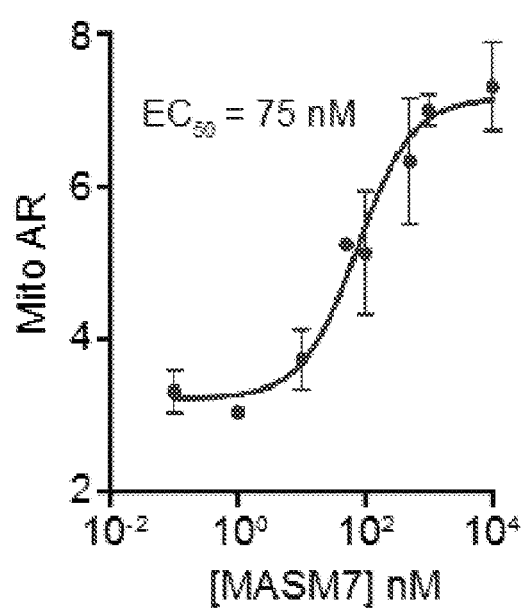
Figure 3G:
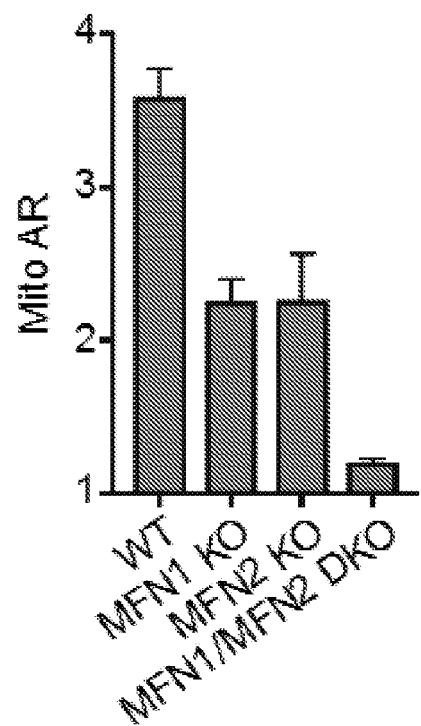
Figure 3H:
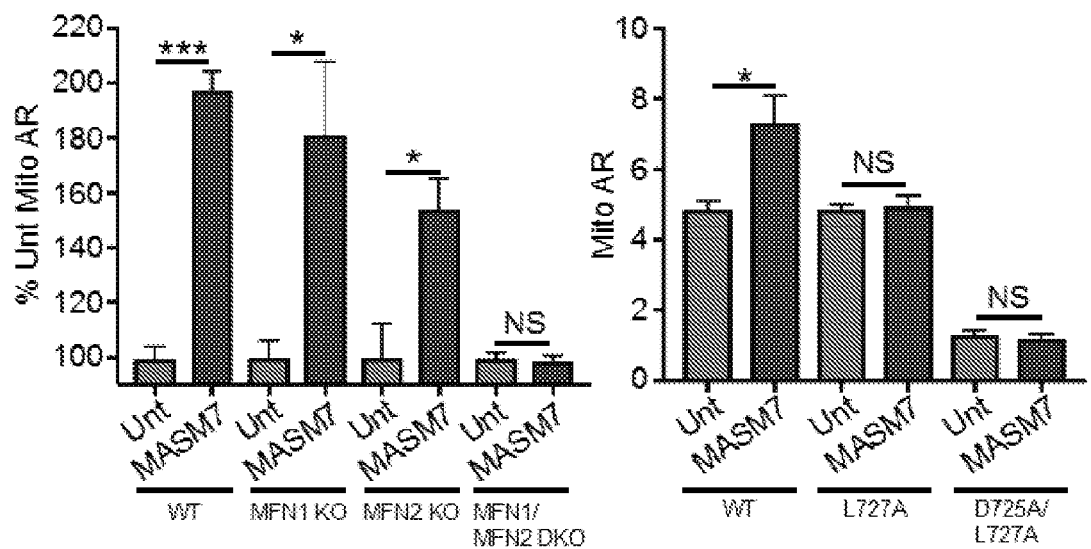

Next, it was visually examined if MASM7 could induce mitochondrial fusion in MEFs, using mitochondrial aspect ratio (mitochondrial length/width, reflecting fusion) as a readout. A 367-384 Gly peptide was used as a positive control (5). Notably, MASM7 increased mitochondrial aspect ratio in WT MEFs, but not in MFN1 KO, MFN2 KO and MFN1/2 DKO MEFs (FIG. 3D, 3E, 3G, 3H). These data indicated that both Mfn2 and Mfn1 could be activated by MASM7, consistent with the pharmacophore hypothesis that used residues of Mfn2 and Mfn1 with high sequence homology. Strikingly, MASM7 is a potent inducer of fusion, achieving an $EC_{50}$ approximately four times lower than 367-384 Gly (MASM7 $EC_{50}$=75 nM; 367-384 Gly $EC_{50}$=340 nM) (FIG. 3F). It is noteworthy, that MASM7 treatment did not reduce viability or mitochondrial membrane potential, and did not induce caspase 3/7 activation in MEFs (FIG. 4). MASH7 increases mitochondrial respiration (oxygen consumption), increases production of ATP, and induces apoptosis and cytotoxicity in cancer cells such as lymphoma, melanoma, lung cancer, breast etc. (FIG. 5).

Consistent with previous reports showing that inhibition of fission reduced apoptosis (8,12-14), the effect of MASM7 was evaluated upon a classic apoptotic stimulus such as staurosporine (STS) in MEFs. MASM7 exhibited anti-apoptotic properties in response to STS treatment and reduced significantly the population of MEFs that was found to be positive to caspase 3 activation when co-treated with STS.

In addition, there is a growing body of reports that link Mfn2 with cellular respiration (3,15,16). Loss of Mfn2 results in a fragmented mitochondrial morphology and has a negative impact on mitochondrial physiology (e.g., reduced mitochondrial membrane potential) (3,5,15,16). Although the role of Mfn2 in the regulation of respiration is not fully understood, the conventional perception is that respiration would rely on Mfn2 activity and healthy mitochondria. Given that one can chemically activate Mfn2 and induce mitochondrial fusion by treating cells with MASM7, the impact on cellular oxygen consumption was tested. In fact, MASM7 increased basal and maximal oxygen rate consumption (OCR) and ATP production in MEFs. These data indicate that Mfn2 activation positively correlates with increased cellular respiration and ATP production.

REFERENCES

1. Detmer, S. A. et al. *Nat. Rev. Mol. Cell Biol* 8, 870-879 (2007).
2. Shirihai, O. S. L et al. *Circ. Res.* 116, 1835-1849 (2015).
3. Schrepfer, E. et al. *Mol. Cell* 61, 683-694 (2016).
4. Koshiba, T. et al. *Science* 305, 858-862 (2004).
5. Franco, A. et al. *Nature* 540, 74-79 (2016).
6. Cao, Y.-L. et al. *Nature* 542, 372-376 (2017).
7. Bombelli, F. et al. *JAMA Neurol.* 71, 1036-1042 (2014).
8. Wang, D. et al. *Angew. Chem. Int. Ed.* 51, 9032-9305 (2012).
9. Yue, W. et al. *Cell Res.* 24, 482-496 (2014).
10. Dixon, S. L et. al. *J. Comput. Aided Mol. Des.* 20, 647-671 (2006).
11. Duffy, E. M. et al. *J. Am. Chem. Soc.* 122, 2878-88 (2000).
12. Frank, S. et al. *Dev. Cell* 1, 515-525 (2001).
13. Cassidy-Stone, A. et al. *Dev. Cell* 14, 193-204 (2008).
14. Suen, D.-F. et al. *Genes Dev.* 22, 1577-1590 (2008).
15. Chen, H. et al. *J. Biol. Chem.* 280, 26185-26192 (2005).
16. Mourier, A. et al. *J. Cell Biol.* 208, 429-442 (2015).
17. Yang, J. et al. *Nat. Methods* 12, 7-8 (2015).
18. Baell, J. et al. *Nature* 513, 481-483 (2014).
19. Sastry, M. et al. *J Chem. Inf. Model.* 50, 771-784 (2010).
20. Yun, C. et al. *Science* 34, 471-475 (2013).
21. Rizzo, M. A. et al. *Nat. Biotechnol.* 22, 445-449 (2004).
22. Takeharu N. et al. *Nat. Biotechnol.* 20, 87-90 (2002).
23. Vranken, W. F. et al. *Proteins* 59, 687-696 (2005).
24. Delaglio, F. et al. *J Biomol. NMR* 6, 277-293 (1995).
25. Dhingra, R. et al. *Proc. Natl. Acad. Sci.* 111, 5537-5547 (2014).

TABLE 1

Table of Compounds.

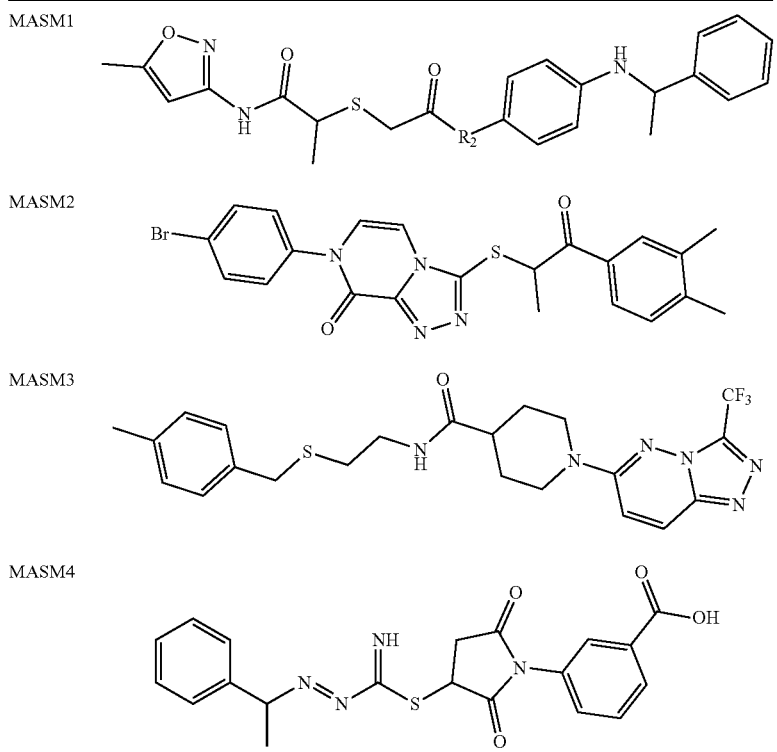

TABLE 1-continued
Table of Compounds.
MASM5
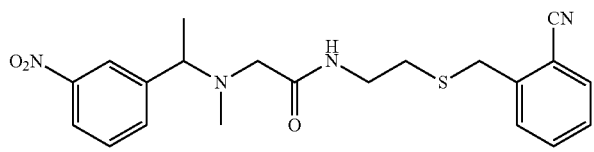 [SMILES: CC(c1cccc([N+](=O)[O-])c1)N(C)CC(=O)NCCSCc1ccccc1C#N]
MASM6
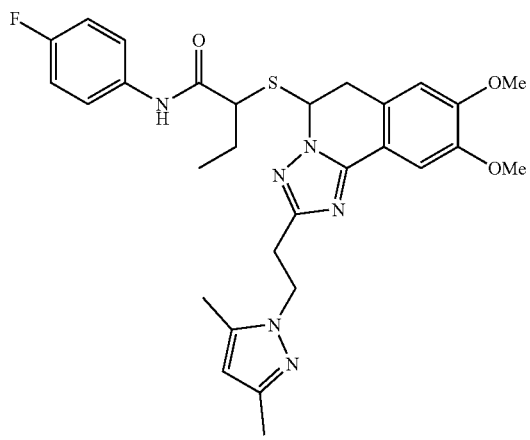 [SMILES: CCC(SC1Cc2cc(OC)c(OC)cc2-c2nc(CCn3nc(C)cc3C)nn21)C(=O)Nc1ccc(F)cc1]
MASM8
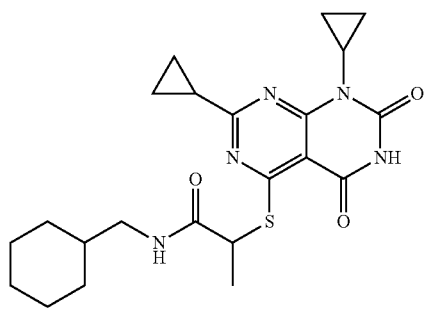 [SMILES: CC(Sc1nc(C2CC2)nc2c1c(=O)[nH]c(=O)n2C1CC1)C(=O)NCC1CCCCC1]
MASM9
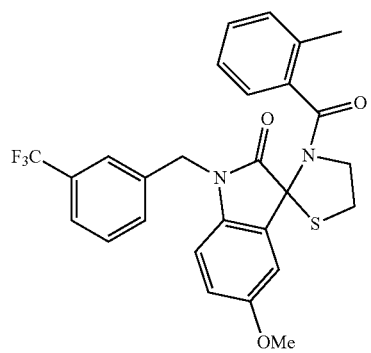 [SMILES: COc1ccc2c(c1)C1(SCCN1C(=O)c1ccccc1C)C(=O)N2Cc1cccc(C(F)(F)F)c1]
MASM10
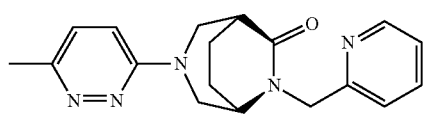

TABLE 1-continued
Table of Compounds.
MASM11
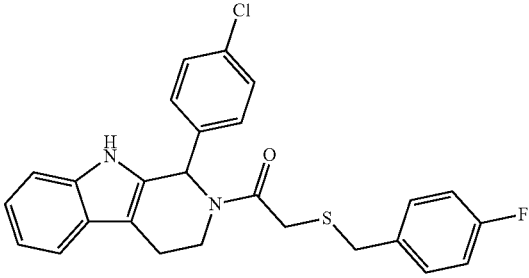 [SMILES: O=C(CSCc1ccc(F)cc1)N1CCc2c([nH]c3ccccc23)C1c1ccc(Cl)cc1]
MASM12
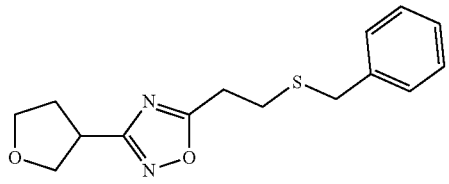 [SMILES: c1ccc(CSCCc2nc(C3CCOC3)no2)cc1]
MASM13
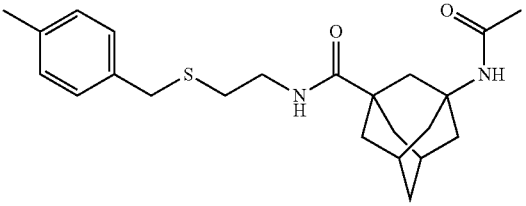 [SMILES: CC(=O)NC12CC3CC(C1)CC(C(=O)NCCSCc1ccc(C)cc1)(C3)C2]
MASM14
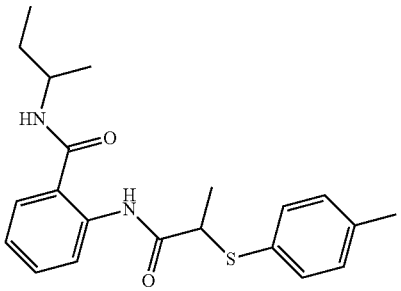 [SMILES: CCC(C)NC(=O)c1ccccc1NC(=O)C(C)Sc1ccc(C)cc1]
MASM15
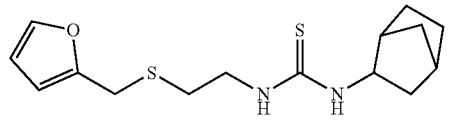 [SMILES: S=C(NCCSCc1ccco1)NC1CC2CCC1C2]
MASM16
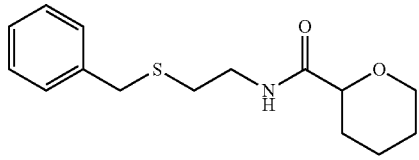 [SMILES: O=C(NCCSCc1ccccc1)C1CCCCO1]
MASM17
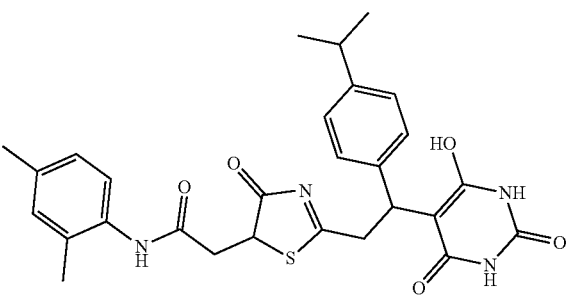 [SMILES: Cc1ccc(NC(=O)CC2SC(CC(c3ccc(C(C)C)cc3)c3c(O)[nH]c(=O)[nH]c3=O)=NC2=O)c(C)c1]

TABLE 1-continued

Table of Compounds.

MASM18 — [structure: 1H-pyrazol-3-yl amide of 2-((4-methoxyphenyl)thio)propanamide]

MASM7 — [structure: 5,6-dihydro-4H-cyclopenta[b]thiophene-3-carboxamide-2-yl amide of 2-((4-phenyl-5-cyclopropyl-4H-1,2,4-triazol-3-yl)thio)propanamide]

TABLE 2

% of FRET reduction for various compounds.

| Compound | Structure | % of FRET reduction |
|---|---|---|
| MASM1 | [5-methylisoxazol-3-yl amide linked via S-CH2-C(O)NH to 4-(1-phenylethylamino)phenyl] | −5.3 |
| MASM2 | [7-(4-bromophenyl)-8-oxo-7,8-dihydro-[1,2,4]triazolo[4,3-a]pyrazin-3-yl thio propyl 3,4-dimethylphenyl ketone] | −0.5 |
| MASM3 | [4-methylbenzyl-S-CH2CH2-NH-C(O)-piperidine-4-yl linked to 3-(trifluoromethyl)-[1,2,4]triazolo[4,3-b]pyridazin-6-yl] | −14.1 |
| MASM4 | [1-phenylethyl-N=N-C(=NH)-S-(2,5-dioxopyrrolidin-3-yl) with N-(3-carboxyphenyl)] | −8.6 |
| MASM5 | [1-(3-nitrophenyl)ethyl-N(Me)-CH2-C(O)-NH-CH2CH2-S-CH2-(2-cyanophenyl)] | 0 |

TABLE 2-continued

% of FRET reduction for various compounds.

| Compound | Structure | % of FRET reduction |
|---|---|---|
| MASM6 | 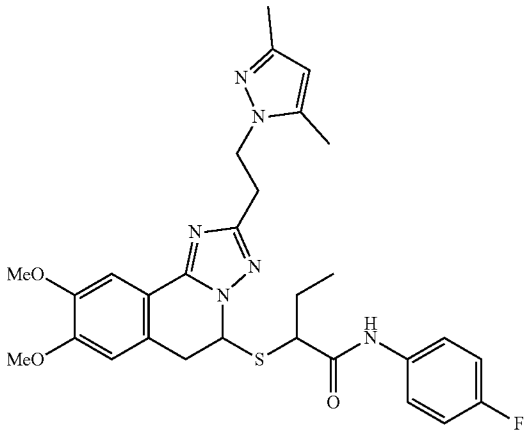 [SMILES: CCC(SC1Cc2cc(OC)c(OC)cc2-c2nc(CCn3nc(C)cc3C)nn21)C(=O)Nc1ccc(F)cc1] | −0.7 |
| MASM7 | 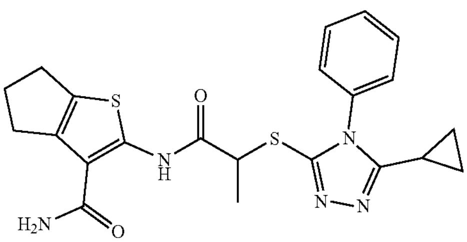 [SMILES: CC(Sc1nnc(C2CC2)n1-c1ccccc1)C(=O)Nc1sc2c(c1C(N)=O)CCC2] | 9.4 |
| MASM8 | 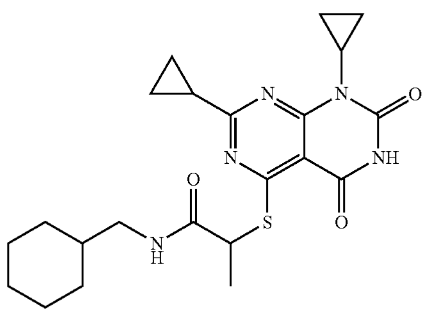 [SMILES: CC(Sc1nc(C2CC2)nc2c1c(=O)[nH]c(=O)n2C1CC1)C(=O)NCC1CCCCC1] | 1.2 |
| MASM9 | 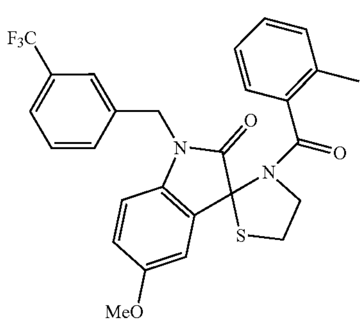 [SMILES: COc1ccc2c(c1)C1(SCCN1C(=O)c1ccccc1C)C(=O)N2Cc1cccc(C(F)(F)F)c1] | 1.1 |
| MASM10 | 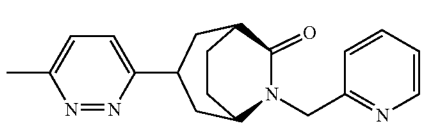 | −2.9 |

TABLE 2-continued

% of FRET reduction for various compounds.

| Compound | Structure | % of FRET reduction |
|---|---|---|
| MASM11 | 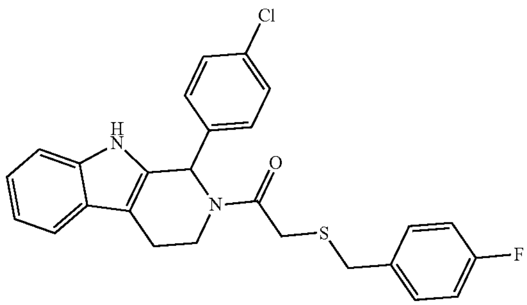 [SMILES: O=C(CSCc1ccc(F)cc1)N1CCc2c([nH]c3ccccc23)C1c1ccc(Cl)cc1] | 1.97 |
| MASM12 | 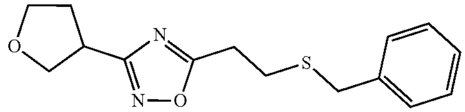 [SMILES: c1ccc(CSCCc2nc(C3CCOC3)no2)cc1] | −4.5 |
| MASM13 | 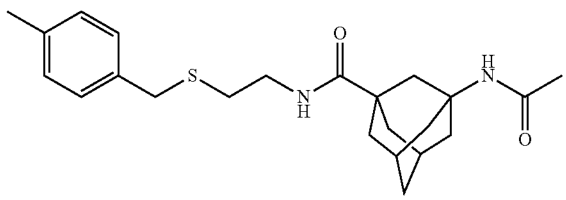 [SMILES: CC(=O)NC12CC3CC(C1)CC(C(=O)NCCSCc1ccc(C)cc1)(C3)C2] | −4.6 |
| MASM14 | 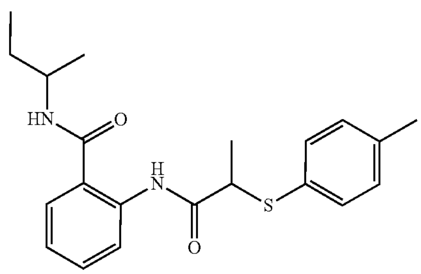 [SMILES: CCC(C)NC(=O)c1ccccc1NC(=O)C(C)Sc1ccc(C)cc1] | −10 |
| MASM15 | 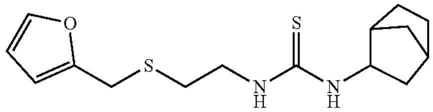 [SMILES: S=C(NCCSCc1ccco1)NC1CC2CCC1C2] | −3.6 |
| MASM16 | 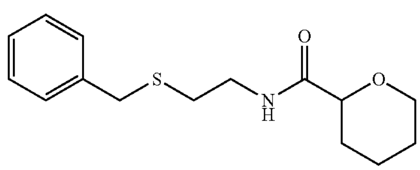 [SMILES: O=C(NCCSCc1ccccc1)C1CCCCO1] | −11.2 |
| MASM17 | 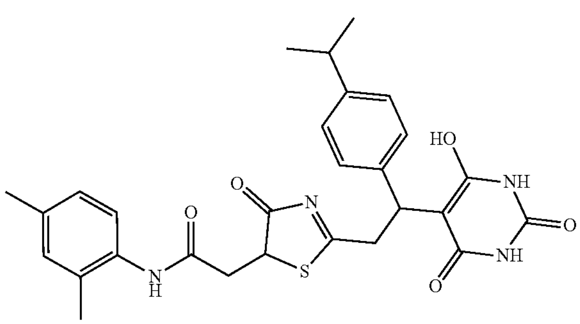 [SMILES: Cc1ccc(NC(=O)CC2SC(CC(c3ccc(C(C)C)cc3)c3c(O)[nH]c(=O)[nH]c3=O)=NC2=O)c(C)c1] | −5.9 |

TABLE 2-continued

% of FRET reduction for various compounds.

| Compound | Structure | % of FRET reduction |
|---|---|---|
| MASM18 | 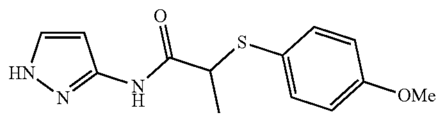 [SMILES: COc1ccc(SC(C)C(=O)Nc2cc[nH]n2)cc1] | −5.8 |
| MASM7 | 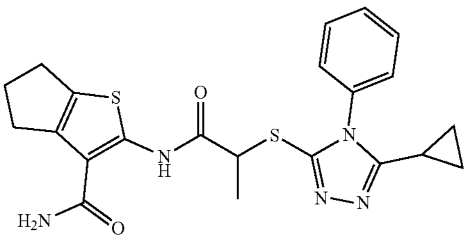 [SMILES: CC(Sc1nnc(C2CC2)n1-c1ccccc1)C(=O)Nc1sc2c(c1C(N)=O)CCC2] | 27.4 |
| MASM19 | 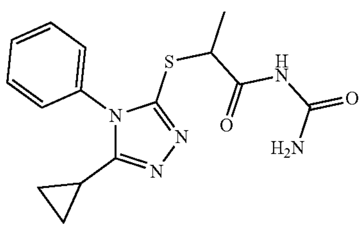 [SMILES: CC(Sc1nnc(C2CC2)n1-c1ccccc1)C(=O)NC(N)=O] | 2.7 |
| MASM20 | 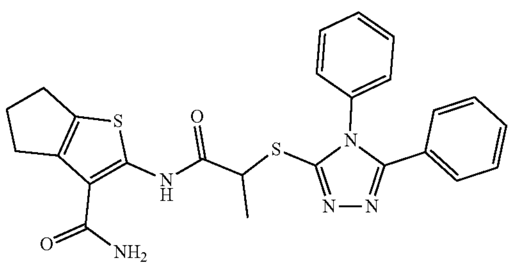 [SMILES: CC(Sc1nnc(-c2ccccc2)n1-c1ccccc1)C(=O)Nc1sc2c(c1C(N)=O)CCC2] | 10.1 |
| MASM21 | 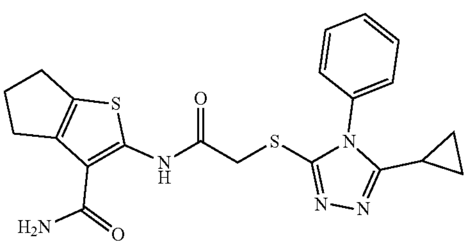 [SMILES: NC(=O)c1c(NC(=O)CSc2nnc(C3CC3)n2-c2ccccc2)sc2c1CCC2] | 27.1 |
| MASM22 | 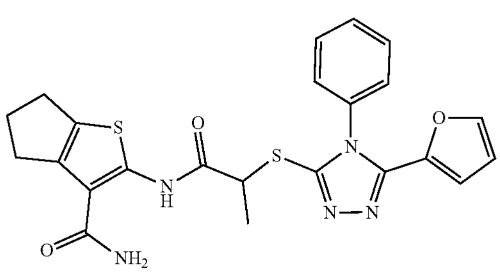 [SMILES: CC(Sc1nnc(-c2ccco2)n1-c1ccccc1)C(=O)Nc1sc2c(c1C(N)=O)CCC2] | 31.7 |

TABLE 2-continued
% of FRET reduction for various compounds.
| Compound | Structure | % of FRET reduction |
|---|---|---|
| MASM23 | 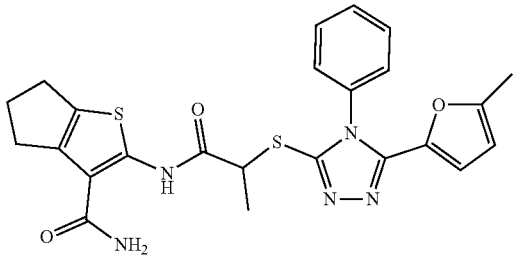 [SMILES: Cc1ccc(-c2nnc(SC(C)C(=O)Nc3sc4c(c3C(N)=O)CCC4)n2-c2ccccc2)o1] | 13.9 |
| MASM24 | 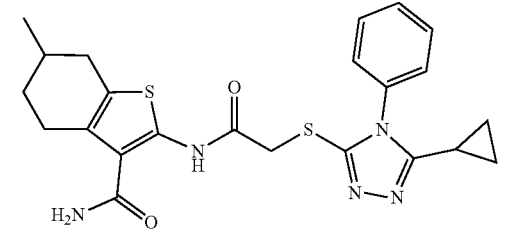 [SMILES: CC1CCc2c(sc(NC(=O)CSc3nnc(C4CC4)n3-c3ccccc3)c2C(N)=O)C1] | 18.9 |
| MASM25 | 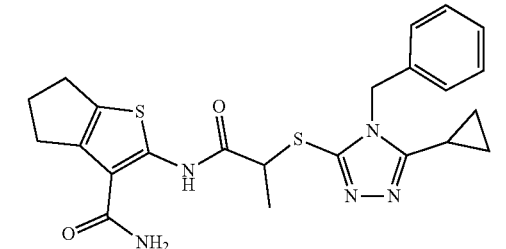 | 32.2 |
| MASM26 | 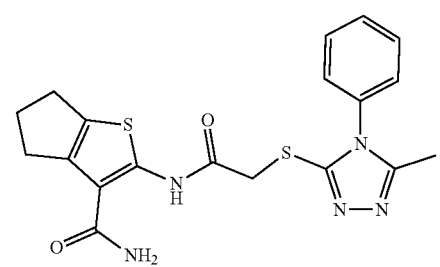 [SMILES: Cc1nnc(SCC(=O)Nc2sc3c(c2C(N)=O)CCC3)n1-c1ccccc1] | 37.0 |
| MASM27 | 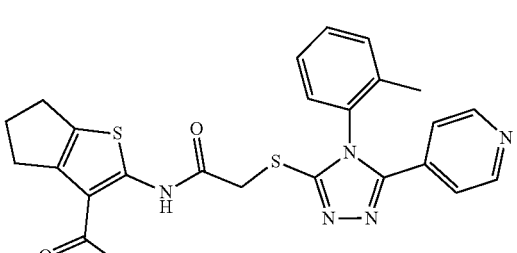 | 30.0 |

TABLE 2-continued

% of FRET reduction for various compounds.

| Compound | Structure | % of FRET reduction |
|---|---|---|
| MASM28 | 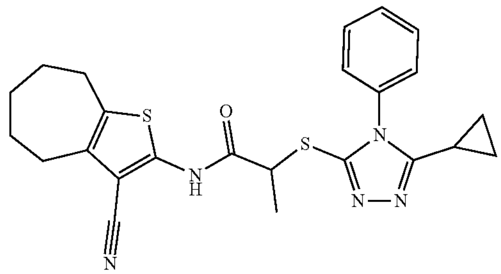 [SMILES: CC(Sc1nnc(C2CC2)n1-c1ccccc1)C(=O)Nc1sc2c(c1C#N)CCCCC2] | 8.0 |
| MASM29 | 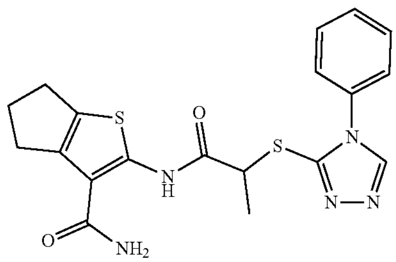 [SMILES: CC(Sc1nncn1-c1ccccc1)C(=O)Nc1sc2c(c1C(N)=O)CCC2] | 16.5 |
| MASM30 | 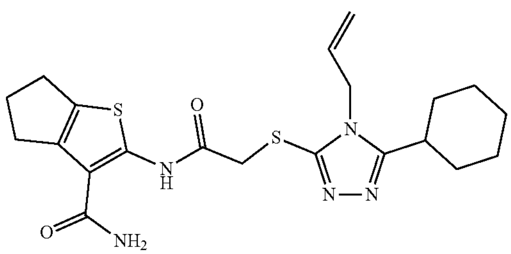 [SMILES: C=CCn1c(SCC(=O)Nc2sc3c(c2C(N)=O)CCC3)nnc1C1CCCCC1] | 17.7 |
| MASM31 | 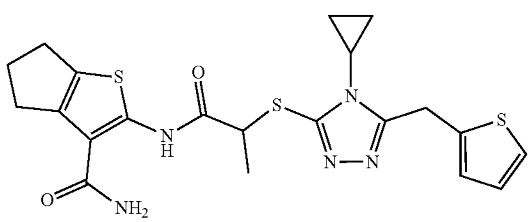 [SMILES: CC(Sc1nnc(Cc2cccs2)n1C1CC1)C(=O)Nc1sc2c(c1C(N)=O)CCC2] | 30.7 |
| MASM32 | 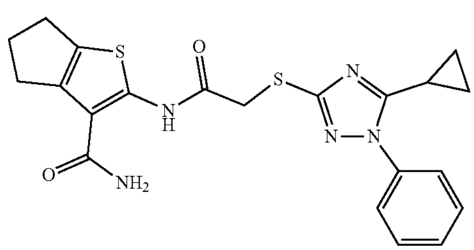 [SMILES: NC(=O)c1c(NC(=O)CSc2nc(C3CC3)n(-c3ccccc3)n2)sc2c1CCC2] | 37.0 |

TABLE 2-continued

% of FRET reduction for various compounds.

| Compound | Structure | % of FRET reduction |
|---|---|---|
| MASM33 | 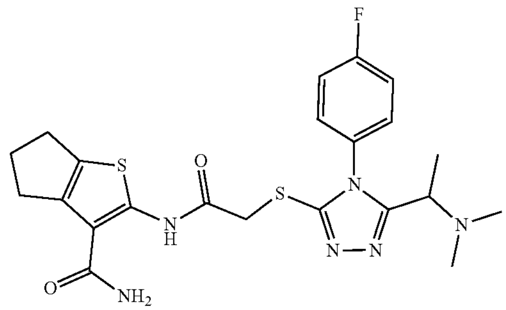 [SMILES: CC(c1nnc(SCC(=O)Nc2sc3c(c2C(N)=O)CCC3)n1-c1ccc(F)cc1)N(C)C] | 31.9 |
| MASM34 | 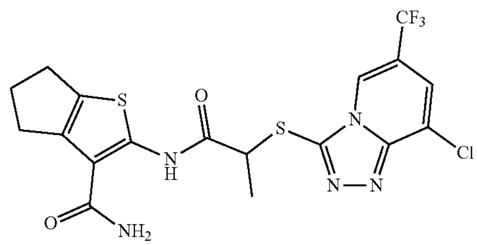 [SMILES: CC(Sc1nnc2c(Cl)cc(C(F)(F)F)cn12)C(=O)Nc1sc2c(c1C(N)=O)CCC2] | 19.4 |
| MASM35 | 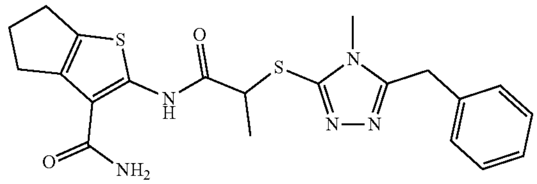 [SMILES: CC(Sc1nnc(Cc2ccccc2)n1C)C(=O)Nc1sc2c(c1C(N)=O)CCC2] | 25.9 |
| MASM36 | 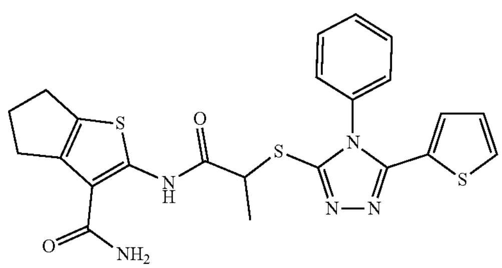 [SMILES: CC(Sc1nnc(-c2cccs2)n1-c1ccccc1)C(=O)Nc1sc2c(c1C(N)=O)CCC2] | 11.1 |
| MASM37 | 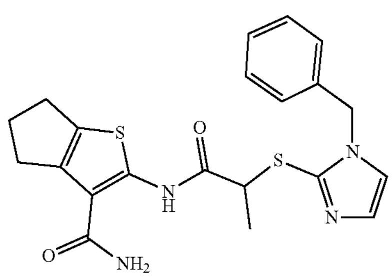 [SMILES: CC(Sc1nccn1Cc1ccccc1)C(=O)Nc1sc2c(c1C(N)=O)CCC2] | 21.0 |
| MASM38 | 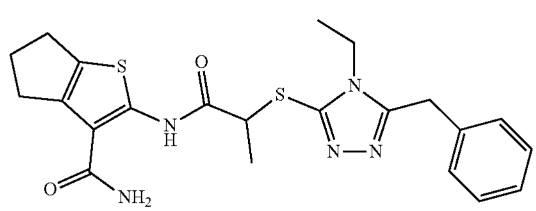 [SMILES: CCn1c(Cc2ccccc2)nnc1SC(C)C(=O)Nc1sc2c(c1C(N)=O)CCC2] | 9.9 |

TABLE 2-continued

% of FRET reduction for various compounds.

| Compound | Structure | % of FRET reduction |
|---|---|---|
| MASM39 | 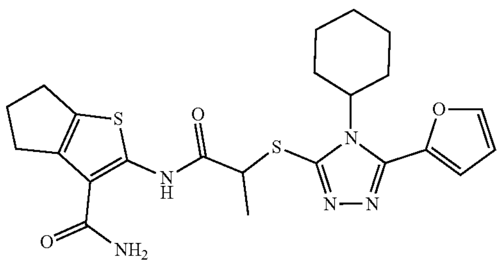 [SMILES: CC(Sc1nnc(-c2ccco2)n1C1CCCCC1)C(=O)Nc1sc2c(c1C(N)=O)CCC2] | 9.9 |
| MASM40 | 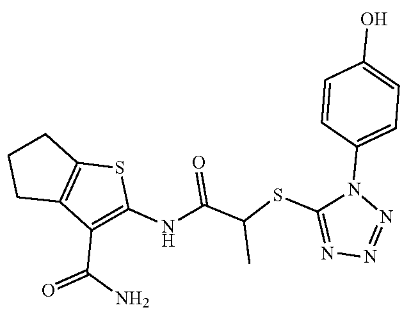 [SMILES: CC(Sc1nnnn1-c1ccc(O)cc1)C(=O)Nc1sc2c(c1C(N)=O)CCC2] | 22.6 |
| MASM41 | 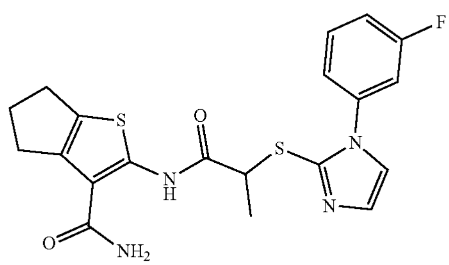 [SMILES: CC(Sc1nccn1-c1cccc(F)c1)C(=O)Nc1sc2c(c1C(N)=O)CCC2] | 10.2 |
| MASM42 | 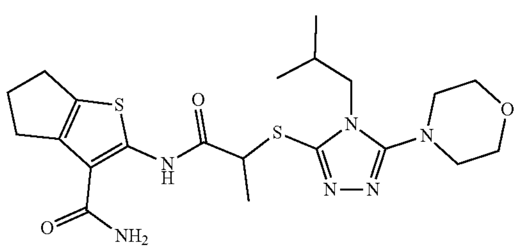 [SMILES: CC(C)Cn1c(SC(C)C(=O)Nc2sc3c(c2C(N)=O)CCC3)nnc1N1CCOCC1] | −1.4 |
| MASM43 | 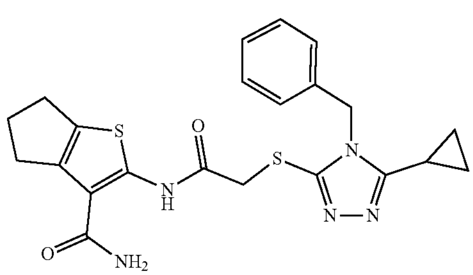 [SMILES: NC(=O)c1c(NC(=O)CSc2nnc(C3CC3)n2Cc2ccccc2)sc2c1CCC2] | 14.8 |

TABLE 2-continued

% of FRET reduction for various compounds.

| Compound | Structure | % of FRET reduction |
|---|---|---|
| MASM44 | 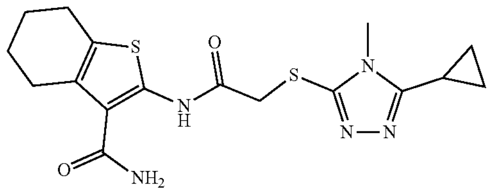 [SMILES: Cn1c(SCC(=O)Nc2sc3c(c2C(N)=O)CCCC3)nnc1C1CC1] | 23.3 |
| MASM45 | 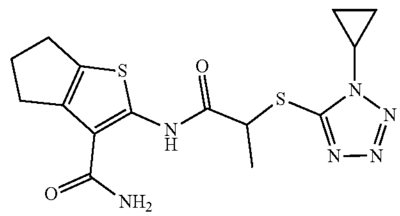 [SMILES: CC(Sc1nnnn1C1CC1)C(=O)Nc1sc2c(c1C(N)=O)CCC2] | 26.4 |

---

What is claimed is:

1. A method of treating a disease or disorder in a subject, wherein the disease or disorder is selected from the group consisting of a renal, hepatic and/or bowel ischemia, heart failure, cardiomyopathy, pancreatic cancer, gastrointestinal cancer, breast cancer, cervical carcinoma, liver cancer, and leukemia, the method comprising administering to the subject a compound of formula (III) in an amount effective to activate mitofusin 1 or mitofusin 2 to treat the disease or disorder, wherein
formula (III) is

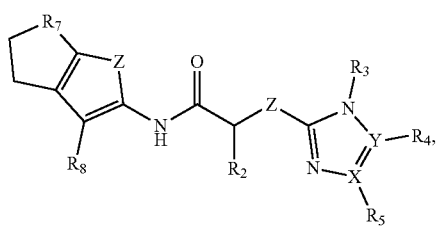

(III)

wherein

R2 is H, or $C_1$-$C_4$ alkyl;

R3 and R5 are independently H, alkenyl, alkynyl, cycloalkyl, $CHCH_3N(CH_3)_2$, heterocycloalkyl, benzyl, aryl, heteroaryl, aralkyl, heteroaralkyl, or optionally substituted aryl, aralkyl, heteroaryl, or heteroaralkyl, wherein the optional substituent is one or more of F, Cl, Br, I, OH, $CH_3$, SH, or $CF_3$;

R4 is H, alkenyl, alkynyl, cycloalkyl, $CHCH_3N(CH_3)_2$, heterocycloalkyl, benzyl, aryl, 5- or 6-membered heteroaryl, aralkyl, heteroaralkyl, or optionally substituted 6-membered aryl, aralkyl, 5- or 6-membered heteroaryl, or heteroaralkyl, wherein the optional substituent is one or more of F, Cl, Br, I, OH, $CH_3$, SH or $CF_3$;

R7 is $CH_2$, $CH_2CH_2$, $CH_2CH_2CH_2$ or $CH_2CH(CH_3)$;

R8 is CN, $CONH_2$, COOH or COOR9;

R9 is $C_1$-$C_4$ alkyl;

X and Y are independently N or C;

Z is S;

provided that in Formula III when R4 or R5 is heteroaryl and R8 is $CONH_2$, R2 is not H;

or a pharmaceutically acceptable salt, ester or prodrug thereof, and provided that the compound is not any of the following:

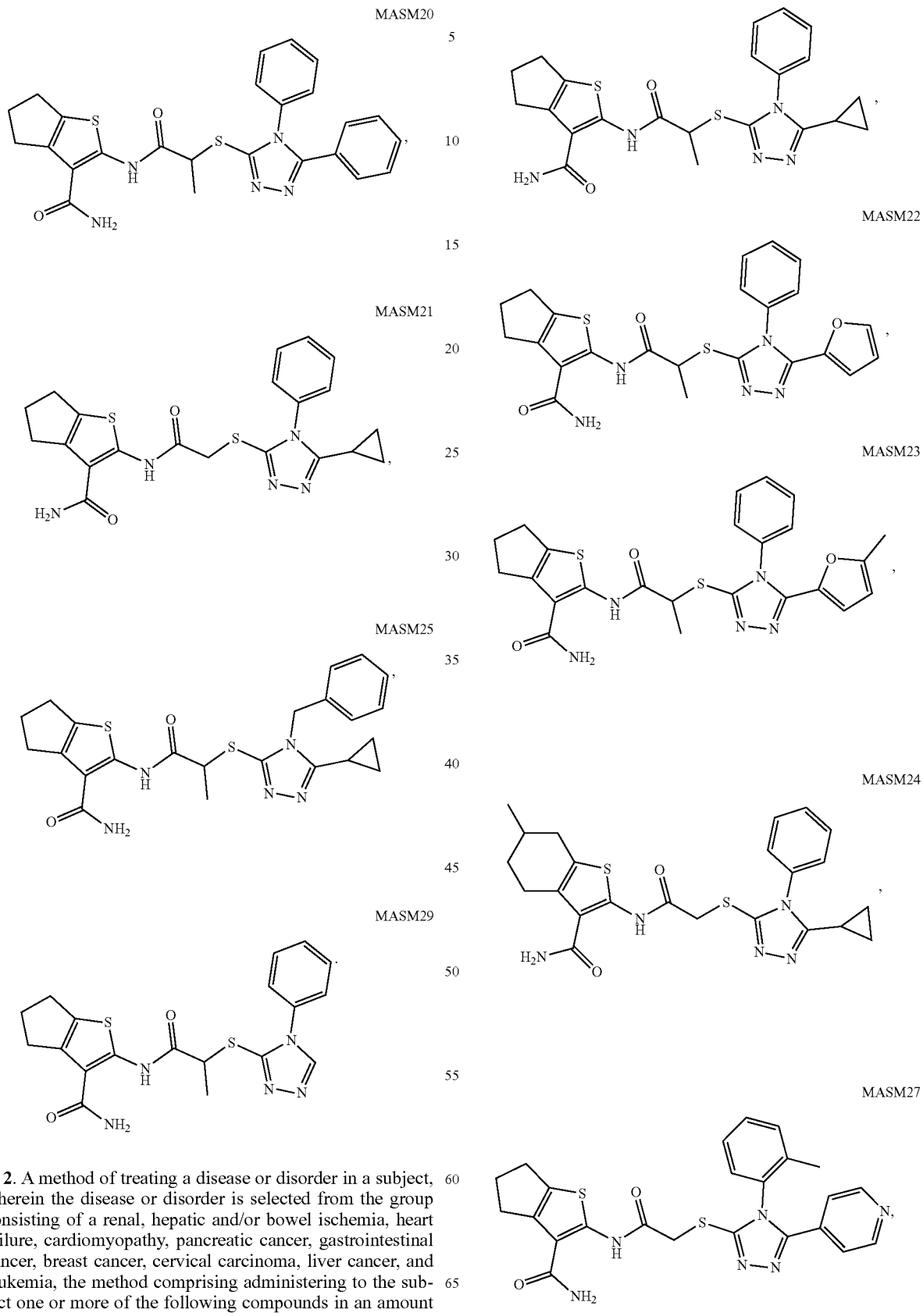

2. A method of treating a disease or disorder in a subject, wherein the disease or disorder is selected from the group consisting of a renal, hepatic and/or bowel ischemia, heart failure, cardiomyopathy, pancreatic cancer, gastrointestinal cancer, breast cancer, cervical carcinoma, liver cancer, and leukemia, the method comprising administering to the subject one or more of the following compounds in an amount effective to treat the disease or disorder:

MASM28
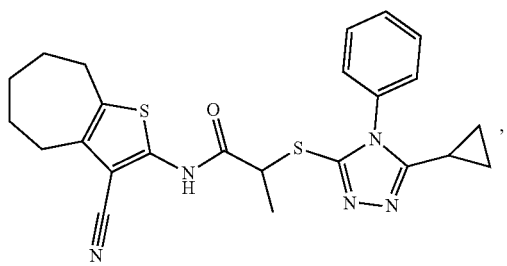
MASM30
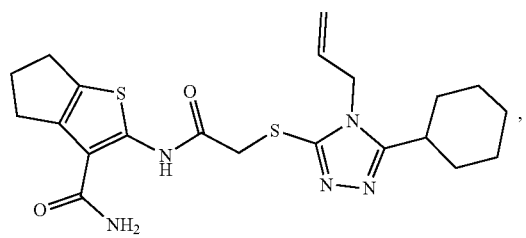
MASM31
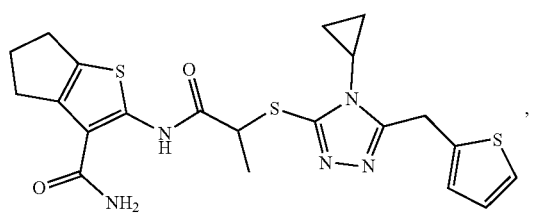
MASM32
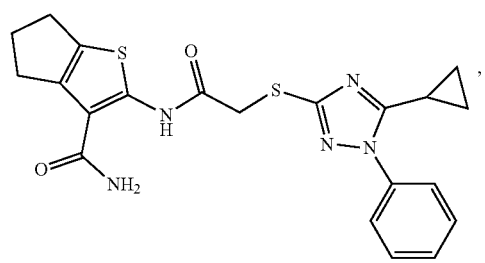
MASM33
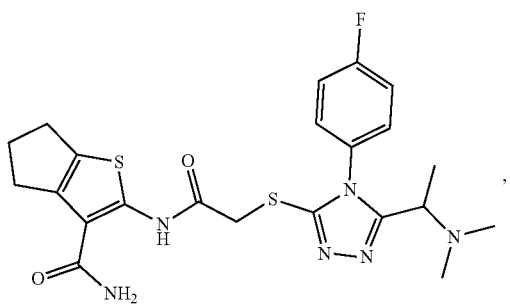
MASM36
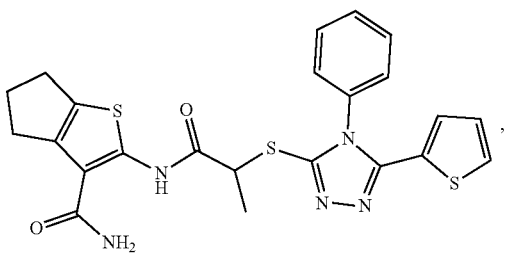
MASM37
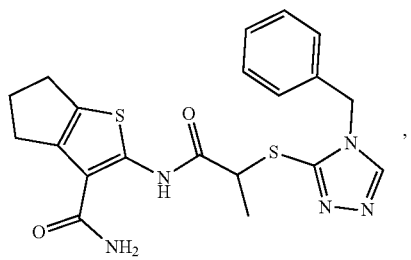
MASM39
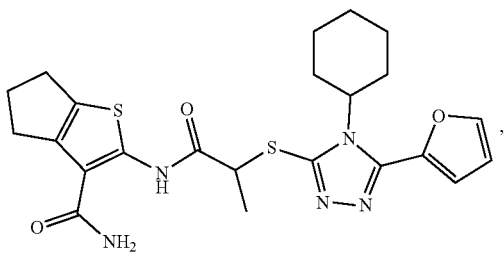
MASM40
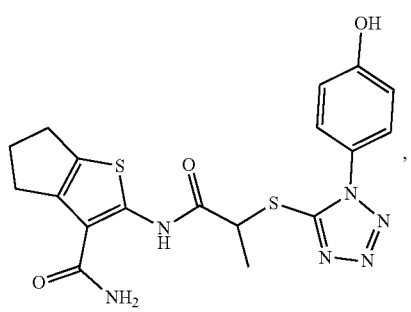
MASM41
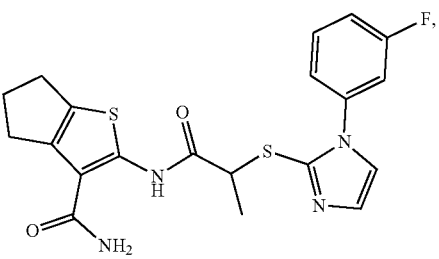

-continued

MASM43

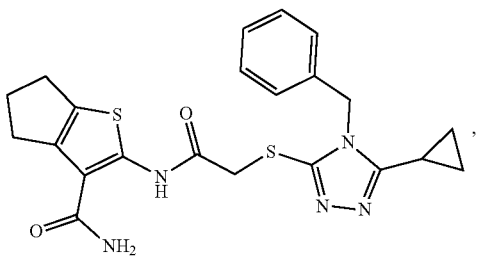

MASM45

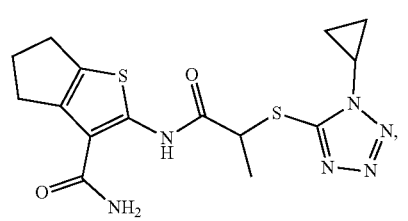

or a pharmaceutically acceptable salt, ester or prodrug thereof.

3. The method of claim 1, wherein the compound activates mitofusin 1.

4. The method of claim 1, wherein the compound activates mitofusin 2 (Mfn2).

5. The method of claim 1, wherein the disease or disorder is heart failure, or cardiomyopathy.

6. The method of claim 1, wherein the cancer disease or disorder is Hail leukemia.

7. The method of claim 6, wherein the leukemia is acute lymphoblastic leukemia (ALL), acute myeloid leukemia (AML), chronic lymphocytic leukemia (CLL) or chronic myeloid leukemia (CIVIL).

8. The method of claim 1, wherein the disease or disorder is breast cancer pancreatic cancer liver cancer, or cervical carcinoma.

9. A pharmaceutical composition comprising a pharmaceutically acceptable carrier and a therapeutically effective amount of a compound of formula (III),
wherein

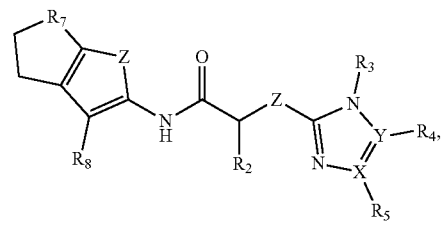

(III)

wherein
R2 is H or $C_1$-$C_4$ alkyl;
R3 and R5 are independently H, alkenyl, alkynyl, cycloalkyl, $CHCH_3N(CH_3)_2$, heterocycloalkyl, benzyl, aryl, heteroaryl, aralkyl, heteroaralkyl, or optionally substituted aryl, aralkyl, heteroaryl, or heteroaralkyl, wherein the optional substituent is one or more of F, Cl, Br, I, OH, $CH_3$, SH, or $CF_3$;
R4 is H, alkenyl, alkynyl, cycloalkyl, $CHCH_3N(CH_3)_2$, heterocycloalkyl, benzyl, aryl, 5- or 6-membered heteroaryl, aralkyl, heteroaralkyl, or optionally substituted 6-membered aryl, aralkyl, 5- or 6-membered heteroaryl, or heteroaralkyl, wherein the optional substituent is one or more of F, Cl, Br, I, OH, $CH_3$, SH or $CF_3$;
R7 is $CH_2$, $CH_2CH_2$, $CH_2CH_2CH_2$ or $CH_2CH(CH_3)$;
R8 is CN, $CONH_2$, COOH or COOR9;
R9 is $C_1$-$C_4$ alkyl;
X and Y are independently N or C;
Z is S;
provided that in Formula III when R4 or R5 is heteroaryl and R8 is $CONH_2$, R2 is not H;
or a pharmaceutically acceptable salt, ester or prodrug thereof,
provided that the compound is not any of the following:

MASM20

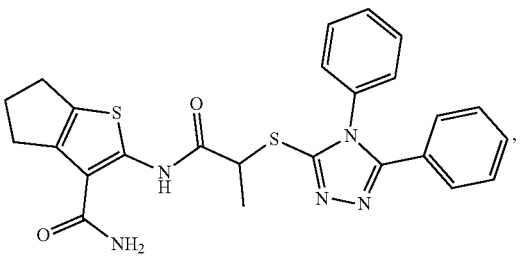

MASM21

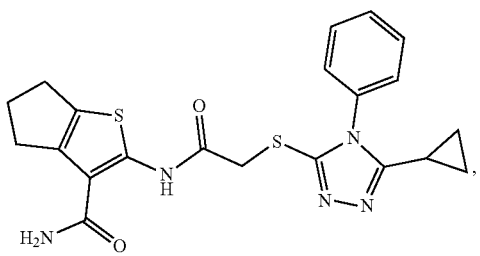

MASM25

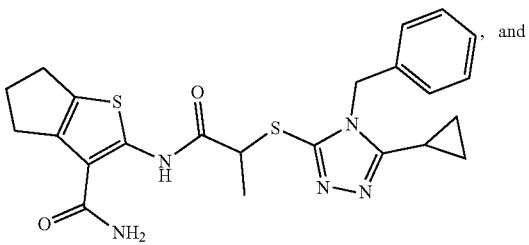

, and

MASM29

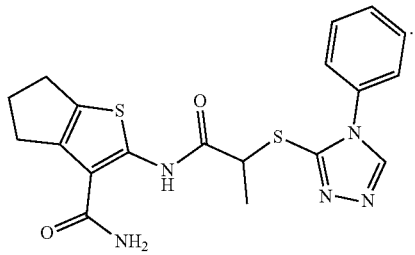

10. A pharmaceutical composition comprising a pharmaceutically acceptable carrier and a therapeutically effective amount of one or more compounds selected from the group consisting of:

MASM7
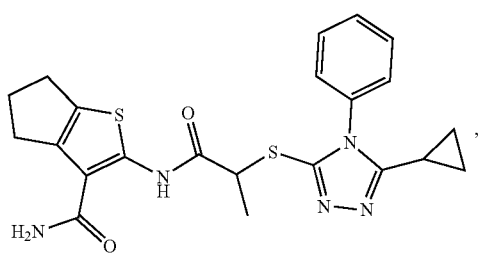
MASM22
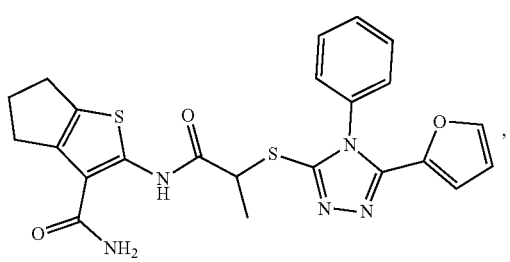
MASM23
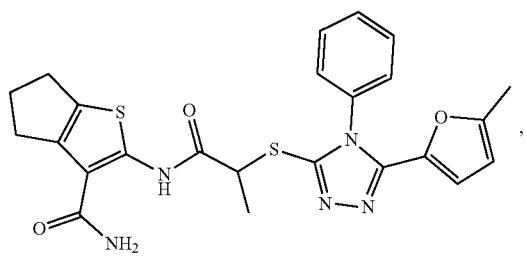
MASM24
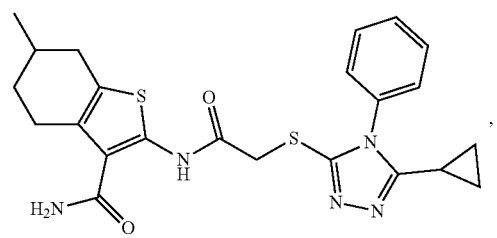
MASM27
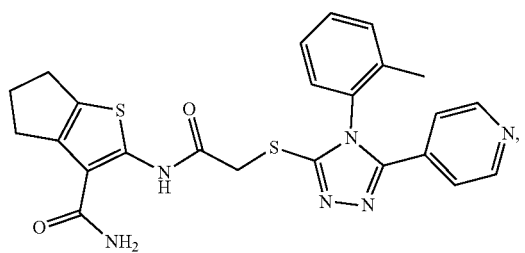
MASM28
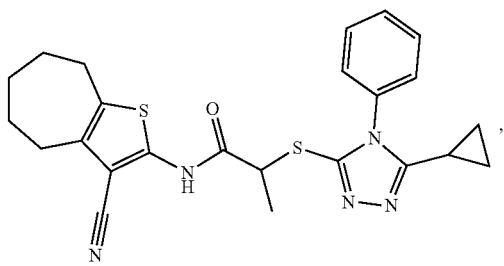
MASM30
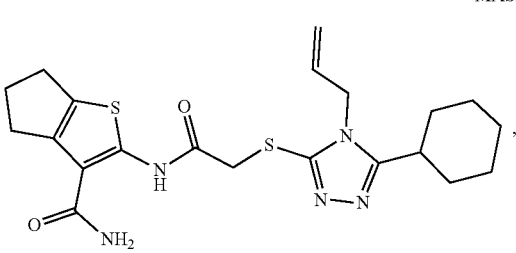
MASM31
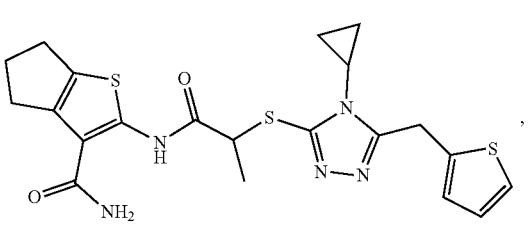
MASM32
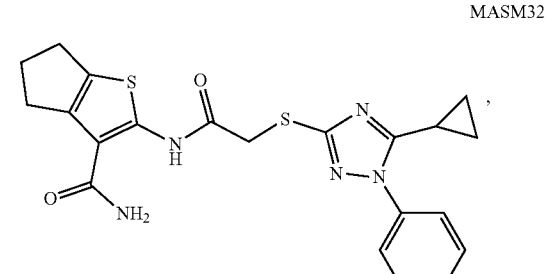
MASM33
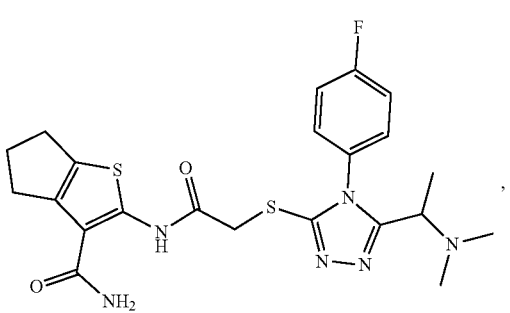

MASM36
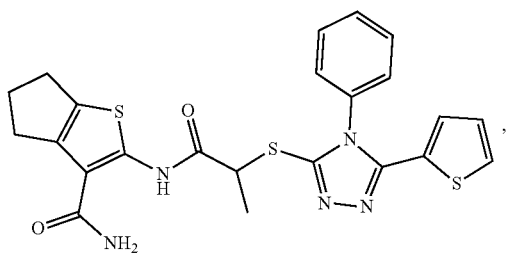

MASM37
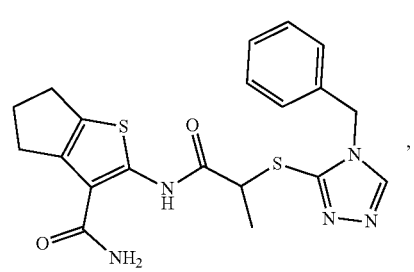

MASM39
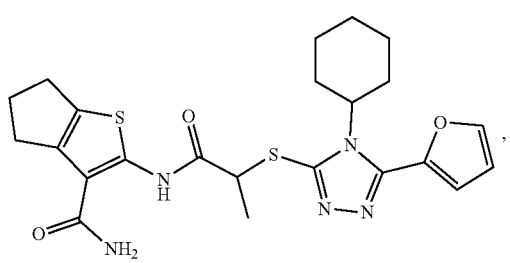

MASM40
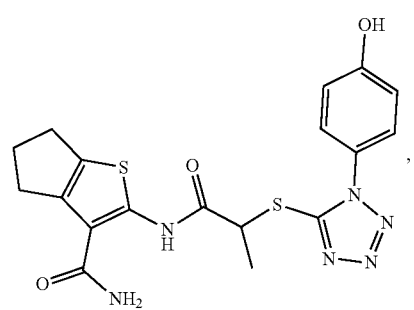

MASM41
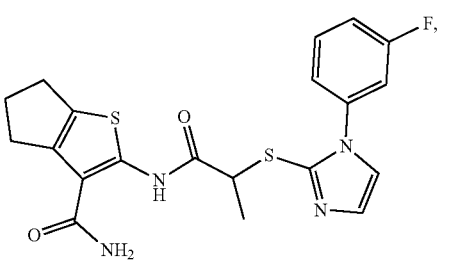

MASM43
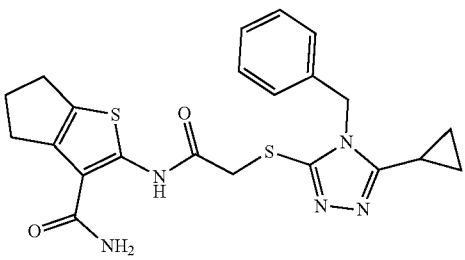

MASM45
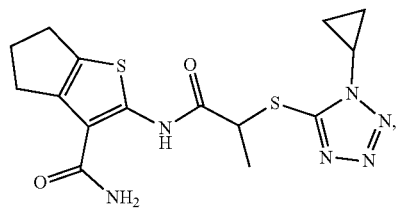

or a pharmaceutically acceptable salt, ester or prodrug thereof.

11. The pharmaceutical composition of claim 9, wherein the compound is present in the composition in an amount effective to activate a mitofusin.

12. The pharmaceutical composition of claim 9, wherein the compound is present in the composition in an amount effective to activate mitofusin 2 (Mfn2).

13. The method of claim 1, wherein X is N, and Y is C.

14. A method of activating Mfn1 or Mfn2, comprising contacting the Mfn1 or the Mfn2 with a compound of Formula III, Formula III
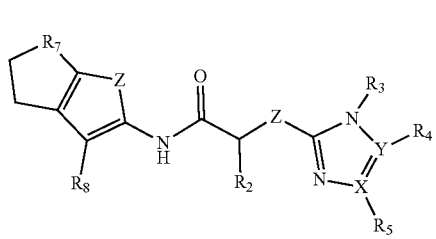

wherein
R2 is H or $C_1$-$C_4$ alkyl;
R3 and R5 are independently H, alkenyl, alkynyl, cycloalkyl, $CHCH_3N(CH_3)_2$, heterocycloalkyl, benzyl, aryl, heteroaryl, aralkyl, heteroaralkyl, or optionally substituted aryl, aralkyl, heteroaryl, or heteroaralkyl, wherein the optional substituent is one or more of F, Cl, Br, I, OH, $CH_3$, SH, or $CF_3$;
R4 is H, alkenyl, alkynyl, cycloalkyl, $CHCH_3N(CH_3)_2$, heterocycloalkyl, benzyl, aryl, 5- or 6-membered heteroaryl, aralkyl, heteroaralkyl, or optionally substituted 6-membered aryl, aralkyl, 5- or 6-membered heteroaryl, or heteroaralkyl, wherein the optional substituent is one or more of F, Cl, Br, I, OH, $CH_3$, SH or $CF_3$;
R7 is $CH_2$, $CH_2CH_2$, $CH_2CH_2CH_2$ or $CH_2CH(CH_3)$;
R8 is CN, $CONH_2$, COOH or COORS;
R9 is $C_1$-$C_4$ alkyl;
X and Y are independently N or C;
Z is S;
provided that when R4 or R5 is heteroaryl and R8 is $CONH_2$, R2 is not H;

or a pharmaceutically acceptable salt thereof,
provided that the compound is not any of the following:
MASM20
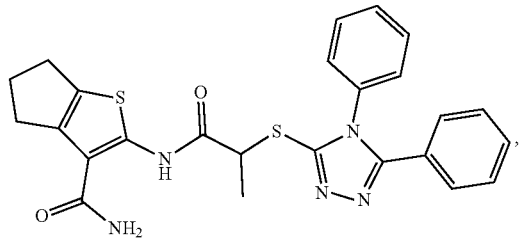
MASM21
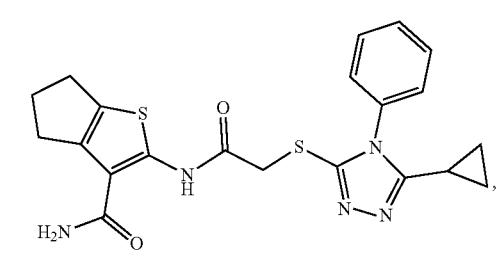
MASM25
, and
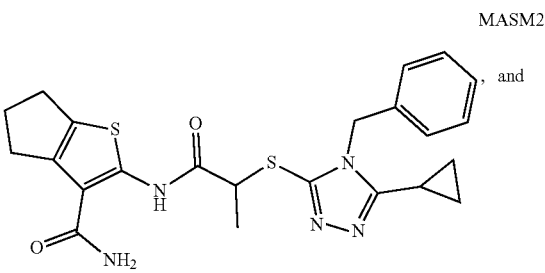
MASM29
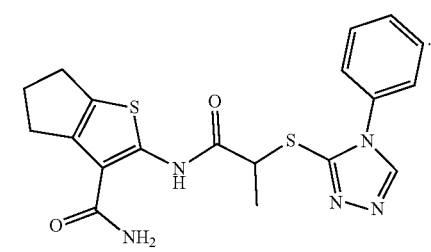
15. The method of claim 14, wherein the compound is selected from the group consisting of
MASM7
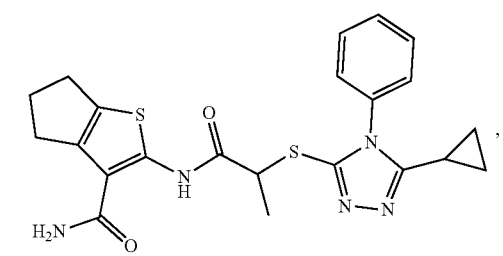
MASM22
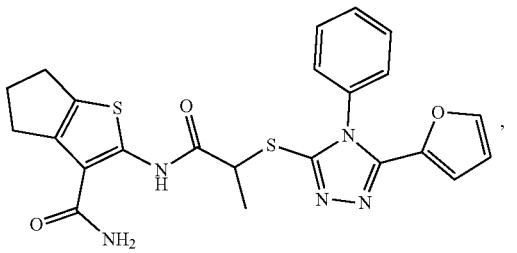
MASM23
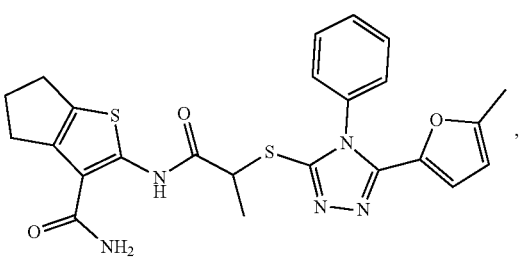
MASM24
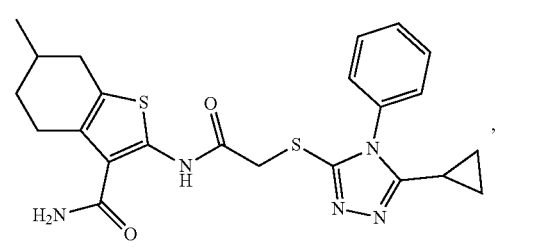
MASM27
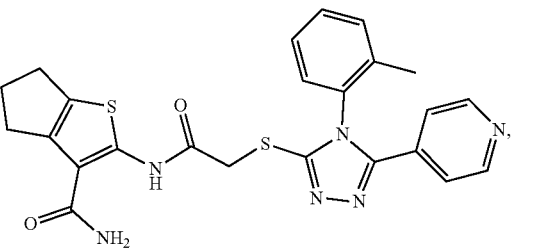
MASM28
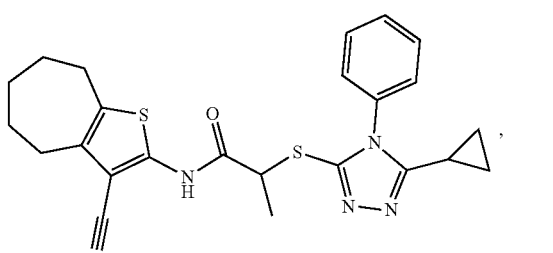
MASM30
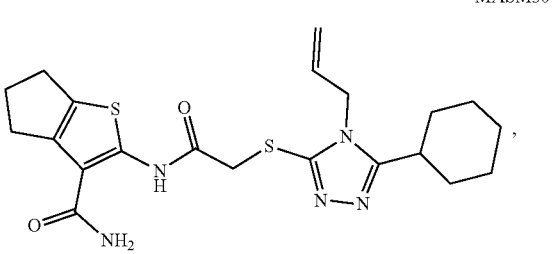

MASM31
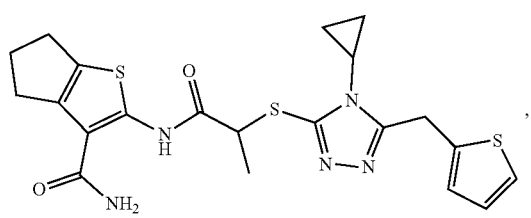
MASM32
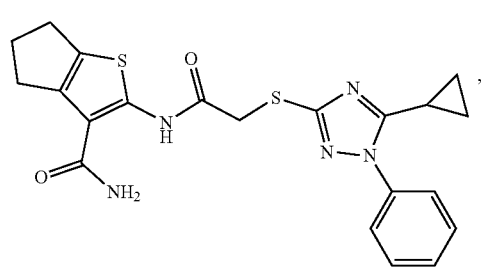
MASM33
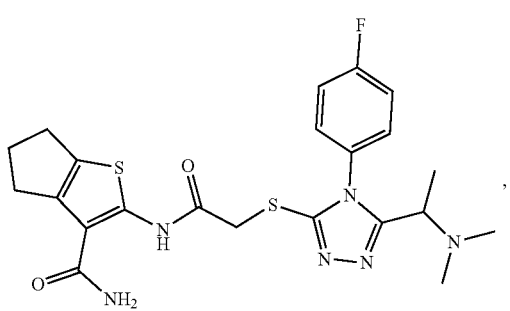
MASM36
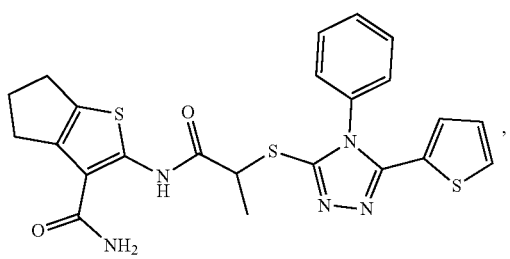
MASM37
MASM39
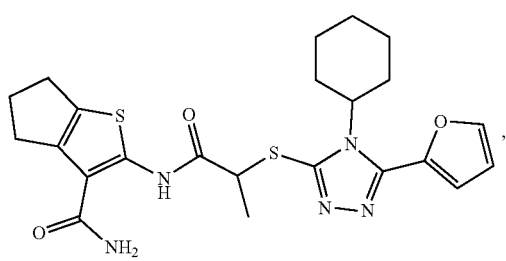
MASM40
MASM41
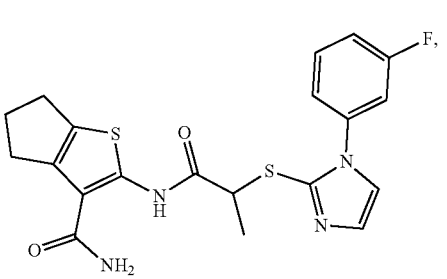

-continued
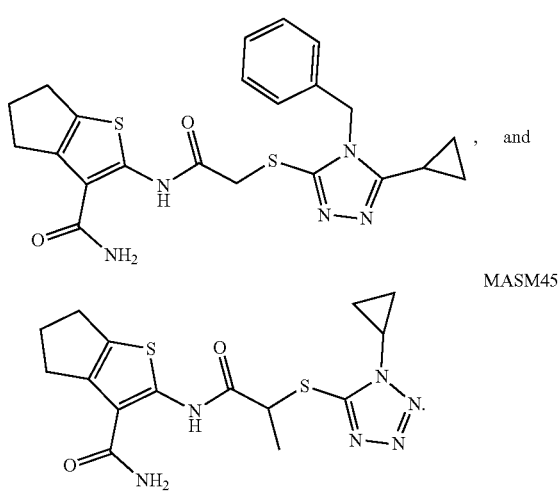
MASM43
MASM45
16. The pharmaceutical composition of claim 10, wherein the compound is MASM7
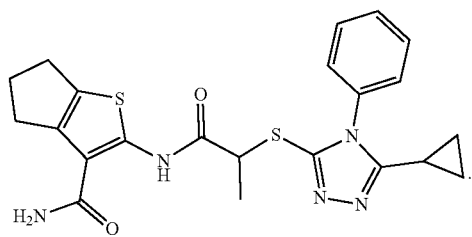
MASM7
* * * * *

SEQUENCE LISTING

<160> NUMBER OF SEQ ID NOS: 7

<210> SEQ ID NO 1
<211> LENGTH: 30
<212> TYPE: PRT
<213> ORGANISM: Artificial Sequence
<220> FEATURE:
<223> OTHER INFORMATION: Pro-fusion 367-384 Gly peptide

<400> SEQUENCE: 1

Gln Ile Ala Glu Val Arg Gly Ile Met Asp Ser Leu His Met Ala Ala
1               5                   10                  15

Arg Gly Gly Tyr Gly Arg Lys Lys Arg Gln Arg Arg
            20                  25                  30

<210> SEQ ID NO 2
<211> LENGTH: 28
<212> TYPE: DNA
<213> ORGANISM: Artificial Sequence
<220> FEATURE:
<223> OTHER INFORMATION: forward primer for mCerulean (cyan fluorescent
      protein; CFP) flanked with two restrict enzyme sites BamHI and
      EcoRI at 5' and 3', respectively

<400> SEQUENCE: 2
agcccgggat ccaccatggt gtccaaag                                      28

<210> SEQ ID NO 3
<211> LENGTH: 43
<212> TYPE: DNA
<213> ORGANISM: Artificial Sequence
<220> FEATURE:
<223> OTHER INFORMATION: reverse primer for mCerulean (cyan fluorescent
      protein; CFP) flanked with two restrict enzyme sites BamHI and
      EcoRI at 5' and 3', respectively

<400> SEQUENCE: 3
cctgggaatg gatgaactgt ataaaaagaa ttccctgctc ttc                     43

<210> SEQ ID NO 4
<211> LENGTH: 39

```
<212> TYPE: DNA
<213> ORGANISM: Artificial Sequence
<220> FEATURE:
<223> OTHER INFORMATION: forward primer for mVenus (yellow fluorescent
      protein; YFP) bearing a stop codon TAG

<400> SEQUENCE: 4
cctgcagccc agcagatggg caatggtgag caagggcga                              39

<210> SEQ ID NO 5
<211> LENGTH: 40
<212> TYPE: DNA
<213> ORGANISM: Artificial Sequence
<220> FEATURE:
<223> OTHER INFORMATION: reverse primer for mVenus (yellow fluorescent
      protein; YFP) bearing a stop codon TAG

<400> SEQUENCE: 5
aaacgggccc tctagactcg agctacttgt acagctcgtc                             40

<210> SEQ ID NO 6
<211> LENGTH: 40
<212> TYPE: DNA
<213> ORGANISM: Artificial Sequence
<220> FEATURE:
<223> OTHER INFORMATION: forward primer for FRED-Mfn2-D725/L727

<400> SEQUENCE: 6
gaaaattgag gttcttgcct cagctcagag caaagcaaag                             40

<210> SEQ ID NO 7
<211> LENGTH: 40
<212> TYPE: DNA
<213> ORGANISM: Artificial Sequence
<220> FEATURE:
<223> OTHER INFORMATION: reverse primer for FRED-Mfn2-D725/L727

<400> SEQUENCE: 7
ctttgctttg ctctgagctg aggcaagaac ctcaatttc                              40
```